(12) United States Patent
Sagt et al.

(10) Patent No.: US 8,129,143 B2
(45) Date of Patent: Mar. 6, 2012

(54) METHOD FOR PRODUCTION OF A COMPOUND IN A EUKARYOTIC CELL

(75) Inventors: Cornelis Maria Jacobus Sagt, Utrecht (NL); Petrus Johannes Fredrik ten Haaft, Delft (NL); Johannes Hendrik de Winde, Voorhout (NL); Panagiotis Sarantinopoulos, Delft (NL)

(73) Assignee: DSM IP Assets B.V., TE Heerlen (NL)

(*) Notice: Subject to any disclaimer, the term of this patent is extended or adjusted under 35 U.S.C. 154(b) by 887 days.

(21) Appl. No.: 11/664,591

(22) PCT Filed: Oct. 13, 2005

(86) PCT No.: PCT/EP2005/055229
§ 371 (c)(1),
(2), (4) Date: Apr. 4, 2007

(87) PCT Pub. No.: WO2006/040340
PCT Pub. Date: Apr. 20, 2006

(65) Prior Publication Data
US 2008/0026421 A1    Jan. 31, 2008

(30) Foreign Application Priority Data

Oct. 15, 2004  (EP) .................................. 04105077
Jul. 7, 2005   (EP) .................................. 05106200

(51) Int. Cl.
  C12P 21/00   (2006.01)
  C07K 14/00   (2006.01)
  C12N 1/12    (2006.01)
  C12N 1/14    (2006.01)

(52) U.S. Cl. .................. 435/69.1; 435/69.9; 435/254.1; 435/255.2

(58) Field of Classification Search .................. None
See application file for complete search history.

(56) References Cited

U.S. PATENT DOCUMENTS
2003/0186379 A1* 10/2003 Lee et al. ..................... 435/69.1

FOREIGN PATENT DOCUMENTS
WO    03/008536 A2    1/2003
WO    2006/040340 A3  8/2006

OTHER PUBLICATIONS

Pause et al Targeting of the 22 kDa integral peroxisomal membrane protein FEBS Letters 471 (2000) 23-28.*
Faber et al (Foreign gene expression in Hansenula polymorpha. A system for the synthesis of small functional peptides. A system for the synthesis of small functional peptide. Applied Microbiological Biotechnology (1996) 45: 72-79).*
Fusion of Small Peroxisomal Vesicles In Vitro Reconstructs an Early Step in the In Vivo Multistep Peroxisome Assembly Pathway of Yarrowia lipolytica Vladimir I. Titorenko et al Journal of Biochemistry pp. 29-43, 2000.*
Review: Methylotrophic Yeasts as Factories for the Production of Foreign Proteins Klaas Nico Faber et al Yeast vol. 11:1331-1334 (1995).*
Elgersma et al Overexpression of Pex15p, a phosphorylated peroxisomal integral membrane protein required for peroxisome assembly in S. cerevisiae, causes proliferation of the endoplasmic reticulum membrane The EMBO Journal vol. 16 No. 24 pp. 7326-7341, 1997.*
Kim et al. "Autophagy, cytoplasm-to-vacuole targeting pathway, and pexophagy in yeast and mammalian cells" Annual Review of Biochemistry, vol. 69, pp. 303-342, 2000.
Petriv et al. "A new definition for the consensus sequence of the peroxisome targeting signal type 2" J. Mol. Biol., vol. 341, No. 1, pp. 119-134, Jul. 2004.
Database UniProt "25D9-6" EBI accession No. UNIPROT:Q876M4, database accession No. Q876M4, Jun. 2003.
Database UniProt, "Putative Synaptobrevin" EBI accession No. UNIPROT:Q6UNZ8, Database accession No. Q6UNZ8, Jul. 2004.

* cited by examiner

*Primary Examiner* — Kagnew H Gebreyesus
(74) *Attorney, Agent, or Firm* — Nixon & Vanderhye

(57) ABSTRACT

The present invention relates to a eukaryotic cell containing peroxisomes that are capable to fuse with a membrane-structure of the cell involved in the secretory pathway of the cell. In this way, the eukaryotic cell is able to release the peroxisomal content outside the cell. The invention also relates to a method for production of a compound of interest in said eukaryotic cell wherein said compound of interest is present in the peroxisome of the cell. Said compound of interest will accumulate in the peroxisome by a signal promoting peroxisome localization. Preferred host cells are filamentous fungal cells.

14 Claims, 12 Drawing Sheets

| A. niger strain | 24 hours amdS | 48 hours amdS |
|---|---|---|
| GFP-SKL | 0.007 | 0.039 |
| GFP-SKL + C2-ceramide | -0.008 | 0.044 |
| GFP-SKL + SNC/PMP | -0.011 | 0.053 |
| GFP-SKL + SNC/PMP + C2-ceramide | -0.011 | 0.056 |
| GFP-SKL + SNC/PMP + PEX-11 | -0.011 | 0.054 |
| GFP-SKL + SNC/PMP + PEX-11 + C2-ceramide | -0.011 | 0.050 |
| Empty control strain | -0.004 | 0.054 |
| Empty control strain + C2-ceramide | 0.001 | 0.052 |

METHOD FOR PRODUCTION OF A COMPOUND IN A EUKARYOTIC CELL

This application is a U.S. national stage of International Patent Application No. PCT/EP2005/055229, filed 13 Oct. 2005, which designated the U.S. and claims priority benefit of EP 04105077.4, filed 15 Oct. 2004; and EP 05106200.8, filed 7 Jul. 2005; the entire contents of each of which are hereby incorporated by reference.

FIELD OF THE INVENTION

The present invention relates to recombinant-DNA-technology. Specifically, this invention relates to a method for production of a compound in a eukaryotic cell, wherein the compound is present in a peroxisome capable of fusion with a membrane-structure of the cell involved in the secretory pathway of the cell, causing the compound to be released outside of the cell.

BACKGROUND OF THE INVENTION

Secretion of proteins by eukaryotic cells into the culture medium involves transfer of the proteins through the various membrane-enclosed compartments constituting the secretory pathway. First, the proteins are translocated into the lumen of the endoplasmic reticulum (ER). From there on, the proteins are transported in membrane vesicles to the Golgi complex and from the Golgi complex to the plasma membrane. The secretory pathway involves several steps in which vesicles containing the secreted proteins are pinched off from the donor membrane, targeted to and fused with the acceptor membrane. At each of these steps, the function of several proteins such as chaperones or folding enzymes is needed in order to perform adequate maturation of the proteins including glycosylation and disulphide bridge formation. The extracellular proteins mature in the oxidizing environment of the ER where they become core glycosylated and this glycosylation process is subsequently completed in the Golgi complex.

Several attempts have been made to increase protein secretion in eukaryotes. A common approach to increase secretion of heterologous proteins is to use signal sequences (see for example EP 0215 594). The conventional secretory pathway in eukaryotic cells, as outlined above, is by definition adapted to the maturation of extracellular proteins. The maturation of intracellular proteins is realized in the reducing environment of the cytoplasm having specific chaperones and folding proteins. Production of proteins, especially intracellular proteins, in an industrial setting is still a difficult task due to the low yield of proteins caused by the inefficiency of both the secretion and the down stream processing (Hopkins T R. Physical and chemical cell disruption for the recovery of intracellular proteins. Bioprocess Technol. 1991; 12:57-83.)

Due to the growing industrial importance to produce proteins and to the poor efficiency of both secretion and down stream processing pathways, there is still a need to obtain improved process for production of proteins in eukaryotic cells. The present invention provides a novel method to produce proteins with high efficiency.

DESCRIPTION OF THE FIGURES

FIG. 10 shows the degree of a-specific lyses of cells, depicted as relative amounts of acetamidase (amdS)/ml culture supernatant.

DETAILED DESCRIPTION OF THE INVENTION

Figure 1:
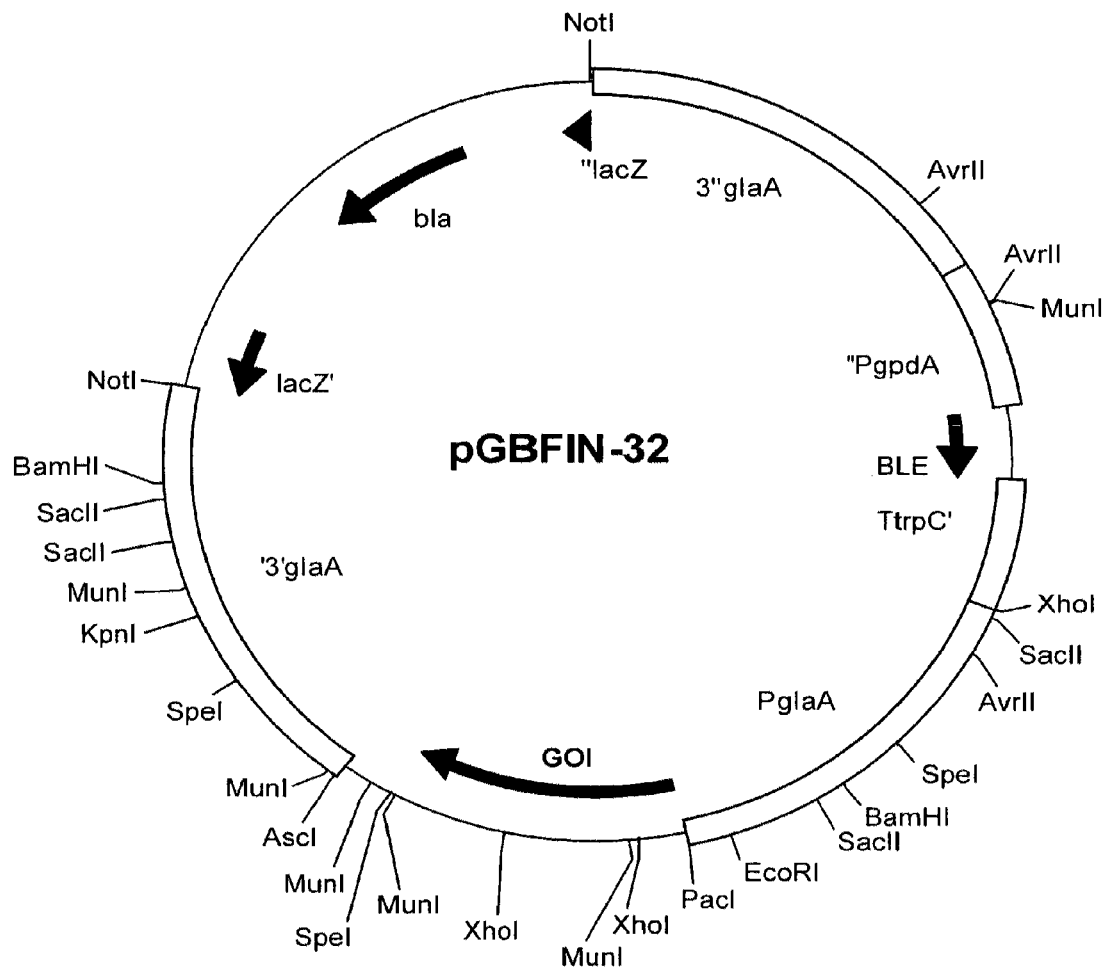
FIG. 1 depicts the *A. niger* expression vector pGBFIN-32.

In a first aspect, the invention relates to a eukaryotic cell containing peroxisomes that are capable to fuse with a membrane-structure of the cell involved in the secretory pathway of the cell. In this way, the present invention provides a novel capability of eukaryotic cells in that they are capable to release the content of a peroxisome outside of the cell. In this way, compounds that otherwise would not be secreted by a eukaryotic cell can now be advantageously released via the peroxisomal route.

According to the invention, fusion of a peroxisome with a membrane-structure of the cell involved in the secretory pathway of the cell is equivalent with fusion of the peroxisomal membrane with a membrane-structure of the cell involved in the secretory pathway of the cell. Fusion means the merging of diverse elements to form a unified whole: one element is here the peroxisomal membrane and other elements are membranes from membrane-structures of the cell involved in the secretory pathway of the cell. Fusion of a peroxisomal lipid bilayer membrane with a lipid bilayer membrane of a membrane structure of the secretory pathway is herein understood to mean that the two lipid bilayer membranes form one single, continuous lipid bilayer membrane surrounding the contents of both the peroxisome and the membrane structure of the secretory pathway. In the case that a peroxisomal lipid bilayer membrane fuses with the plasma membrane to form one single, continuous lipid bilayer membrane it is understood that newly formed single membrane will not surround the contents of the peroxisome but rather the peroxisomal contents will be released into the extracellular environment. For example, if fusion of peroxisome with the plasma membrane occurs, the peroxisomal content will be directly exported outside of the cell. In another example, if the fusion of the peroxisome with the Golgi complex and/or with the ER occurs, the peroxisomal content will be translocated into the Golgi complex and/or the ER, thereby being indirectly exported outside of the cell via the endogenous secretory pathway of the cell.

A peroxisome (also called microbody) is defined as a single membrane-bound organelle involved in a variety of metabolic processes ubiquitously found in eukaryotic cells (Sakai et al. Yeast 14, 1175-1187; 1998). In eukaryotic cells, peroxisomes normally do not fuse with a membrane-structure of the cell involved in the secretory pathway of the cell but are maintained as single membrane-bound organelles within the cytosol.

In the context of the invention, a membrane-structure of the cell involved in the secretory pathway of the cell may be any membrane-structure involved in the secretion of a polypeptide by the cell. Throughout this invention, the phrase "membrane-structure of the cell involved in the secretory pathway of the cell" and the term "membrane-structure" are used synonymously. Preferably, the membrane-structure of the cell involved in the secretory pathway of the cell is selected from the group consisting of the plasma membrane, the Golgi complex and the Endoplasmic Reticulum (ER). The Golgi complex is defined as to include minimally three (cis-, medial- and trans-Golgi) distinct flattened membrane-bound compartments (cisternae), which associate with each other to form a stack (Pfeffer S R, Constructing a Golgi complex. J Cell Biol. 2001 Dec. 10; 155(6):873-5).

The process of membrane-fusion within the secretory pathway is highly conserved in all eukaryotic species. According to the present state of the art, the central components driving membrane-fusion are polypeptides called SNAREs (Soluble N-ethylmaleimide-sensitive factor Attachment protein REceptors). Complementary SNAREs are present on donor (v-SNAREs and acceptor membranes (t-SNARES) and are distinguished by a conserved sequence motif (SNARE motif). To mediate membrane-fusion, four SNARE motifs bundle to form a parallel coiled-coil structure, referred to as SNAREpin. The SNAREpin is comprised of at least one membrane-anchored SNARE on the acceptor membrane-structure and at least one membrane-anchored SNARE on the donor membrane-structure. Soluble or alternatively membrane-bound SNAREs containing one or two SNARE motifs (e.g. Sec9) may complement SNAREpin formation. The arrangement of SNAREpin components in the donor:acceptor membrane-structures may be 1:3, but can also be 2:2. (Burri L, Lithgow T. A complete set of SNAREs in yeast. Traffic. 2004 January; 5(1):45-52).

According to the invention, the fusion of the peroxisome membrane with a membrane-structure of the cell involved in the secretory pathway of the cell can be effectuated in several ways, which can be used alone or in combination.

The present invention discloses that to obtain fusion of a peroxisome with the plasma membrane (or another membrane of the secretory pathway) of a eukaryotic cell, one preferred option is to expose a fusing-polypeptide or a part thereof at the surface of the peroxisome. According to the invention, a fusing-polypeptide is a polypeptide involved in the fusion of a donor membrane-structure with an acceptor membrane-structure and normally exposed at the surface of the donor membrane-structure. Exposed at the surface is herein understood to mean exposed at the cytosolic side of donor membrane, as opposed to the luminal side. A donor membrane-structure is defined as a membrane-structure that is capable to generate vesicles that are able to fuse with an acceptor membrane-structure. Preferably the donor and acceptor membrane structures are membranes of the secretory pathway. More preferably, the donor membrane-structure is selected from the group consisting of the Golgi complex and the ER.

Fusing-polypeptides typically comprise a part exposed at the surface of the donor membrane-structure, e.g. the Golgi complex or the ER, and a transmembrane-domain. In a preferred embodiment, that part of the fusing-polypeptide normally exposed at the surface of the donor membrane-structure, i.e. the surface exposed domain, is used for exposure at the surface of the peroxisome.

In a preferred embodiment, the donor membrane-structure is the Golgi complex, i.e. the fusing-polypeptide is a polypeptide normally expressed at the surface of a vesicle of the Golgi complex and known to be involved in the fusion of the Golgi vesicle with the plasma membrane.

Preferred fusing-polypeptides are polypeptides of the family of v-SNARE polypeptides or v-SNAREs as described in: vesicle-SNAREs, Jahn et al, Annu Rev. Biochem. (1999) 863-911; Burri et al. supra. Preferred v-SNAREs are further defined herein below by means of sequence identity to SEQ ID NO: 13.

Several v-SNAREs expressed at the surface of a vesicle of the Golgi complex have already been described, e.g. Snc1 and Snc2 (Burri et al. supra). Examples of a v-SNARE expressed at the surface of the ER are Sec22 and Ykt6 (Burri et al. supra). In a preferred embodiment of the invention, at least one of the v-SNAREs Snc1 or Snc2, or a homologue thereof, is used. An example of a Snc1/Snc2 homologue is the *Aspergillus niger* SncA polypeptide as provided by the present invention.

The present invention encompasses the use of homologues of any polypeptide (or its encoding gene) that is described in the present invention with reference to its origin from a specific reference species, usually yeast (*S. cerevisiae*). Thus, a homologue (or a homologous sequence) is defined as a polypeptide from another species than the reference species that exerts substantially the same function as the polypeptide of the reference species, although the homologue may have a different name than the name used in the reference species. Typically, such a homologue may have a degree of identity with the polypeptide of the reference species of at least 50%. Such a homologue preferably originates from the same eukaryotic species as the eukaryotic cell that is modified according to the present invention.

To obtain exposure of a fusing-polypeptide, such as a v-SNARE, at the peroxisomal surface, the fusing-polypeptide or at least a part thereof that is capable of a function interaction with the complementary SNARE on the acceptor membrane is operatively associated with, preferably fused to, a peroxisomal membrane-polypeptide or part thereof. In this way a chimeric polypeptide is obtained comprising a fusing-polypeptide part or component and a peroxisomal membrane-polypeptide part or component.

The peroxisomal membrane-polypeptide or part thereof, as component of the chimeric polypeptide, preferably is capable of mediating targeting of the chimeric polypeptide to the peroxisomal membrane and more preferably the peroxisomal membrane polypeptide or part thereof is capable of anchoring the chimeric polypeptide into the peroxisomal membrane. Most preferably, anchoring of the chimeric polypeptide into the peroxisomal membrane is effected by the peroxisomal membrane polypeptide or part thereof by integration of at least one membrane spanning transmembrane segment into the peroxisomal membrane. Preferably the localisation of the entire chimeric polypeptide in the peroxisomal membrane is such that it functions as a membrane-anchor and at the same time exposes the fusing-polypeptide part of the chimeric polypeptide on the (cytosolic) surface of the peroxisome. Preferably, the peroxisomal membrane-polypeptide is trimmed at the N-terminal part to result in exposure of the fusing-polypeptide as close as possible to the peroxisomal membrane, without abrogating peroxisomal targeting of the chimeric fusing-polypeptide.

Preferably, that part of the fusing-polypeptide, such as a v-SNARE, is used as component of the chimeric polypeptide that comprises at least the domain of the fusing-polypeptide normally exposed at the surface of the donor membrane-structure, such as a Golgi vesicle. The transmembrane domain(s) of the fusing-polypeptide may be absent in the chimeric polypeptide, either partly or completely.

Any peroxisomal membrane-polypeptide or a part thereof suitable to function as a peroxisomal membrane-anchor is suitable to be used for operative association with, preferably fusion to, at least the surface-exposed domain of a fusing-polypeptide, as long as the result is a chimeric peptide comprising the fusing-polypeptide part located at the cytosolic side (or surface) of the peroxisome (to be able to interact with the membrane-structure of the cell involved in the secretory pathway of the cell). Preferably, the fusing-polypeptide part is located at the N-terminal part of the chimeric polypeptide and therefore, preferably, the peroxisomal membrane polypeptide is a polypeptide of which the N-terminus is naturally exposed to the cytosolic side of the peroxisome, or that has at least one transmembrane segment of which the natural orientation is such that N-terminus of the segment is directed towards to cytosol.

An example of a preferred peroxisomal membrane polypeptide is Peroxisomal Membrane Polypeptide 22 (Pmp22) or a homologue thereof (Brosius U, Dehmel T, Gartner J. Two different targeting signals direct human peroxisomal membrane protein 22 to peroxisomes. J Biol. Chem. 2002 Jan. 4; 277(1):774-84). An example of a Pmp22 homologue is the *Aspergillus niger* Pmp22 as provided by the present invention. Brosius et al. (2002, supra) have shown that the human and rat Pmp22 proteins have 4 transmembrane domains (1 through in a N- to C-terminal direction) and 2 independent peroxisomal targeting signals located at the N-termini of the first and second transmembrane domains. According to a preferred embodiment, the part of the Pmp22 polypeptide that is used as component of the chimeric polypeptide therefore comprises at least peroxisomal transmembrane domains 3 and 4 of Pmp22, and more preferably all 4 peroxisomal transmembrane domains of Pmp22. Preferably, the part of the Pmp22 polypeptide that is used as component of the chimeric polypeptide comprising only peroxisomal transmembrane domains 3 and 4 of Pmp22 in addition comprising sufficient amino acids N-terminal to transmembrane domain 3 to include a functional peroxisomal targeting signal. Preferably at least 15, 12, 10, 8 or 7 amino acids N-terminal to transmembrane domain 3 as defined by Brosius et al. (2002, supra) are included.

Other suitable peroxisomal membrane proteins (or parts thereof suitable to function as a peroxisomal membrane anchor) that are suited to be used for operative association with, preferably fusion to, at least the surface-exposed domain of a fusing polypeptide include, but are not limited to, e.g. PMP34, PMP47, PMP70, PEX3, PEX11, PEX14, and PEX22 (reviewed in Eckert J H and Erdmann R., Peroxisome biogenesis. Rev Physiol Biochem Pharmacol. 2003; 147:75-121).

Preferably, Pmp22 or another peroxisomal membrane protein is trimmed at the N-terminal part as described above. Said trimming comprises a deletion of at least the first methionine. The trimming on the N-terminal part may further comprise the deletion of the N-terminal 1 to 50, e.g. 48, amino acids, preferably of the N-terminal 1 to 35, e.g. 33, amino acids, more preferably of the N-terminal 1 to 20, e.g. 18, amino acids. Preferably the N-terminus of a peroxisomal membrane protein is trimmed such that at least 15, 12, 10, 8, 7, 5 or 3 amino acids remain that are N-terminal to the first (in a N- to C-terminal direction) transmembrane domain of which the natural orientation is such that N-terminus of the segment is directed towards to cytosol. Preferably, trimming of the N-terminus of a peroxisomal membrane protein does not delete or disrupt amino acid sequences required for peroxisomal targeting.

According to a preferred embodiment, the domain of a v-SNARE (e.g. Snc1, Snc2 or SncA) normally exposed at the surface of the donor membrane-structure is operatively associated with (fused to) the peroxisomal membrane polypeptide Pmp22, to decorate peroxisomes with the corresponding part of the v-SNARE, e.g. Snc1, Snc2 or SncA. More preferably, the surface exposed domain of SncA is used. Even more preferably, the chimeric polypeptide has an amino acid sequence according to SEQ ID NO: 24. The skilled person will know how to construct chimeric polypeptides from Pmp22 polypeptide orthologues and v-SNARE orthologues from other organisms according to the same principle as described for SEQ ID NO: 24.

In one embodiment of the invention, exposure of a fusing-polypeptide at the surface of the peroxisome is accompanied by over-expression of a complementing fusing-polypeptide at the acceptor membrane-structure of the cell, e.g. the plasma membrane or the Golgi complex. A "complementing fusing-polypeptide" according to the invention is a polypeptide involved in facilitating the fusion of a donor membrane-structure, e.g. a vesicle of the Golgi complex or the ER, with an acceptor membrane-structure, e.g. the plasma membrane or the Golgi complex A complementing fusing-polypeptide is preferably a target-SNARE or t-SNARE (Jahn et al., Annu. Rev. Biochem. 863-911 (1999)). Preferred t-SNARE polypeptides are for instance Sso1 or Sso2, or homologues thereof, which are located at the plasma membrane, or Sed5, or homologues thereof, which is located at the Golgi complex (Burri et al. supra). Other preferred complementing fusing-polypeptides are Sec9 involved in fusion at the plasma membrane or Bos1, Gos1, Bet1 or homologues thereof involved in fusion at the Golgi complex (Burri et al. supra).

According to a preferred embodiment, the fusing- and complementing fusing-polypeptides are exposed or overexpressed in stoichiometric amounts, meaning that the polypeptide interaction between a fusing- and a complementing fusing-polypeptide(s) is as close as possible to the physiological ratio or native stochiometry (Burri L et al, supra). A stoichiometric co-exposure is expected to further facilitate the fusion of the peroxisome with the acceptor membrane-structure, e.g. the plasma membrane. This stoichiometric co-expression is preferably achieved by using identical expression cassettes in substantially the same copy numbers. Preferably, the endogenous copy of the t-SNARE gene is left unaltered so that the amount of t-SNARE derived from the endogenous copy is available for fusion with the native vesicles of secretory pathway.

According to one embodiment of the invention, the eukaryotic cell contains peroxisomes capable to fuse with the plasma membrane as well as the Golgi complex of the cell.

According to a preferred embodiment, all the chosen fusing- and optional complementing fusing-polypeptide(s), and the peroxisomal membrane polypeptide to be expressed are native to the eukaryotic host cell of choice.

The present invention further envisages improvements of eukaryotic cells according to the invention such that the eukaryotic cells are capable of fulfilling the activities according to the invention with an increased efficiency.

For instance, targeting of the peroxisome to the plasma membrane and subsequent membrane-fusion may be enhanced by using the targeting mechanism of Golgi derived vesicles. Modification may allow this mechanism to be effective on peroxisomes.

An example to modify this mechanism to be effective on peroxisomes is to engineer Sec4, or a homologue thereof, such that it is operatively associated with the peroxisome. This will result in targeting of the peroxisome to the secretion complex in the plasma membrane (exocyst) and in addition will increase SNAREpin formation to enhance efficiency of peroxisomal fusion with the plasma membrane. Normally, Sec4 cycles between a GDP soluble state and a GTP bound secretion vesicle membrane attached state. It was demonstrated (Ossig et al 1995. EMBO Journal 3645-3653.) that a permanently attached Sec4 is biologically active. The membrane-attachment of Sec4 is normally achieved by geranylgeranylation of the two C-terminal cysteine residues. To allow permanent attachment of Sec4 to the peroxisomal membrane, the two C-terminal cysteine residues of Sec4 may be deleted or substituted by a different amino acid and a chimeric polypeptide comprising a peroxisomal membrane polypeptide or part thereof, may be engineered analogous to the already described chimeric polypeptide comprising a fusing-polypeptide and a peroxisomal membrane polypeptide.

In addition, the fusion of the peroxisome with the membrane-structure of the cell involved in the secretory pathway of the cell may be improved by making the complementing fusion polypeptide(s) more susceptible for interaction with the fusing-polypeptide. This can be done in various ways, as described below.

A constitutively active mutant of a fusing-polypeptide and, optionally, a complementing fusing-polypeptide may be prepared and (over-) exposed at the surface of the peroxisome and, optionally, the acceptor membrane-structure, e.g. the plasma membrane. An example of a constitutively active mutant is a dephosphorylated mutant of a complementing fusing-polypeptide, preferably a t-SNARE, more preferably Sso1 or a homologue thereof (Marash M, Gerst J E. t-SNARE dephosphorylation promotes SNARE assembly and exocytosis in yeast. EMBO J. 2001 Feb. 1; 20(3):411-21).

It is also possible to inactivate a regulator gene of a SNARE by techniques known to the skilled person. Such a regulator for instance is the v-SNARE master (VSM-1 or a homologue thereof), which binds to phosphorylated Sso1 and stabilizes the closed, inactive conformation of Sso1 (Marash M, Gerst J E. Mol Biol Cell. 2003 Aug.; 14 (8):3114-25).

It is also possible to over-express an enzyme known to activate SNARE interactions. Preferably, the Ceramide Activated Phosphatase Protein (CAPP) or a homologue thereof is over-expressed (Fishbein J D, Dobrowsky R T, Bielawska A, Garrett S, Hannun Y A. Ceramide-mediated growth inhibition and CAPP are conserved in *Saccharomyces cerevisiae*. J Biol. Chem. 1993 May 5; 268(13):9255-61).

It is also possible to modify the eukaryotic cell in such a way that the homeostasis of peroxisomes is affected. Such modification may comprise improving the rate of peroxisome biogenesis and/or decreasing the rate of peroxisome degradation as compared to the peroxisome biogenesis and/or degradation of the parental cell from which the eukaryotic cell according to the invention originates.

According to a more preferred embodiment, the eukaryotic cell has been genetically modified by (described in WO 00/71579):

(a) over-expressing genes involved in peroxisome biogenesis, e.g. pex11 and/or pex3 or homologues thereof, and/or (b) down-regulating the expression of genes involved in peroxisome degradation, e.g. vps15 and/or pdd1 and/or APG or homologues thereof.

The role of the pex3 and pex11 polypeptides in peroxisome biogenesis has already been described (Baerends R J, et al Yeast. 1997 December; 13(15):1449-63 and WO 00/71579). The role of Apg and Vps15 polypeptides in degradation of peroxisomes has also been described (Wang C W et al. J Biol. Chem. 2001 Aug. 10; 276(32):30442-51 and Hutchins M U, et al. J Cell Sci. 1999 November; 112 (Pt 22):4079-87).

Alternatively to or in combination with methods described above a eukaryotic cell containing peroxisomes that are capable to fuse with a membrane-structure of the cell involved in the secretory pathway of the cell may be obtained by classical strain improvement, using an appropriate screening method. A preferred screening method uses expression of a model polypeptide like GFP in the peroxisome of the cell, preferably using a signal promoting peroxisomal localisation of the model protein and measuring the presence of the model polypeptide outside the cell, as described later on. The presence of GFP outside the cell can be determined by, but is not limited to: fluorescence and/or western blotting.

The eukaryotic cell of the present invention may be genetically modified to obtain a phenotype displaying lower protease expression and/or secretion compared to the wild-type cell. Such phenotype may be obtained by deletion and/or modification and/or inactivation of a transcriptional regulator of expression of proteases. Such a transcriptional regulator is e.g. prtT. A technique to lower expression of proteases by modulating prtT is described in US2004/0191864A1

The choice of a host cell to be modified according to the present invention will to a large extent depend upon the source of the nucleic acid sequence encoding a polypeptide of interest or upon the identity of the metabolite to be produced. Preferably, the eukaryotic cell is a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, i.e. a yeast cell, such as *K. lactis* or *S. cerevisiae* or *Hansenula polymorpha* or *Pichia pastoris*, or a filamentous fungal cell. According to a most preferred embodiment, the eukaryotic cell is a filamentous fungal cell.

"Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicil-*

*lium, Piromyces, Schizophyllum, Talaromyces, Thermoascus, Thielavia, Tolypocladium*, and *Trichoderma*.

Preferred filamentous fungal cells belong to a species of an *Aspergillus, Penicillium* or *Trichoderma* genus, and most preferably a species of *Aspergillus niger, Aspergillus sojae, Aspergillus fumigatus, Aspergillus oryzae, Trichoderma reesei* or *Penicillium chrysogenum*.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL) *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006 and derivatives thereof.

Polypeptides

In a second aspect, the present invention relates to novel polypeptides to be used for preparation of the eukaryotic cells of the first aspect. In particular, the present invention provides fusing-polypeptides, chimeric polypeptides wherein a fusing-polypeptide is operatively associated with a peroxisomal membrane polypeptide, peroxisomal membrane polypeptides and complementing fusing-polypeptides, as defined herein above.

In one embodiment, the present invention provides a polypeptide displaying a v-SNARE function selected from the group consisting of (a) a polypeptide having an amino acid sequence according to SEQ ID NO: 13; (b) a polypeptide having an amino acid sequence that displays a degree of identity of at least 85%, preferably at least 90%, more preferably at least 93%, even more preferably at least 95% even more preferably at least 97%, even more preferably at least 98%, even more preferably at least 99% to the amino acid sequence according to SEQ ID NO: 13; and (c) a functional fragment of the polypeptide defined in (a) or (b).

In another embodiment, the present invention provides a peroxisomal membrane polypeptide selected from the group consisting of (a) a polypeptide having an amino acid sequence according to SEQ ID NO: 16; (b) a polypeptide having an amino acid sequence that displays a degree of identity of at least 85%, preferably at least 90%, more preferably at least 93%, even more preferably at least 95% even more preferably at least 97%, even more preferably at least 98%, even more preferably at least 99% to the amino acid sequence according to SEQ ID NO: 16; and (c) a functional fragment of the polypeptide defined in (a) or (b).

In yet another embodiment, the present invention provides a chimeric polypeptide suitable to obtain exposure at the surface of a peroxisome of an amino acid sequence corresponding to the amino acid sequence of a fusing-polypeptide exposed at the surface of a donor membrane-structure, wherein the chimeric polypeptide comprises a fusing-polypeptide or part thereof operatively associated with a peroxisomal membrane polypeptide or a part thereof.

Preferably, the fusing-polypeptide component of the chimeric polypeptide comprises the amino acids of a v-SNARE polypeptide from its N-terminus to the first (most N-terminal) transmembrane domain. More preferably the fusing polypeptide component comprises an amino acid sequence selected from the group consisting of (a) a sequence corresponding to position 1 to 95 of SEQ ID NO:13 and (b) a homologous sequence displaying a degree of identity of at least 50%, preferably at least 60%, more preferably at least 70%, even more preferably at least 80%, most preferably at least 90% to the sequence defined in (a).

Also preferably, the peroxisomal membrane protein component of the chimeric polypeptide comprises an amino acid sequence selected from the group consisting of (a) a sequence corresponding to position 2 to 224 of SEQ ID NO:16, preferably corresponding to a position 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 to position 224 and (b) a homologous sequence displaying a degree of identity of at least 50% preferably at least 60%, more preferably at least 70%, even more preferably at least 80%, most preferably at least 90% to the sequence defined in (a).

More preferably, the chimeric polypeptide has an amino acid sequence according to SEQ ID NO: 24.

Thus a preferred chimeric polypeptide of the invention comprises: (a) a domain of a fusing polypeptide that is exposed at the cytosolic surface of a donor membrane of the secretory pathway; and, (b) a domain that is targeted to and associated with the peroxisomal membrane; wherein domains (a) and (b) are operatively associated and wherein expression of the chimeric polypeptide in a host cell comprising peroxisomes, confers to the peroxisomes the ability to fuse with an acceptor membrane of the secretory pathway of the host cell. Preferably domains (a) and (b) are present in a single open reading frame and wherein domain (a) is closer to the N-terminus of the polypeptide than domain (b). Preferably domain (a) is from a v-SNARE. More preferably, domain (a) comprises a fragment from a v-SNARE spanning from the N-terminus up to or including the first transmembrane domain of the v-SNARE. In a preferred chimeric polypeptide according to the invention the fragment in domain (a) comprises a sequence corresponding to position 1 to 95 of SEQ ID NO:13 or a homologous sequence displaying a degree of identity of at least 50%, preferably at least 60%, more preferably at least 70%, even more preferably at least 80%, most preferably at least 90% to SEQ ID NO:13. The fragment may span at least 70%, 80%, 90%, or 95% of the amino acids from the N-terminus up to the first transmembrane domain of the v-SNARE.

In a preferred chimeric polypeptide according to the invention, domain (b) comprises a transmembrane domain and a sequence that targets the domain to the peroxisomal membrane. Preferably, the N-terminus of a transmembrane domain that is most proximal to domain (a) is oriented towards the cytosol. Preferably domain (b) comprises sequences from a peroxisomal membrane protein. More preferably domain (b) is from a peroxisomal membrane polypeptide the N-terminus of which is naturally exposed to the cytosolic side of the peroxisome, or from a peroxisomal membrane polypeptide that has at least one transmembrane domain having its N-terminus oriented towards to cytosol. Most preferably, domain (b) is from a peroxisomal membrane polypeptide N-terminal amino acids have been removed up to at least 10 amino acids from the most N-terminal transmembrane domain having its N-terminus oriented towards to cytosol. Domain (b) may be taken from a peroxisomal membrane polypeptide selected from Pmp22, Pmp34, Pmp47, Pmp70, Pex3, Pex11, Pex14, and Pex22. In a preferred embodiment the chimeric protein according to the invention domain (b) is a sequence corresponding to position 2 to 224 of SEQ ID NO:16, preferably corresponding to a position 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 to position 224 or a homologous sequence displaying a degree of identity of at least 50% preferably at least 60%, more preferably at least 70%, even more preferably at least 80%, most preferably at least 90% to SEQ ID NO:16. Most preferably, the chimeric protein has an amino acid sequence according to SEQ ID NO: 24.

For the purpose of the present invention, the degree of identity between two amino acid sequences refers to the percentage of amino acids that are identical between the two sequences. First, homologous polypeptide sequences are searched using the Basic Local Alignment Search Tool (BLAST) algorithm, which is described in Altschul, et al., J. Mol. Biol. 215: 403-410 (1990). Software for performing BLAST analyses is publicly available through the National Center for Biotechnology Information. The BLAST algorithm parameters W, B, and E determine the sensitivity and speed of the alignment. The BLAST program uses as defaults a word length (W) of 3, the BLOSUM62 scoring matrix (see Henikoff & Henikoff, Proc. Natl. Acad. Sci. USA 89: 10915 (1989)) alignments (B) of 50, expectation (E) of 10, M=5, N=4.

Next, the degree of identity (as defined above) of homologous sequences is determined using the CLUSTALW alignment algorithm (Higgins D. et al (1994). Nucleic Acids Res. 22:4673-4680) using the following parameters; Gap size: 5, Gap open: 11, Gap extension: 1, Mismatch: −15, Word size: 3.
Polynucleotides In a third aspect, the present invention relates to polynucleotides comprising nucleic acid sequences encoding any of the polypeptides of the second aspect.

The invention encompasses nucleic acid sequences encoding fusing-polypeptides, chimeric polypeptides wherein a fusing-polypeptide is operatively associated with a peroxisomal membrane polypeptide, peroxisomal membrane polypeptides and complementing fusing-polypeptides, as defined herein.

After having chosen a eukaryotic cell to be modified according to the invention, the identity (source) of the fusing-polypeptide, the polypeptide functioning as the peroxisomal membrane anchor and, optionally, the complementing fusing-polypeptide may be established. For instance, the source of nucleic acid sequences encoding the polypeptides of the second aspect may depend on the identity of the eukaryotic cell of choice. Preferably, the nucleic acid sequences encoding the polypeptides of the second aspect are endogenous to the eukaryotic cell to be modified according to the invention.

The present invention further provides a nucleic acid construct comprising a nucleic acid sequence encoding a polypeptide as defined above, operatively associated with one or more control sequences directing the expression of the polypeptide in a suitable host.

Expression will be understood to include any step involved in the production of the polypeptide including, but not limited to, transcription, post-transcriptional modification, translation, post-translational modification.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette or vector when the nucleic acid construct contains all the control sequences required for expression of a coding sequence.

The term "control sequences" is defined herein to include all components, which are necessary or advantageous for the expression of a polypeptide in general. Each control sequence may be native or foreign to the nucleic acid sequence encoding the polypeptide. Such control sequences include, but are not limited to, a promoter, a leader, optimal translation initiation sequences (as described in Kozak, 1991, J. Biol. Chem. 266:19867-19870), a polyadenylation sequence, a transcription terminator. At a minimum, the control sequences include a promoter, and transcriptional and translational stop signals.

The term "operatively associated" is defined herein as a configuration in which a control sequence is appropriately placed at a position relative to the coding sequence of the DNA sequence such that the control sequence directs the expression of a polypeptide.

The control sequence may be any appropriate promoter sequence, which shows transcriptional activity in the cell, including mutant, truncated, and hybrid promoters, and may be obtained from genes encoding extra-cellular or intracellular polypeptides either homologous (native) or heterologous (foreign) to the cell.

The promoter may be the promoter natively associated with the coding sequence to be expressed. The promoter may also be a constitutive or inducible promoter foreign to the coding sequence to be expressed. Examples of suitable promoters for use in mammalian cells are e.g. described in Sambrook and Russell (2001) "Molecular Cloning: A Laboratory Manual (3$^{rd}$ edition), Cold Spring Harbor Laboratory, Cold Spring Harbor Laboratory Press, New York. Examples of suitable promoters for use in yeasts include e.g. glycolytic promoters.

Examples of preferred inducible promoters that can be used are a starch-, copper-, oleic acid-inducible promoters.

According to another preferred embodiment, if a gene has to be over-expressed in the host cell of the invention, such as CAPP, a strong inducible promoter is used such as the glucoamylase promoter of *A. niger* or the TAKA amylase promoter of *A. oryzae*.

The control sequence may also be a suitable transcription terminator sequence, a sequence recognized by cell to terminate transcription. The terminator sequence is operably linked to the 3' terminus of the nucleic acid sequence encoding the polypeptide. Any terminator, which is functional in the cell, may be used in the present invention.

Preferred terminators for filamentous fungal cells are obtained from the genes encoding *A. oryzae* TAKA amylase, *A. niger* glucoamylase, *A. nidulans* anthranilate synthase, *A. niger* alpha-glucosidase, trpC gene and *Fusarium oxysporum* trypsin-like protease. The control sequence may also be a suitable leader sequence, a non-translated region of a mRNA which is important for translation by the filamentous fungal cell. The leader sequence is operably linked to the 5' terminus of the nucleic acid sequence encoding the polypeptide. Any leader sequence, which is functional in the cell, may be used in the present invention.

Preferred leaders for filamentous fungal cells are obtained from the genes encoding *A. oryzae* TAKA amylase and *A. nidulans* triose phosphate isomerase and *A. niger* glucoamylase.

The control sequence may also be a polyadenylation sequence, a sequence which is operably linked to the 3' terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention.

Preferred polyadenylation sequences for filamentous fungal cells are obtained from the genes encoding *A. oryzae* TAKA amylase, *A. niger* glucoamylase, *A. nidulans* anthranilate synthase, *Fusarium oxyporum* trypsin-like protease and *A. niger* alpha-glucosidase.

The control sequence may also be a pro-peptide coding region, which codes for an amino acid sequence positioned at the amino terminus of a polypeptide. The resultant polypeptide is known as a pro-enzyme or pro-polypeptide (or a zymogen in some cases).

The nucleic acid construct may be identical to or cloned in a vector or expression vector.

The recombinant expression vector may be any vector (e.g., a plasmid or virus), which can be conveniently subjected to recombinant DNA procedures and can bring about the expression of the nucleic acid sequence encoding the fusing-polypeptide (or complementing fusing-polypeptide). The choice of the vector will typically depend on the compatibility of the vector with the eukaryotic cell into which the vector is to be introduced. The vectors may be linear or closed circular plasmids. The vector may be an autonomously replicating vector, i.e., a vector, which exists as an extrachromosomal entity, the replication of which is independent of chromosomal replication, e.g., a plasmid, an extrachromosomal element, a minichromosome, or an artificial chromosome. An autonomously maintained cloning vector, which may be used in filamentous fungal cells comprise the AMA1-sequence (see e.g. Aleksenko and Clutterbuck (1997), Fungal Genet. Biol. 21: 373-397).

Alternatively, the vector may be one which, when introduced into the cell, is integrated into the genome and replicated together with the chromosome (s) into which it has been integrated. The integrative vector may integrate at random or at a predetermined target locus in the chromosomes of the host cell.

In a preferred embodiment of the invention, the integrative vector comprises a DNA fragment, which is homologous to a DNA sequence in a predetermined target locus in the genome of the host cell for targeting the integration of the vector to this predetermined locus. In order to promote targeted integration, the vector is preferably linearized prior to transformation of the host cell. Linearization is preferably performed such that at least one but preferably either end of the cloning vector is flanked by sequences homologous to the target locus. The length of the homologous sequences flanking the target locus is depending on the identity of the host cell. For a fungus, the length is preferably at least 30 bp, preferably at least 50 bp, even preferably at least 0.1 kb, even preferably at least 0.2 kb, more preferably at least 0.5 kb, even more preferably at least 1 kb, most preferably at least 2 kb. Preferably, the DNA sequence in the vector, which is homologous to the target locus is derived from a highly expressed locus meaning that it is derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein (as described in EP 357 127). A number of preferred highly expressed fungal genes are given by way of example: the amylase, glucoamylase, alcohol dehydrogenase, xylanase, glyceraldehyde-phosphate dehydrogenase or cellobiohydrolase genes from *Aspergilli* or *Trichoderma*. Most preferred highly expressed genes for these purposes are a glucoamylase gene, preferably an *A. niger* glucoamylase gene, an *A. oryzae* TAKA-amylase gene, an *A. nidulans* gpdA gene or a *Trichoderma reesei* cellobiohydrolase gene. This type of expression vector is highly suited to over-express a given gene in the eukaryotic cell of the invention, such as CAPP or a wild type or constitutively active mutant of a fusing-polypeptide or a complementing fusing-polypeptide (sso1).

Alternatively, modification or inactivation of a gene may be performed by established anti-sense techniques using a nucleotide sequence complementary to the nucleic acid sequence of the gene. More specifically, expression of the gene by a filamentous fungal cell may be reduced or eliminated by introducing a nucleotide sequence complementary to the nucleic acid sequence, which may be transcribed in the cell and is capable of hybridizing to the mRNA produced in the cell. Under conditions allowing the complementary antisense nucleotide sequence to hybridize to the mRNA, the amount of protein translated is thus reduced or eliminated. An example of expressing an antisense-RNA is shown in Appl Environ Microbiol. 2000 February; 66(2):775-82. (Characterization of a foldase, protein disulfide isomerase A, in the protein secretory pathway of *Aspergillus niger*. Ngiam C, Jeenes D J, Punt P J, Van Den Hondel C A, Archer D B) or (Zrenner R, Willmitzer L, Sonnewald U. Analysis of the expression of potato uridinediphosphate-glucose pyrophosphorylase and its inhibition by antisense RNA. Planta. (1993);190(2):247-52).

Furthermore, modification, downregulation or inactivation of the gene may be obtained via the RNA interference (RNAi) technique (FEMS Microb. Lett. 237 (2004): 317-324). In this method identical sense and antisense parts of the nucleotide sequence, which expression is to be affected, are cloned behind each other with a nucleotide spacer in between, and inserted into an expression vector. After such a molecule is transcribed, formation of small (21-23) nucleotide fragments will lead to a targeted degradation of the mRNA, which is to be affected. The elimination of the specific mRNA can be to various extends. The RNA interference techniques described in WO2005/05672A1 and/or WO2005/026356A1 may be used for downregulation, modification or inactivation of the gene.

If a gene of the host has to be inactivated such as VSM1, it is preferably performed by designing an inactivation vector and targeting the vector at the locus of the gene to be inactivated according to the techniques described in EP 635 574.

More than one copy of a nucleic acid sequence encoding a fusing-(optionally complementing fusing) polypeptide may be inserted into the host cell to increase production of the gene product. This can be done, preferably by integrating into its genome copies of the DNA sequence, more preferably by targeting the integration of the DNA sequence at a highly expressed locus, preferably at a glucoamylase or amylase locus. Alternatively, this can be done by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent. To increase even more the number of copies of the DNA sequence to be over expressed the technique of gene conversion as described in WO98/46772 may be used. This type of expression vector is also highly suited to over-express a given gene in the host cell of the invention such as CAPP.

A selectable marker for use in a filamentous fungal cell may be selected from the group including, but not limited to, amdS (acetamidase), argB (ornithine carbamoyltransferase), bar (phosphino-thricinacetyltransferase), hygB (hygromycinphosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus* cell are the amdS (EP 635574B1, WO 97/06261) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selection marker gene is the *A. nidulans* amdS coding sequence fused to the *A. nidulans* gpdA promoter (as disclosed in EP635574B). AmdS genes from other filamentous fungus may also be used (WO 97/06261). The bleomycine gene from *Streptoalloteichus hindustanus* can also be used as described in: Cassettes of the *Streptoalloteichus hindustanus* ble gene for transformation of lower and higher eukaryotes to phleomycin resistance. Drocourt D, Calmels T, Reynes J P, Baron M, Tiraby G. Nucleic Acids Res. 1990 Jul. 11; 18(13):4009.

The procedures used to ligate the elements described above to construct the recombinant expression vectors of the present invention are well known to one skilled in the art (see, e.g., Sambrook et al., 1989, supra).

The vector system may be a single vector or two or more vectors, which together contain the total DNA to be introduced into the genome of the cell. The vectors preferably contain one or more selectable markers, which permit easy selection of transformed cells. A selectable marker is a gene the product of which provides for biocide or viral resistance, resistance to heavy metals, prototrophy to auxotrophs, and the like.

The introduction of an expression vector or a nucleic acid construct into a cell is done using commonly known techniques. It may involve a process consisting of protoplast formation, transformation of the protoplasts, and regeneration of the cell wall in a manner known per se. Suitable procedures for transformation of *Aspergillus* cells are described in EP 238 023 and Yelton et al., 1984, Proceedings of the National Academy of Sciences USA 81:1470-1474. A suitable method of transforming *Fusarium* species is described by Malardier et al., 1989, Gene 78: 147156 or in WO 96/00787. Other method can be applied such as a method using biolistic transformation as described in: Biolistic transformation of the obligate plant pathogenic fungus, *Erysiphe graminis* f. sp. *hordei*. Christiansen S K, Knudsen S, Giese H. Curr Genet. 1995 December; 29(1):100-2. Selected transformed cells are then analysed for the capacity of peroxisomes to fuse with a membrane-structure involved in the secretory pathway of the cell, e.g the plasma membrane.

Several methods are available to analyse whether cells have obtained the capacity of fusion of the peroxisome with a membrane-structure of the cell involved in the secretory pathway of the cell.

According to one embodiment, the morphology of the cells is studied under electronic or fluorescence microscopy, using peroxisomal-specific labelling to visualize the fusion of the peroxisome with a membrane-structure of the cell involved in the secretory pathway of the cell. Examples of peroxisomal-specific labelling are:

thiolase labelling as described by: Simon M, Binder M, Adam G, Hartig A, Ruis H Control of peroxisome proliferation in *Saccharomyces cerevisiae* by ADR1, SNF1 (CAT1, CCR1) and SNF4 (CAT3). Yeast. 1992 April; 8(4):303-9, or GFP labelling as described by Monosov E Z, Wenzel T J, Luers G H, Heyman J A, Subramani S Labeling of peroxisomes with green fluorescent protein in living *P. pastoris* cells. J Histochem Cytochem. 1996 June; 44(6): 581-9, or catalase labelling as described by Kunce C M, Trelease R N, Turley R B. Purification and biosynthesis of cottonseed (*Gossypium hirsutum* L.) catalase. Biochem J. 1988 Apr. 1; 251(1): 147-55.

According to another embodiment, the fusion of the peroxisome with a membrane-structure of the cell involved in the secretory pathway of the cell is monitored by expressing a model polypeptide in the peroxisome of the cell, preferably using a signal promoting peroxisome localisation of the model polypeptide and measuring the presence of the model polypeptide in the culture medium. A preferred model polypeptide is Green Fluorescent Protein (GFP), since its presence in the fermentation medium can be visualised by fluorescence and monitored by western blotting. Other model polypeptides may be enzymatically active intracellular proteins operatively associated with a peroxisomal localization signal, like acetamidase, or naturally peroxisomal localised proteins like catalase, amadoriase or thiolase.

Preferably, the eukaryotic cell of the first aspect displays a peroxisomal fusion efficiency to an extent that at least 10% of the total amount of produced polypeptide is secreted into the culture medium at a given time point during culture, more preferably at least 40% of the produced polypeptide is secreted, even more preferably at least 60% of the produced polypeptide is secreted, even more preferably at least 70% of the produced polypeptide is secreted, even more preferably at least 80% of the produced polypeptide is secreted, and most preferably at least 90% of the produced polypeptide is secreted. The total amount of produced polypeptide is defined as the amount of polypeptide present in the culture medium, where the culture medium is defined to consist of a biomass fraction and a medium fraction. The amount of secreted polypeptide may be estimated using a model polypeptide. This model polypeptide may be Green Fluorescent Protein (GFP) with an engineered signal promoting peroxisomal localisation such as PTS-1 (e.g. GFP-SKL), as defined later on. The concentration of GFP-SKL within the culture medium fractions can be determined using techniques known the person skilled in the art (e.g. fluorescence measurement, absorbance measurement, Western blot). Using the determined concentrations of the model polypeptide, the fraction of secreted model polypeptide can be calculated as percentage of the total amount of produced model polypeptide.

Production of a Compound of Interest

The present invention further relates to a method for production of a compound of interest in the eukaryotic cell of the first aspect, wherein said compound is present in the peroxisome of the cell. The method comprises the following steps:

(a) culturing the eukaryotic cell of the first aspect in a given culture medium under conditions conducive to the expression of the compound of interest and, (b) optionally purifying the compound of interest.

According to a preferred embodiment, the compound of interest is recovered from the culture medium and optionally purified.

According to another preferred embodiment the compound of interest is a polypeptide.

More preferably, the eukaryotic cell of the first aspect additionally comprises a nucleic acid construct or an expression vector comprising a nucleic acid sequence encoding a polypeptide of interest and operatively associated therewith a nucleic acid sequence encoding a signal that promotes peroxisomal localisation of the polypeptide of interest.

The signal promoting peroxisomal localisation can be any signal as long as it allows the localisation and/or accumulation of the associated polypeptide inside the peroxisome.

Preferably, the signal promoting peroxisomal localisation is selected from the group consisting of:

(a) a tripeptide wherein the first amino acid in the N- to C-terminal direction is A, C, H, K, N, P, S or T, the second amino acid in the N- to C-terminal direction is H, K, N, Q, R or S and the third amino acid in the N- to C-terminal direction is A, F, I, L, M or V, and (b) a peptide defined as follows: (R/K) (L/V/I/Q) XX (L/V/I/H/Q) (L/S/G/A/K) X(H/Q)(L/A/F), wherein X may be any amino acid.

More preferably, the tripeptide defined in (a), also named PTS-1, is present as a C-terminal extension of the polypeptide to be produced in the peroxisome. Thus, the DNA sequence coding for the signal promoting peroxisomal localisation is cloned downstream of and in operative association with the DNA sequence encoding the polypeptide of interest.

According to a preferred embodiment, the tripeptide defined in (a) is a variant of [PAS]-[HKR]-[L] as described in: In silico prediction of the peroxisomal proteome in fungi, plants and animals. Olof Emanuelsson, Arne Elofsson, Gunnar von Heijne and Susana Cristóbal. J. Mol. Biol. (2003) 330, 443-456. According to a more preferred embodiment, the tripeptide defined in (a) is SKL or PRL.

According to another preferred embodiment, the tripeptide PTS-1) defined in (a) is preceded by a sequence that allows removal of the tripeptide sequence or that allows removal of the tripeptide sequence together with the sequence preceding the tripeptide sequence from the C-terminus of the polypeptide of interest once the polypeptide is secreted outside the cell. Such a sequence may e.g. be a recognition sequence of a suitable sequence specific protease or peptidase.

Peptides defined in (b) are also named PTS2 signals (Swinkels, B et al 1991. EMBO Journal 3255-3262; Petriv O. I. et al 2004. The Journal of molecular Biology 119-134). Preferably, they are present in the N-terminal part of the polypeptide.

If the polypeptide of interest already contains a signal promoting peroxisomal localisation, preferably this native signal is used to promote peroxisomal localisation. Alternatively, one may choose to replace the native signal promoting peroxisomal localisation by a different one. Alternatively, one may choose to replace the native DNA sequence promoting peroxisomal localisation by one of the DNA sequences encoding the sequence promoting peroxisomal localisation defined earlier on.

In one embodiment, the present invention envisages a phased extra-cellular production of the polypeptide of interest present in the peroxisome. In a first phase, the polypeptide of interest accumulates in the peroxisome and in a second phase, the inducible promoter driving the expression of the chimeric-polypeptide of the invention (optionally complementing fusing-polypeptide) is induced by adding a specific inducer to the medium, which will in turn lead to the fusion of the peroxisome with an acceptor membrane-structure of the cell involved in the secretory pathway of the cell. This will result in the extra-cellular production of the polypeptide of interest.

Alternatively, other types of phased production are possible: first, the production of the polypeptide of interest, then induction of peroxisome proliferation and as a last step, induction of the fusion of the peroxisome with an acceptor membrane-structure of the cell involved in the secretory pathway of the cell.

The polypeptide may be any polypeptide native or foreign to the host cell. The term "foreign polypeptide" is defined herein as a polypeptide, which is not naturally produced by a given cell. The term "polypeptide" is not meant herein to refer to a specific length of the encoded polypeptide produced and therefore encompasses peptides, oligopeptides and proteins.

The eukaryotic cell of the first aspect is highly suited for the production of polypeptides needing a reducing environment for maturation, e.g. intracellular polypeptides. Therefore, according to a preferred embodiment, the polypeptide of interest is an intracellular polypeptide. Accordingly, the method of the invention using the eukaryotic cell of the first aspect is the first one able to produce intracellular polypeptide in the culture medium on an industrial scale.

A preferred polypeptide is an enzyme naturally produced in the peroxisome, such as amadoriase, catalase, acyl-CoA oxidase, linoleate isomerase, trans-2-enoyl-ACP reductase, trichothecene 3-O-acetyltransferase, alcohol dehydrogenase, carnitine racemase, D-mandelate dehydrogenase, enoyl CoA hydratase, fructosyl amine oxygen oxidoreductase, 2-hydroxyhepta-2,4-diene-1,7-dioate isomerase, NADP-dependent malate dehydrogenase, oxidoreductase, quinone reductase All these enzymes contain a C-terminal SKL sequence.

Other intracellular enzymes are ceramidases, epoxide hydrolases aminopeptidases, acylases, aldolase, hydroxylase, aminopeptidases.

In another embodiment, the polypeptide is an antibody or portion thereof, an antigen, a clotting factor, an extracellular enzyme, a hormone or a hormone variant, a receptor or portions thereof, a regulatory protein, a structural protein, a reporter, or a transport protein.

According to another preferred embodiment, the polypeptide to be produced is recombinant: the eukaryotic cell of the first aspect has been transformed with a nucleic acid construct or an expression construct comprising a DNA sequence promoting peroxisomal localisation and operatively associated therewith a DNA sequence encoding the polypeptide to be produced.

The present invention thereby advantageously allows the extracellular production of polypeptides that encounter difficulties in the normal secretory pathway of the cell. As an example, the polypeptide of interest produced is an extracellular polypeptide and may not contain more than 20 cysteines, not more than 10 cysteines, not more than 6 cysteines or not more than 2 cysteines. Such polypeptide may be native or heterologous to the host cell. These polypeptides are preferably recombinant for the host cell. Examples of such polypeptides are the following: oxalate decarboxylase from *Aspergillus phoenicis*, containing no cysteines (APOXD, described in patent application WO 9842827-A2); aspergillopepsin II from *Aspergillus niger*, containing no cysteines (The gene and deduced protein sequences of the zymogen of *Aspergillus niger* acid proteinase A, Inoue et al., J Biol Chem. 1991 Oct. 15; 266(29):19484-19489); secreted acid phosphatase 2 from *Leishmania mexicana*, containing no cysteines (Ser/Thr-rich repetitive motifs as targets for phosphoglycan modifications in *Leishmania mexicana* secreted acid phosphatase, Wiese et al., EMBO J. 1995 Mar. 15; 14(6):1067-1074); non aspartyl acid protease from *Sclerotinia sclerotiorum*, containing no cysteines (Regulation of acp1, encoding a non-aspartyl acid protease expressed during pathogenesis of *Sclerotinia sclerotiorum*, Poussereau et al., Microbiology. 2001 March; 147 (Pt 3):717-726); xylanase A from *Aspergillus niger*, containing 1 cysteine (xynA described in patent application WO 200068396-A2); sulphamidase from *Mus musculus*, containing 2 cysteines (Gene encoding the mouse sulphamidase: cDNA cloning, structure, and chromosomal mapping, Costanzi et al., Mamm Genome. 2000 June; 11(6):436-439). The polypeptide of interest may further be an aminopeptidase, amylase, carbohydrase, carboxypeptidase, catalase, cellulase, chitinase, cutinase, deoxyribonuclease, dextranase, esterase, alpha-galactosidase, beta-galactosidase, glucoamylase, alpha-glucosidase, beta-glucosidase, haloperoxidase, hydrolase, invertase, isomerase, laccase, ligase, lipase, lipoxygenase, lyase, mannosidase, mutanase, oxidase, oxygenase, oxidoreductase pectinase, peroxidase, phospholipase, phytase, polyphenoloxidase, protease, ribonuclease, transferase, transglutaminase, or xylanase. The nucleic acid sequence encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The method of the invention advantageously allows the production of at least 0.01 g/l of the polypeptide of interest at the end of the culture process. Preferably at least 0.05 g/l of the polypeptide is produced, more preferably at least 0.1 g/l, even more preferably at least 0.5 g/l and most preferably at least 1 g/l.

According to another preferred embodiment the compound of interest is a metabolite. Preferred metabolites are: taxol, isoprenoids including carotenoids, penicillins, cephalosporins including alkaloids, statins including lovastatin and antioxidants. According to a first preferred embodiment, the host cell of the first aspect is being used to produce an endogenous peroxisomal metabolite. Examples of endogenous peroxisomal metabolites are isobutyric acid, isovaleric acid and a-methyl butyric acid. According to a second preferred embodiment, the metabolite is produced using the eukaryotic cell of the first aspect as host cell, wherein the eukaryotic cell additionally comprises a nucleic acid construct or an expression vector comprising a nucleic acid sequence encoding an enzyme involved in the metabolite synthesis and operatively associated therewith a nucleic acid sequence encoding a signal that promotes peroxisomal localisation of the enzyme involved in the metabolite synthesis. The signal promoting peroxisomal localisation can be any signal as long as it allows the localisation and/or accumulation of the associated polypeptide inside the peroxisome as already described earlier. Examples of enzymes involved in a metabolite synthesis are the following:

Carotenoid synthesis: Phytoene-beta carotene synthase crtYB and crtE, crtI, crtY, crtB and crtZ.

Taxol biosynthesis: taxane 13 alpha-hydroxylase and taxadiene synthase.

Penicilline synthesis: acyltransferase.

Cephalosporins synthesis: expandase.

Alkaloids synthesis: S)-Norcoclaurine synthase (NCS).

Statins polyketide synthase: Geraniol 10-hydroxylase.

According to yet another embodiment, the present invention envisages a phased extra-cellular production of the metabolite present in the peroxisome. In a first phase, the metabolite accumulates in the peroxisome and in a second phase, the inducible promoter driving the expression of the fusing-polypeptide (optionally complementing fusing-polypeptide) is induced by adding a specific inducer to the medium, which will in turn lead to the fusion of the peroxisome with an acceptor membrane-structure of the cell involved in the secretory pathway of the cell. This will result in the extra-cellular production of the metabolite.

Alternatively, other types of phased production are possible: first the production of the metabolite, then induction of peroxisome proliferation and as a last step induction of the fusion of the peroxisome with an acceptor membrane-structure of the cell involved in the secretory pathway of the cell.

Culture Conditions

The host cells of the first aspect are cultured in a nutrient medium suitable for production of the compound of interest using methods known in the art. For example, the cells may be cultured by shake flask culture, small-scale or large-scale culture (including continuous, batch, fed-batch, or solid state cultures) in laboratory or industrial fermentors performed in a suitable medium and under conditions allowing the compound of interest to be expressed and/or isolated. The culture takes place in a suitable nutrient medium comprising carbon and nitrogen sources and inorganic salts, using procedures known in the art (see, e.g., Bennett, J. W. and LaSure, L., eds., More Gene Manipulations in Fungi, Academic Press, CA, 1991). Suitable media are available from commercial suppliers or may be prepared using published compositions (e.g., in catalogues of the American Type Culture Collection).

The invention further provides an improved production process for the production of the compound of interest. According to a first preferred embodiment, the host cells of the first aspect are cultured in a medium wherein a suitable amount of oxygen is fed to the culture to maintain the culture under conditions of oxygen limitation. More preferably, the culture condition of oxygen limitation is performed in a medium wherein all nutrients are provided in excess over at least part of the culture period. Even more preferably, at least part of the culture period means half of the culture period, more preferably $\frac{2}{3}$ of the culture period, even more preferably $\frac{4}{5}$ of the culture period, even more preferably $\frac{5}{6}$ of the culture period and most preferably the whole culture period.

With the feature "provided in excess" is meant that all the nutrients are supplied in a sufficient amount to avoid the establishment of a limitation in the growth of the host cells of the present invention during culture. Obviously, the nutrients should not be supplied in such an amount as to cause inhibitory or toxic effects.

A suitable amount of oxygen is fed to the culture to maintain the culture under conditions of oxygen limitation. Therefore, in the context of this invention, a suitable amount of oxygen is defined as an amount of oxygen that effectuates a condition of oxygen limitation during culture. To maintain the medium under oxygen limitation, the amount of oxygen fed to the culture medium should not exceed the amount of oxygen that is consumed by the host cells. In other words, the OTR should be substantially identical to the OUR. The OTR (oxygen transfer rate) is defined as the rate with which the oxygen is transferred from the gas phase to the liquid phase of the culture medium. OTR is expressed as oxygen quantity per unit of time (e.g. moles/h). The OTR is conveniently determined from the difference between the amount of oxygen entering the culture equipment and the amount of oxygen measured in the gas outlet. The OUR (oxygen uptake rate) is defined as the rate with which the host cells consume oxygen fed to the culture medium. "Substantially identical" means that the OTR is identical to the OUR with a deviation of plus or minus 5%. Preferably, the OTR is as high as possible, i.e. as allowed by e.g. the culture equipment configuration and/or the oxygen concentration in the gas feed, provided that the host cells are able to immediately consume the oxygen. However, it will be clear to the skilled person that it is also possible to perform the culture process under oxygen limitation at an OTR that is lower than the maximum OTR that can be reached, for instance at 80 or 90% of the maximum OTR value.

In a situation that the OTR is substantially identical to the OUR, the dissolved oxygen concentration in the culture medium typically will be constant, and if oxygen limitation is controlling the culture, the dissolved oxygen will be zero or close to zero. A convenient way to determine whether oxygen limitation exists in the culture process is to test the effect on OTR of a slight decrease of the stirrer speed (e.g. 5%). If the OTR also decreases then an oxygen limitation exists indeed. If the OTR does not decrease and/or only the dissolved oxygen concentration decreases, oxygen limitation does not exist. An alternative way is to determine the effect of an increase in nutrients feed on OTR. If the increase in nutrients feed is not accompanied by an increase in OTR, oxygen limitation exists.

According to a second preferred embodiment, culturing of the host cells of the first aspect comprises alteration of the pH of the culture medium during the culture process to effectuate a phased extra-cellular production of the compound of interest. Culture of the host cells of the first aspect may typically be performed at any pH conducive for both host cells and compound of interest. Phased extra-cellular production may increase the overall yield of the process. In a first phase, at pH most conducive for the host cells of the first aspect, the compound of interest accumulates in the peroxisome. In the second phase, the pH of the culture medium is altered. More preferably, the pH is altered in a linear course during a transition phase between phases one and two of culture of the host cells of the first aspect. The total duration of the culture process of the host cells of the first aspect is defined by the equation Tc=a+t+b, wherein:
Tc=the total time of the culture process in hours,
a=the duration of the first phase of culture in hours,
t=the duration of the transition phase in hours,
b=the duration of the second phase of culture in hours.

According to a yet more preferred embodiment, the equation fulfils the following criteria:

$97 \leq Tc=a+t+b \leq 240$ wherein:

$72 \leq a \leq 120$, $1 \leq t \leq 24$, $24 \leq b \leq 96$

Even more preferably, the equation fulfils the following criteria:

$128 \leq Tc=a+t+b \leq 216$ wherein:

$72 \leq a \leq 96$, $8 \leq t \leq 24$, $48 \leq b \leq 96$

Yet even more preferably, the equation fulfils the following criteria:

$160 \leq Tc=a+t+b \leq 216$ wherein $72 \leq a \leq 96$, $16 \leq t \leq 24$, $72 \leq b \leq 96$ Most preferably, the equation fulfils the following criteria:

$Tc=a+t+b \leq 192$ wherein:

$a \leq 72$, $t \leq 24$, $b \leq 96$

Preferably, the host cell is cultured in the first phase at a pH ranged between 4.5 and 6.0 and in the second phase at a pH ranged between 5.5 and 7.0. Most preferably, the host cell is cultured in the first phase (a) at pH 6.0 and in the second phase (b) at pH 6.7.

According to a third preferred embodiment, culture of the host cells of the first aspect comprises alteration of the temperature of the culture medium during the culture process to effectuate a phased extra-cellular production of compound of interest. Culture of the host cells of the first aspect may typically be performed at any temperature conducive for both host cells and compound of interest. Phased extra-cellular production may increase the overall yield of the process. In a first phase, at temperature most conducive for the host cells of the first aspect, the compound of interest accumulates in the peroxisome. In the second phase, the temperature of the culture medium is altered. Preferably, the host cell is cultured in the first phase at a temperature ranged between 30° C. and 37° and in the second phase at a temperature ranged between 34° C. and 38° C. Most preferably, the host cell is cultured in the first phase at 30° C. and in the second phase at 36° C.

Alternatively and according to an even more preferred embodiment, culture of the host cells of the first aspect is performed:
wherein a suitable amount of oxygen is fed to the culture to maintain the culture under conditions of oxygen limitation during at least part of the culture process, and/or
wherein the pH of the culture medium is altered during the culture process to effectuate a phased extra-cellular production of compound of interest and/or
wherein the temperature of the culture medium is altered during the culture process to effectuate a phased extra-cellular production of compound of interest and/or
wherein the host cell of the first aspect is an *Aspergillus* species, most preferably a strain of *Aspergillus niger*.

Most preferably, culture of the host cells of the first aspect is performed:
wherein a suitable amount of oxygen is fed to the culture to maintain the culture under conditions of oxygen limitation during at least part of the culture process, and/or
wherein the pH of the culture medium is altered during the culture process to effectuate a phased extra-cellular production of compound of interest wherein the equation of total culture time as described above fulfils the following criteria: Tc=a+t+b≦168 wherein: a≦72, t≦24, b≦96 and wherein the pH of the first phase is 6.0 and the pH of the second phase is 6.7 and/or
wherein the temperature of the culture medium is altered during the culture process to effectuate a phased extra-cellular production of compound of interest and wherein the temperature of the first phase is 30° C. and the temperature of the second phase is 36° C. and/or
wherein the host cell of the first aspect is an *Aspergillus* species, most preferably a strain of *Aspergillus niger*.

The cultivation medium may be adapted to the compound of interest to be produced and to the eukaryotic cell chosen.

According to a preferred embodiment, the culture medium comprises an activator of Ceramide Activated Phosphatase Protein (CAPP). This phosphatase is known to activate SNARE interactions by dephosphorylating t-SNARE's. (Marash M, Gerst J E: t-SNARE dephosphorylation promotes SNARE assembly and exocytosis in yeast. EMBO J. 2001 Feb. 1; 20(3):411-21). An example of an activator of CAPP is a ceramide, e.g. dihydro-$C_2$ ceramide or another C2-ceramide (Calbiochem, SIGMA). Preferably, 1 to 100 µM ceramide is present in the culture medium at the beginning of the culture. More preferably, 5 to 50 µM ceramide is present in the culture medium at the beginning of the culture. Even more preferably, about 10 μM ceramide is present in the culture medium at the beginning of the culture. According to a most preferred embodiment, the concentration of ceramide is monitored during the whole culture process to be kept at such values. If needed, fresh ceramide may be continuously added during the culture process.

According to another preferred embodiment, the culture medium comprises a substance inducing peroxisome proliferation, such as a substrate that is metabolised via at least one enzyme that is normally located in the peroxisome, preferably a fatty acid, more preferably oleate, as previously described (Yasuyoshi Sakai et al, Regulation of Peroxisomal Proteins and Organelle Proliferation by Multiple Carbon Sources in the Methylotrophic Yeast, *Candida boidinii*. Yeast 14, 1175-1187 (1998)). Fatty acids can also be used to obtain peroxisomal proliferation as previously described (Intrasuksri U, et al, Mechanisms of peroxisome proliferation by perfluorooctanoic acid and endogenous fatty acids. Gen Pharmacol. 1998 August; 31 (2):187-97). The amount of substance inducing peroxisome proliferation is defined as the percentage of the carbon that is available in the medium (e.g. the carbon source of the culture medium is comprised of 10% peroxisome proliferation inducing substance+90% glucose). Preferably, the amount of substance inducing peroxisome proliferation is ranged between 0.1% and 100% of the carbon source of the culture medium. More preferably, the amount of substance inducing peroxisome proliferation is ranged between 1% and 50% of the carbon source of the culture medium. Even more preferably, the amount of substance inducing peroxisome proliferation is ranged between 2% and 40% of the carbon source of the culture medium. Even more preferably, the amount of substance inducing peroxisome proliferation is ranged between 3% and 30% of the carbon source of the culture medium. Even more preferably, the amount of substance inducing peroxisome proliferation is ranged between 4% and 25% of the carbon source of the culture medium. Even more preferably, the amount of substance inducing peroxisome proliferation is ranged between 5% and 20% of the carbon source of the culture medium. Even more preferably, the amount of substance inducing peroxisome proliferation is ranged between 6% and 18% of the carbon source of the culture medium. Even more preferably, the amount of substance inducing peroxisome proliferation is ranged between 7% and 15% of the carbon source of the culture medium. Even more preferably, the amount of substance inducing peroxisome proliferation is ranged between 8% and 13% of the carbon source of the culture medium. Even more preferably, the amount of substance inducing peroxisome proliferation is ranged between 9% and 12% of the carbon source of the culture medium. Most preferably, the amount of substance inducing peroxisome proliferation is equal to 10% of the carbon source of the culture medium. According to a most preferred embodiment, the substance inducing peroxisome proliferation is Na-oleate and/or oleic acid and the amount of Na-oleate and/or oleic acid present in the culture medium is equal to 10% of the carbon source of the culture medium.

According to a more preferred embodiment, the culture medium comprises both an activator of CAPP and a peroxisome-inducing substance, both in preferred amounts as described in previous paragraphs.

The resulting compound of interest may be isolated from the culture medium by methods known in the art. For example, the compound of interest may be isolated from the culture medium by conventional procedures including, but not limited to, centrifugation, filtration, extraction, spray drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), or extraction (see, e.g., Protein Purification, J.-C. Janson and Lars Ryden, editors, VCH Publishers, New York, 1989).

Accumulation of the Compound of Interest in the Peroxisome

In a further aspect, the invention, provides a method for production and optionally isolation of a polypeptide of interest in a host cell, preferably a filamentous fungal cell, wherein the host cell comprises a nucleic acid construct or an expression construct, said construct comprises a DNA sequence promoting peroxisomal localisation and operatively associated therewith a DNA sequence encoding the polypeptide to be produced. In another aspect, the invention provides a method for production and optionally isolation of a metabolite in a host cell, preferably a filamentous fungal cell, wherein the host cell comprises a nucleic acid construct or an expression construct, said construct comprises a DNA sequence promoting peroxisomal localisation and operatively associated therewith a DNA sequence encoding an enzyme involved in the metabolite synthesis. All these elements have been defined earlier. In these last two aspects, the homeostasis of the peroxisomes of said host cells is preferably affected as defined before. In these last two aspects, the culture medium preferably comprises a peroxisome-inducing substance as defined before. In these last two aspects, the compound of interest may subsequently be recovered from the peroxisomes of the cell lysates. Recovery of the compound of interest is preferably performed as already described (Visualization and purification of yeast peroxisomes. Erdmann R, Gould S J. Methods Enzymol. 2002; 351:365-81). In these last two aspects, the culture conditions (Oxygen-limitation and/or pH value of the culture medium and/or temperature of the culture medium) of said host cells are preferably as defined earlier in the description.

The present invention is further described by the following examples, which should not be construed as limiting the scope of the invention.

Example 1

Example 1

Targeting an Acetamidase (amdS) Protein in Peroxisome in *Aspergillus niger* and *Kluyveromyces lactis* Using a C-Terminal SKL Tag The *Aspergillus niger* strain (CBS 513.88) and *K. lactis* strain (CBS 685.97) used were already deposited. In these strains, using classical molecular biology techniques, as described in Molecular Cloning: A Laboratory Manual, Sambrook et al., New York: Cold Spring Harbour Press, 1989, several genes were over-expressed and activity of the encoded proteins was determined as described below.

1.1. Cloning the *A. niger* Acetamidase Gene with and without SKL Tag and Expression in *A. Niger* and *K. lactis*

Genomic DNA from CBS 513.88 was used as template in a PCR reaction using SEQ ID NO: 1 and SEQ ID NO: 2, resulting in coding sequence shown as SEQ ID NO: 4. In addition, genomic DNA from CBS 513.88 was used as template in a PCR reaction using SEQ ID NO: 1 and SEQ ID NO:

3, resulting in coding sequence shown as SEQ ID NO: 5. All PCR reactions, cDNA synthesis, ligations and transformations were performed as described above in Molecular Cloning. The resulting PCR fragments (SEQ ID NO: 4 and SEQ ID NO: 5) were cut with PacI and AscI according to the manufacturers instructions and individually ligated in a PacI, AscI linearized *A. niger* expression vector depicted in FIG. 1, resulting in two constructs in which each acetamidase gene (with and without—SKL) was placed under control of the glaA promoter. The expression vectors were used to transform *A. niger*.

Figure 2:
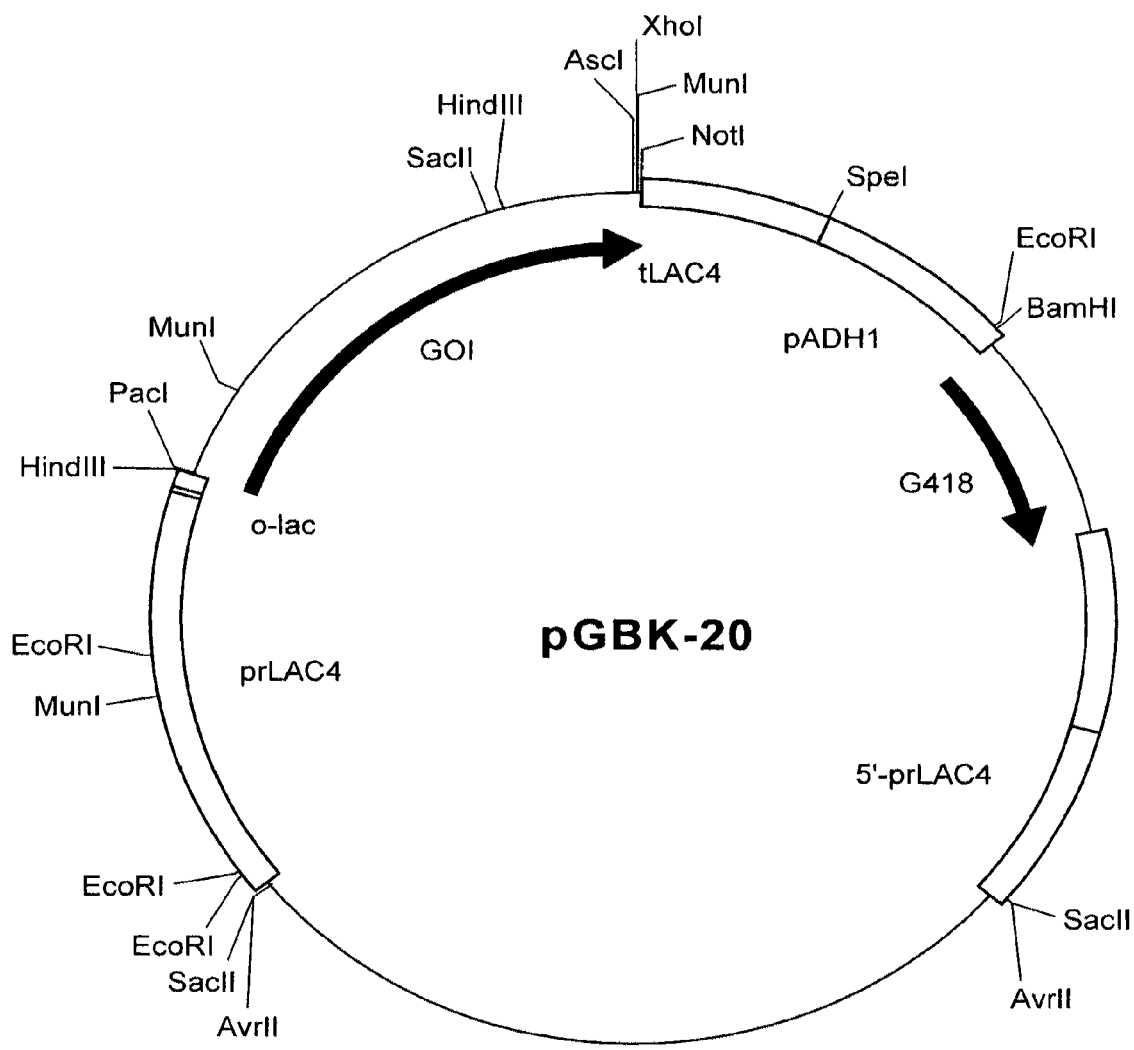
FIG. 2 depicts the *K. lactis* expression vector pGBK-20.

In addition, genomic DNA from CBS 513.88 was used as template in a PCR reaction using SEQ ID NO: 6 and SEQ ID NO: 7, resulting in coding sequence shown as SEQ ID NO: 9. Furthermore, genomic DNA from CBS 513.88 was used as template in a PCR reaction using SEQ ID NO: 6 and SEQ ID NO: 8, resulting in coding sequence shown as SEQ ID NO: 10. The resulting PCR fragments (SEQ ID NO: 9 and SEQ ID NO: 10) were cut with PacI and AscI according to the manufacturers instructions and individually ligated in a PacI, AscI linearized *K. lactis* expression vector depicted in FIG. 2, resulting in two construct in which each *A. niger* acetamidase gene (with and without—SKL; SEQ ID NO: 9 and SEQ ID NO: 10, respectively) was placed under control of the lac4 promotor. The expression vectors were used to transform *K. lactis*.

The resulting plasmids were transformed respectively to *A. niger* CBS 513.88 or to *K. lactis* CBS 685.97. The transformation of *A. niger* was performed according to (Kelly J M, Hynes M J Transformation of *Aspergillus niger* by the amdS gene of *Aspergillus nidulans*. EMBO J. 1985 February; 4(2): 475-9) and of *K. lactis* according to (Sreekrishna K, Webster T D, Dickson R C, Transformation of *Kluyveromyces lactis* with the kanamycin (G418) resistance gene of Tn903. Gene. 1984 April; 28(1):73-81).

Figure 3:
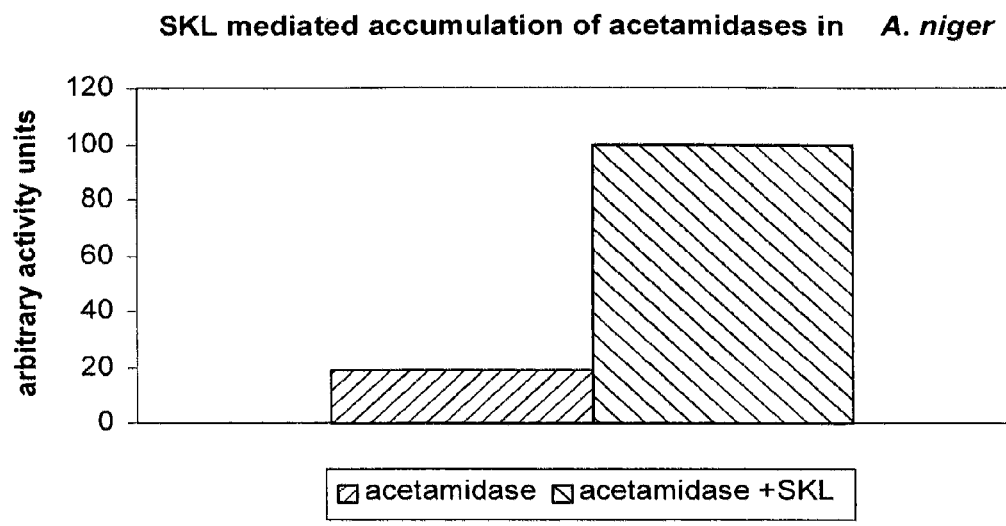
FIG. 3 depicts the acetamidase activity measured in control *A. niger* cells transformed with the acetamidase gene or in *A. niger* cells transformed with the acetamidase gene fused to the SKL sequence.

1.2. Cultivation of the *A. niger* and *K. lactis* Transformants and Determination of the Intracellular Acetamidase Activity The presence of the expression cassette in the *A. niger* transformants was checked by PCR. The selected transformants were cultivated for 5 days at 30° C. at 250 rpm in 500 ml conical shake flasks with baffles in 100 ml of the following medium: 150 g/l maltose, 60 g/l bacto soytone, 1 g/l NaH$_2$PO$_4$, 15 g/l (NH$_4$)$_2$SO$_4$, 1 g/l MgSO$_4$.4H$_2$O, 0.08 g/l tween-80, 0.02 g/l Basildon, 20 g/l Morpholino Ethane Sulfonicacid (MES), 1 g/l L-arginine. Cells were harvested and disrupted by grinding under liquid nitrogen. Cell lysates were obtained by resuspending 25 mg grinded biomass in 0.5 ml phosphate buffered D$_2$O (Deuterium H$_2$O, Cambridge Isotope Laboratories, deuterium pD 7.0). Subsequently 0.5 ml of 10 mg/ml substrate (propionamide) in D$_2$O was added and incubated at 37° C. for 4 days and centrifuged (end concentration 5 mg/mL substrate and 25 mg/mL extract). Measurement of the acetamidase activity in the control cell CBS513.88 and in the transformed cell was performed by Nuclear Magnetic Resonance as described by the manufacturer's instructions (FIG. 3). $^1$H NMR spectra were recorded on a Bruker DRX-600 operating at a proton frequency of 600 MHz at a probe temperature of 300 K. A 5 mm triple resonance probe with self-shielded gradients was used. $^1$H NMR spectra of all reference compounds were acquired in order to show that all the compounds involved have unique NMR signals, based on which they can be identified and quantified (not shown). In order to create perfect reference spectra of every relevant compound, a stock solution of each compound was prepared in D$_2$O Stock solutions were prepared in concentrations of 10 mg/mL by weighting the substrate or the reference compound and adding D$_2$O. From these stock solutions 500 µL was mixed with 500 µL 0.5 M phosphate buffer pH 6.96 (KH$_2$PO$_4$/K$_2$HPO$_4$). $^1$H-NMR spectra of each compound, i.e. acrylamide, acrylic acid, acetamide, acetic acid, propionamide and propionic acid were subsequently collected at 600 MHz in D$_2$O at 27° C. (endconcentration 5 mg/mL substrate or reference compound in D$_2$O). Unique chemical shifts, which did not overlap with signals caused by other compounds, were identified for each compound. In addition, the purity of each reference was checked and the absence of possible contaminants was confirmed.

The compounds had the following characteristic signals:

Acrylamide (catalog number 8.00830, lot 4202056, Merck N.J. USA): 5.82 (dd, Hb, J=10.3 Hz, 1.2 Hz), 6.22 (dd, Hc, J=17.2 Hz, 1.2 Hz), 6.28 (d, Ha, J=10.3 Hz), 6.31 (d, Ha, J=10.3 Hz) ppm.

Acrylic acid (catalog number 14,723-0, lot S17163-034, Aldrich, Wis. USA): 5.65 (dd, Hb, J=10.4 Hz, 1.6 Hz), 6.01 (dd, Hc, J=17.4 Hz, 1.6 Hz), 6.11 (d, CH2=CH, 3J=10.3 Hz), 6.14 (d, CH2=CH, 3J=10.3 Hz).

Acetamide (catalog number 12,263-7, lot16813BA-453, Aldrich, Wis. USA): 1.99 (s, CH3) ppm.

Acetic acid (catalog number 1.00063, lot K31668363, Merck N.J. USA): 1.90 (s, CH3) ppm.

Propionamide (catalog number 14,393-6, lot 25009JB-413, Aldrich, Wis. USA): 1.10 (t, CH3), 2.27 (q, CH2) ppm.

Propionic acid (catalog number P-1386, lot 083 K3404, Sigma, St Louis, Mo. USA): 1.09 (t, CH3), 2.37 (q, CH2) ppm.

The resulting *K. lactis* transformants (checked by PCR) were cultivated for 3 days in 100 ml YEPD (Yeast Extract 10 g/l, Peptone 20 g/l, Dextrose 20 g/l) at 30° C. at 250 rpm in 500 ml conical shake flasks with baffles. Cells were harvested and disrupted by grinding under liquid nitrogen. Cell lysates were obtained by resuspending grinded biomass in 20 mM sodiumphosphatebuffer, pH 7.4, 1 mM EDTA, 2 mM DTT with protease inhibitor (complete from Roche: catalogus number 1873580). Acetamidase activities were determined in the control *K. lactis* cell and in the transformed cell according to Skouloubris et al., Molecular Microbiology (2001) 40(3), 596-609 (FIG. 4).

Figure 4:
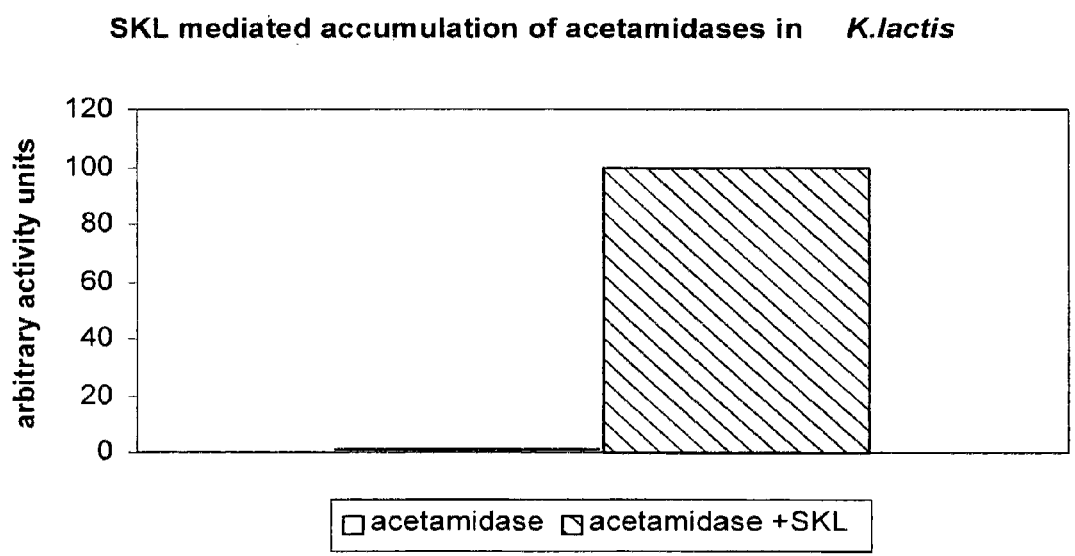
FIG. 4 depicts the acetamidase activity measured in control *K. lactis* cells transformed with the acetamidase gene or in *K. lactis* cells transformed with the acetamidase gene fused to the SKL sequence.

As clearly shown in FIGS. 3 and 4, the addition of the C-terminal SKL tag, which promotes peroxisomal localisation of the acetamidase protein, increases the intracellular acetamidase enzyme activity in *A. niger* and *K. lactis*.

Example 2

Addition of Oleate to the Fermentation Medium to Increase Peroxisome Proliferation An increase of the number of peroxisomes per cell and thus an increase in peroxisomal storage volume of *A. niger* was mediated by supplementing the culture medium with Na-oleate (catalogus number 26125, Riedel-de Haën, Hannover, Germany) and Tween-40 (catalogus number 93775, Fluka, Buchs, Switzerland). The increased number of peroxisomes was demonstrated by fluorescence microscopy using Green Fluorescent Protein (GFP) (Chalfie, M et al., Science (1994) 263(5148): 802-805) with an engineered C-terminal SKL tag. The C-terminal—SKL tag was engineered to the widely used and well-characterised GFP gene using PCR methodology as described in Example 1. The resulting GFP-SKL gene was cloned into an *A. niger* expression vector and transformed to *A. niger* CBS513.88 using methodology as described in Example 1.

The resulting *A. niger* strains over-expressing GFP with a C-terminal linked—SKL peptide were cultivated in shake flasks using an orbital shaker at 30° C., 250 RPM in Minimal Enriched *Aspergillus* Medium (MEAM, described in patent application WO 98/46772). After 48 hours of pre-culture, mycelium was harvested and, washed and subsequently transferred to fresh culture medium (MEAM) supplemented with 0.18% (w/v) Na-oleate and 0.02% (w/v) Tween-40). Control cultures were cultured in MEAM without supplementation with Na-oleate and Tween-40. After 26 hours of culture, samples were analysed using a Zeiss fluorescence microscope, using blue light excitation (490 nm). Representative samples were used for fluorescence photography using Fujicolor 800ASA colorfilm.

Figure 5:
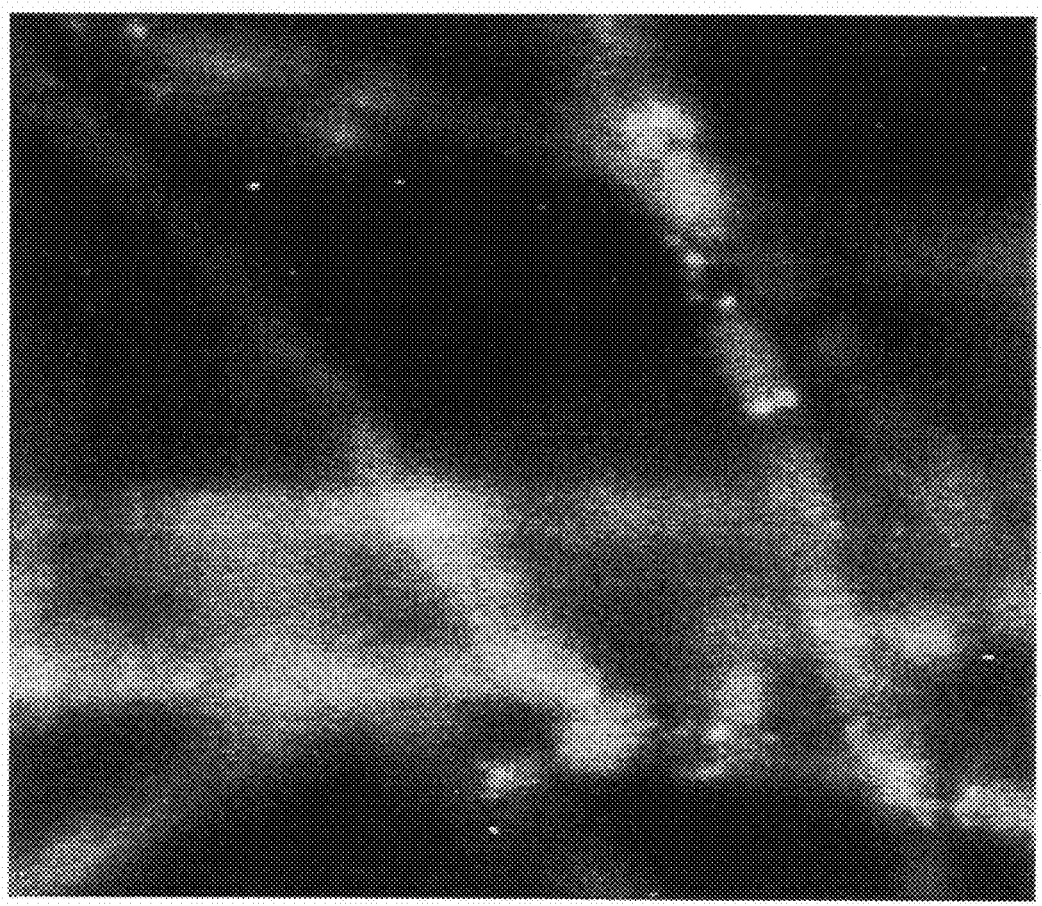
FIG. 5 shows the peroxisomes of *A. niger* transformed with GFP-SKL.
Figure 6:
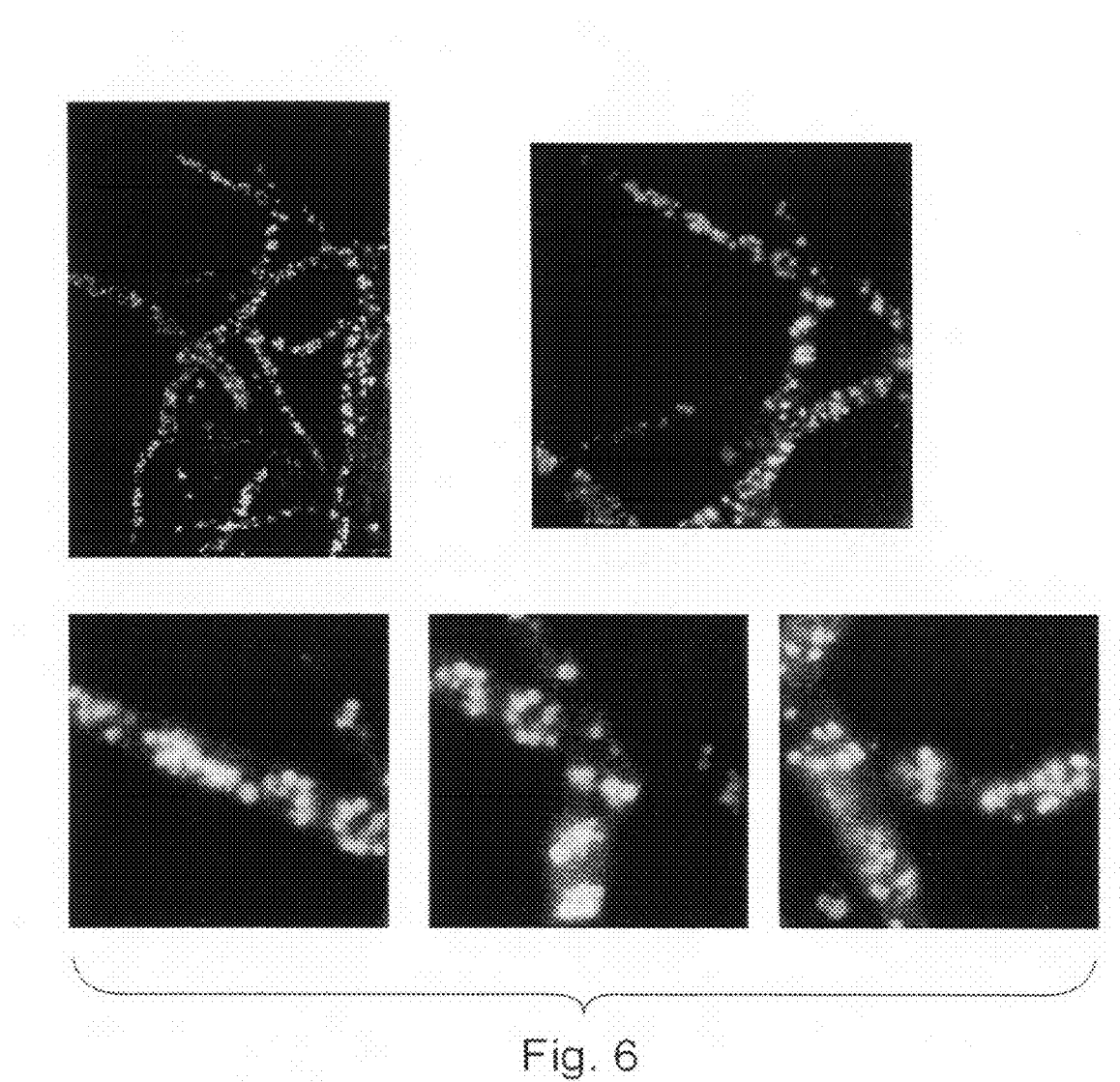
FIG. 6 shows the peroxisomes of *A. niger* transformed with GFP-SKL and cultured with Na-oleate, a mediator of peroxisome proliferation.

As can be observed in FIG. 5, cultivation of a GFP-SKL over-expressing strain, in a medium, which does not comprise Na-oleate and Tween-40, resulted in few peroxisomes per cell. As clearly demonstrated in FIG. 6, cultivating the same cell in a fermentation medium supplemented with Na-oleate and Tween-40, induced peroxisome proliferation and resulted in increased numbers of peroxisomes per cell.

Example 3

Release of the Peroxisomal Content (GFP-SKL) Outside the Cell by Fusion of the Peroxisome with the Plasma Membrane 3.1 Cloning and Expression of a Fusing Polypeptide at the Surface of a Peroxisome

*A. niger* v-SNARE SncA, shown as SEQ ID NO's: 11, 12 and 13, genomic, cDNA and protein sequence, respectively, without transmembrane domain, was fused to peroxisomal membrane protein 22 (Pmp22), shown as SEQ ID NO's: 14, 15 and 16, genomic, cDNA and protein sequence, respectively. Genomic DNA from CBS513.88 was used as template in a PCR reaction using SEQ ID NO: 17 and SEQ ID NO: 18 to result in coding SEQ ID NO: 19. In addition, genomic DNA from CBS513.88 was used as template in a PCR reaction using SEQ ID NO: 20 and SEQ ID NO: 21 to result in coding SEQ ID NO: 22. Subsequently, SEQ ID NO: 19 and SEQ ID NO: 22 and were used as template in a PCR reaction using SEQ ID NO: 17 and SEQ ID NO: 21 to result in SEQ ID NO: 23. The resulting PCR fragment (SEQ ID NO: 23) was digested with restriction enzymes PacI and AscI according to the manufacturers instructions and ligated into a PacI, AscI linearised *A. niger* expression vector as depicted in FIG. 1. This resulted in a construct in which the gene encoding the fusing polypeptide with peroxisomal membrane anchor (SncA/Pmp-22) was placed under control of the glaA promoter. Expression of the gene resulted in a chimeric protein comprising a peroxisomal membrane anchor, as shown as SEQ ID NO: 24. The SncA/Pmp-22 expression vector together with a GFP-SKL expression vector was used to co-transform *A. niger*. All PCR reactions, ligations and transformations were performed using classical molecular biology techniques, as described in Molecular Cloning: A Laboratory Manual, Sambrook et al., New York: Cold Spring Harbor Press, 1989.

3.2 Cultivation of the Co-Transformants for Analysis of Release of Peroxisomal Content Amongst several clones of *A. niger* strains over-expressing GFP-SKL and SncA/Pmp-22 as obtained in the former paragraph, a selection was made using PCR for clones containing a single copy of each gene. The clone selected was cultivated in shake flasks in an orbital shaker at 30° C., 250 RPM in MEAM buffered medium (described extensively in patent application WO 98/46772) with and without 10 μM C2-ceramide (N-Acetyl-D-sphingosine: catalogues number A7191, Sigma, St. Louis Mo. USA). A GFP-SKL over-expressing strain containing a single gene copy (construction described in Example 2) and an empty host strain (CBS513.88) were used as controls. Samples were taken at 24 and 48-hour time points. The supernatant samples were cleared by centrifugation and separated from residual cell debris by ultrafiltration through 0.45 μm filters (catalogus number 4614, Pall, Ann Arbor, Mo. USA).

3.3 SDS-PAGE Analysis of the Release of Peroxisomal Content Outside the Cell; Analysis of C2-Ceramide as a Release-Promoting Agent Supernatant samples from 3.2 were analysed by SDS-PAGE. SDS-PAGE was performed using NuPAGE Novex high performance pre-cast gels (4-12% Bis-Tris gradient gel, Invitrogen, Paisley, UK) according to manufacturer's instructions. The samples (20 μl) were mixed with 2.0 μl reducing agent and 6.0 μl sample buffer according to the manufacturer's instructions and subsequently heated for 10 min at 70° C. before loading onto the gel. After electrophoresis, gels were stained using Simply Blue Safe stain (Invitrogen, Paisley, UK) according to manufacturer's instructions.

Figure 7:
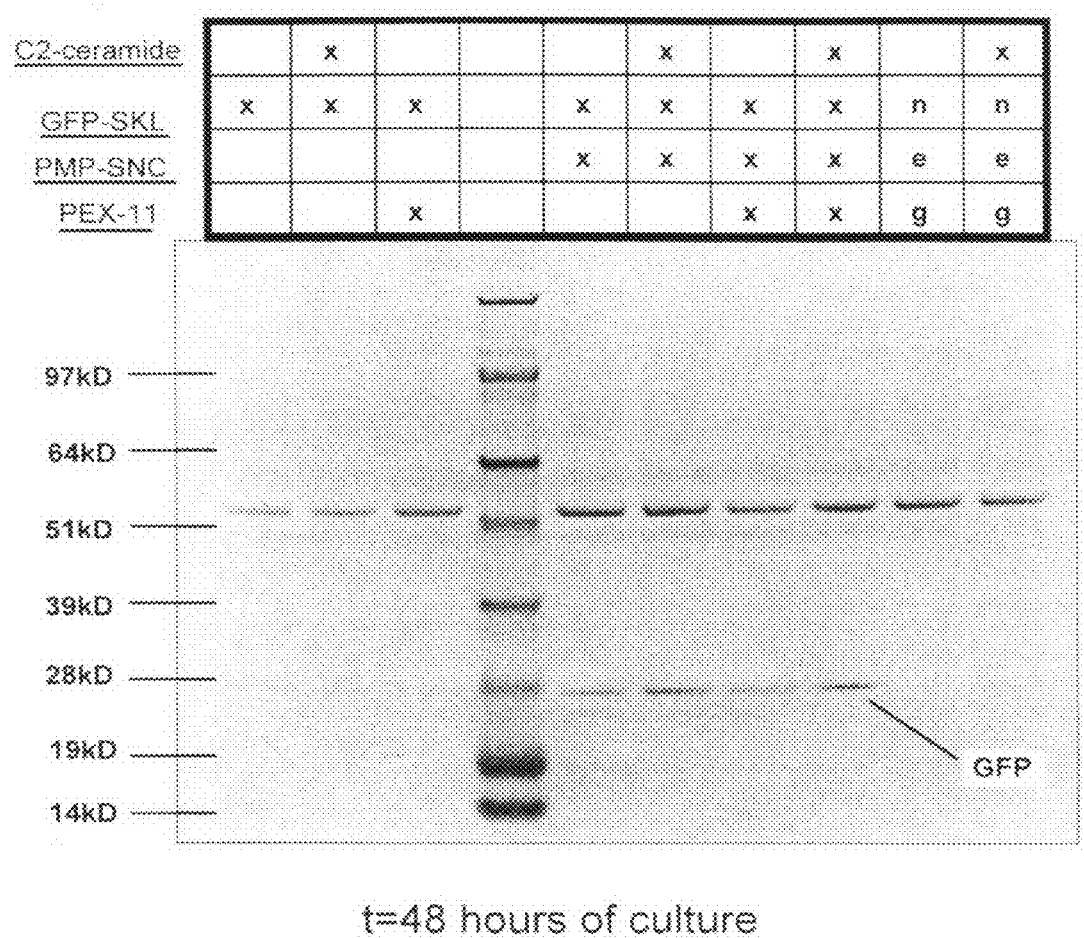
FIG. 7 shows a SDS-PAGE gel containing culture supernatants of several transformed *A. niger* strains demonstrating the release of GFP-SKL in the supernatant.

In FIG. 7, the release of GFP-SKL outside the cell can be clearly observed. All samples contain equal amounts of endogenous protein as observed by the endogenous band at 54 kD. In contrast, lanes, 4, 5, 6 and 7 contain significantly more GFP-SKL as compared to control lanes 1, 2 and 3. Furthermore, it is demonstrated that C2-ceramide further induces the release of peroxisomal content, i.e. GFP-SKL outside the cells; lanes 5 and 7 (MEAM+C2-ceramide) contain more GFP-SKL as compared to lanes 4 and 6, respectively.

3.4 Western Blot Analysis of the Release of Peroxisomal Content Outside the Cell; Analysis of C2-Ceramide as a Release-Promoting Agent Supernatant samples from 3.2 were analysed by Western blot. SDS-PAGE was carried out as in 3.3, Western blot was carried out using the XCell II Blot Module according to manufacturer's instructions (Invitrogen, Paisley, UK). After electrophoresis, the NuPage gel was blotted for 1 hour at 30 volt, on a pre-cut nitrocellulose membrane (Invitrogen). The blot was blocked at room temperature (rT) for 1 hour in Tris Buffered Saline (TBS, 20 mM Tris-HCl pH 7.4, 0.9% w/v NaCl; catalogues number: T5912, Sigma)+2% skim milk. The commercially available anti-GFP antibody (anti-GFP Eurogentec, Belgium catno: MMS-118P) was diluted to $1/10.000$ and the blot was incubated for 1 hour with this antibody. Subsequently the blot was washed 3 times for 5 minutes with MilliQ water and TBS+0.2% skim milk. After washing, the blot was incubated for one hour at room temperature with a $1/5000$ dilution of Goat Anti-Rabbit Peroxidase (catalogues number 31460, Pierce Rock Ford Ill. USA). The blot was washed again and immersed with detection fluid (ECL direct nucleic acid labelling and detection system, Amersham biosciences, Buckinghamshire, UK). Finally, the blot was exposed to AGFA Curix Blue HC-S plus film (AGFA Mortsel, Belgium).

Figure 8:
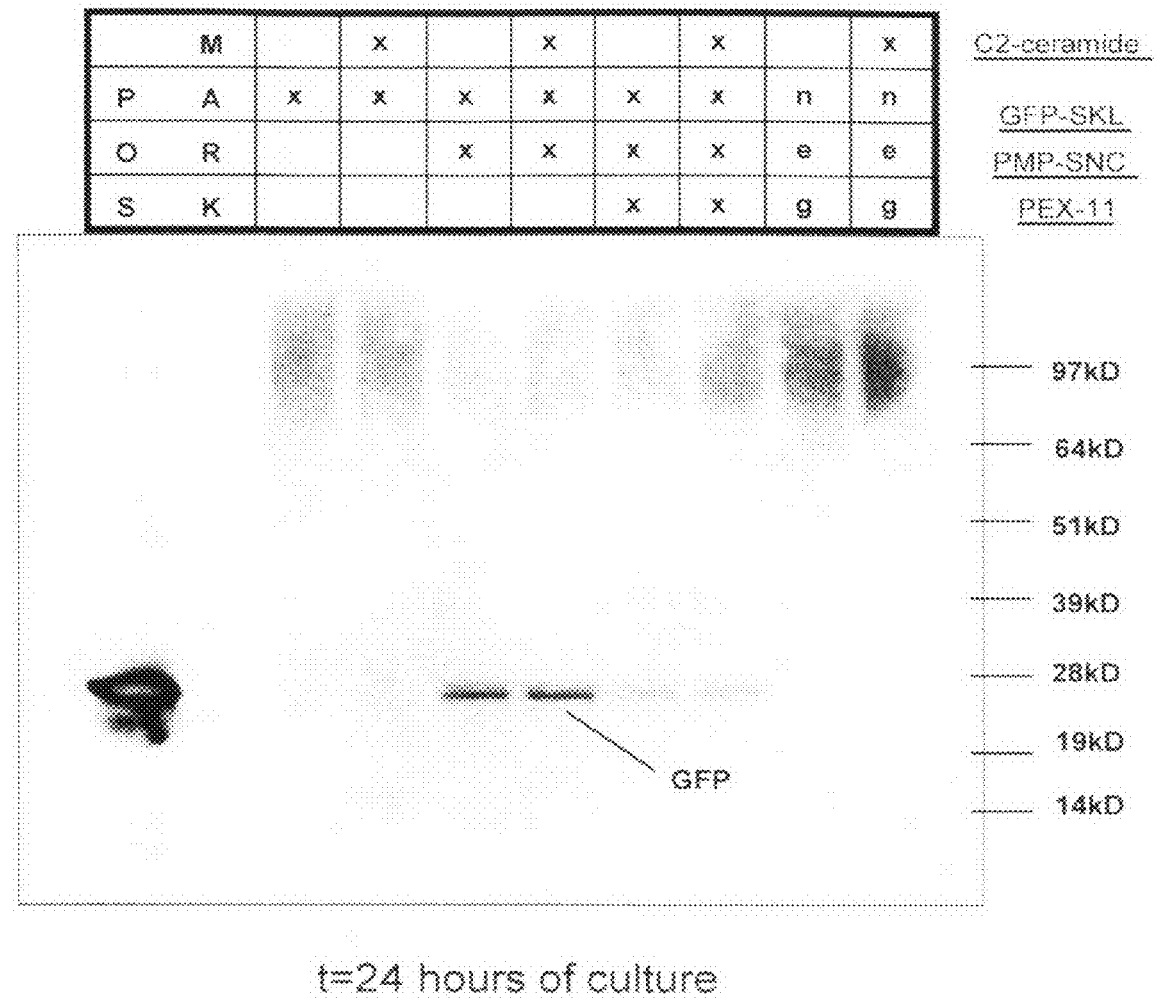
FIG. 8 shows a Western blot containing culture supernatants of several transformed *A. niger* strains demonstrating the release of GFP-SKL in the supernatant.

In FIG. 8, the release of GFP-SKL outside the cell can be clearly observed. In lanes 5, 6, 7 and 8, GFP-SKL is present. In contrast, in lanes 3, 4 and 9, 10, no extracellular GFP-SKL is present.

3.5 Analysis of A-Specific Lysis of *A. niger* Cultures

To demonstrate that the observed release of peroxisomal content as described in 3.1 to 3.4 was not mediated by aspecific lysis, the degree of lysis of the cultures was determined by measurement of the activity of the intra-cellular enzyme acetamidase (amdS) in the culture supernatant. Acetamidase measurement was performed according to Skouloubris et al., Molecular Microbiology (2001) 40 (3), 596-609. Ten µl of supernatant from cultures was added to 100 mM acetamide (catalogues number A0500, Sigma Mo. USA) in Phosphate EDTA Buffer (PEB, 100 mM Na-Phosphate, pH 7.4, 10 mM EDTA). After 90 minutes incubation at 37° C., 400 µl Phenolnitroprusside (catalogus number P6994, Sigma Mo. USA) and 400 µl alkaline hypochloride solution (0.2%, catalogue number A1727, Sigma Mo. USA) was added and mixed. The mix was incubated at 55° C. for 6 minutes. Subsequently, the absorption was measured at 635 nm in an Ultraspec 2000 UV/VIS Spectrophotometer (Pharmacia Biotech, Sweden) according to the manufacturer's instructions. The amount of amdS in the samples was calculated from a standard curve and designated as relative units/ml culture supernatant.

The results are depicted in FIG. 10 clearly observed that after 24 hours of cultivation, no amdS activity is present in the culture supernatants, demonstrating that no lyses has occurred. After 48 hours of cultivation, all samples contain equivalent amounts of amdS activity, demonstrating that the degree of lyses in all cultures is the same. These results clearly show that the observed presence of GFP-SKL in culture supernatants in 3.1 to 3.4 was mediated by active release of peroxisomal content outside the cells and not by a-specific lysis of cells.

Example 4

Pmp22 can be Utilised to Decorate Peroxisomes with Recombinant (Poly)Peptides

To demonstrate that Pmp22 can be utilised as a peroxisomal membrane anchor, a chimeric gene was constructed in which Green Fluorescent Protein (GFP) was fused to the N-terminal end of Pmp22 and expressed in *A. niger*. Fluorescence microscopy revealed intense green, spherical shaped, intra-cellular micro bodies.

4.1 Cloning and Expression of GFP/Pmp22 Chimeric Construct

GFP, shown as SEQ ID NO: 25 and 26 was fused to peroxisomal membrane protein 22 (Pmp22), shown as SEQ ID NO's: 14, 15 and 16.

GFP DNA (SEQ ID NO: 25) was used as template in a PCR reaction using SEQ ID NO: 27 and SEQ ID NO: 28 to result in SEQ ID NO: 29. In addition, genomic DNA from CBS513.88 was used as template in a PCR reaction using SEQ ID NO: 30 and SEQ ID NO: 31 to result in coding SEQ ID NO: 32. Subsequently, SEQ ID: 29 and SEQ ID: 32 were used as template in a PCR reaction using SEQ ID: 27 and SEQ ID: 31 to result in SEQ ID: 33. The resulting PCR fragment (SEQ ID NO: 33) was digested with restriction enzymes PacI and AscI according to the manufacturers instructions and ligated into a PacI, AscI linearised *A. niger* expression vector as depicted in FIG. 1. This resulted in a construct in which the gene encoding GFP with peroxisomal membrane anchor (GFP/Pmp-22) was placed under control of the glaA promoter. Expression of the gene resulted in GFP with peroxisomal membrane anchor shown as SEQ ID NO: 34. The GFP/Pmp-22 expression vector was used to transform *A. niger*. All PCR reactions, ligations and transformations were performed using classical molecular biology techniques, as described in Molecular Cloning: A Laboratory Manual, Sambrook et al., New York: Cold Spring Harbor Press, 1989.

The resulting *A. niger* strains over-expressing GFP/Pmp-22 were cultivated in shake flasks using an orbital shaker at 30° C., 250 RPM in Minimal Enriched *Aspergillus* Medium (MEAM, described in patent application WO 98/46772). Control cultures over-expressing GFP with and without a C-terminal linked—SKL (as described in example 2) were cultivated using identical culture conditions. After 18 hours of culture, samples were analysed using a Zeiss fluorescence microscope, using blue light excitation (490 nm). Representative samples were used for fluorescence photography using Fujicolor 800ASA colorfilm.

Figure 9A:
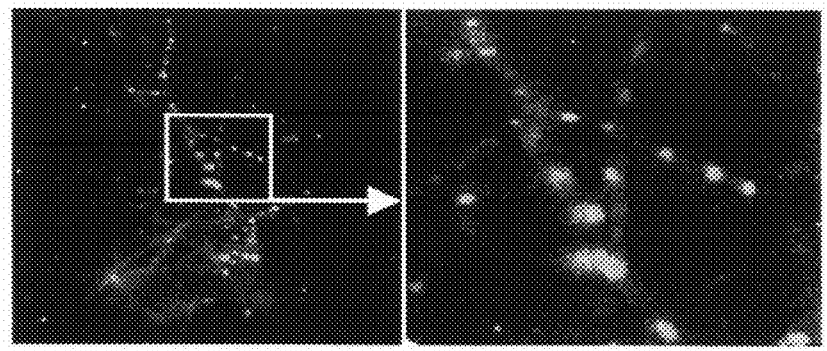
FIG. 9 shows *A. niger* strains expressing GFP (panel C), GFP-SKL (panel B) or GFP/Pmp22 (panel A).
Figure 9B:
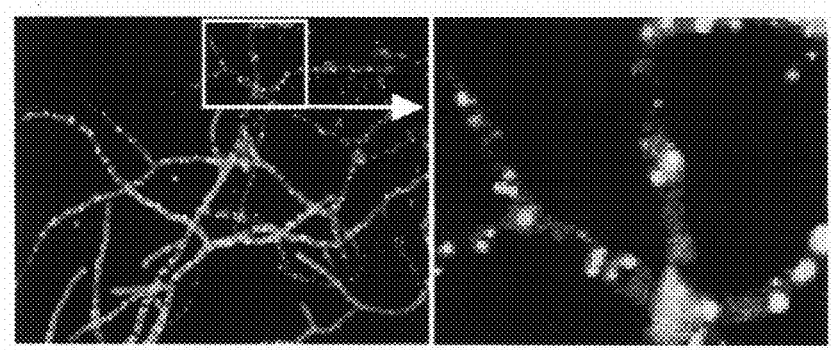
Figure 9C:
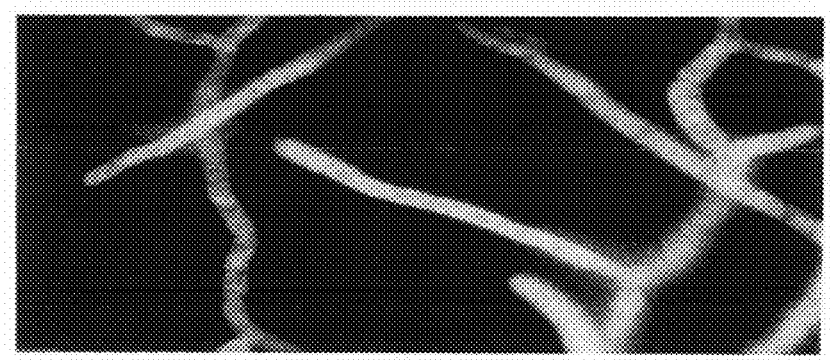

As can be observed in FIG. 9A, *A. niger* over-expressing GFP/Pmp22 chimeric protein shows the same punctuate pattern of intense green, spherical shaped, intra-cellular micro bodies as *A. niger* over-expressing GFP-SKL (FIG. 9B), where GFP-SKL is targeted to the peroxisome by the C-terminal SKL. In contrast, *A. niger* over-expressing wild-type GFP (i.e. without C-terminal SKL), shows general green fluorescence throughout the whole cytoplasm of the cells (FIG. 9C).

The combined results clearly demonstrate that Pmp-22 can be utilised as a peroxisomal membrane anchor to decorate peroxisomes with recombinant (poly)peptides like GFP or the fusing peptides described in this invention.

Example 5

Construction of an *A. niger* Host Cell Capable of Secreting Intracellular Compounds by Using Peroxisomes Decorated with Fusing-Polypeptides 5.1 Cloning and Expression of a Fusing Polypeptide at the Surface of a Peroxisome of an *A. niger* Host Cell

Figure 11:
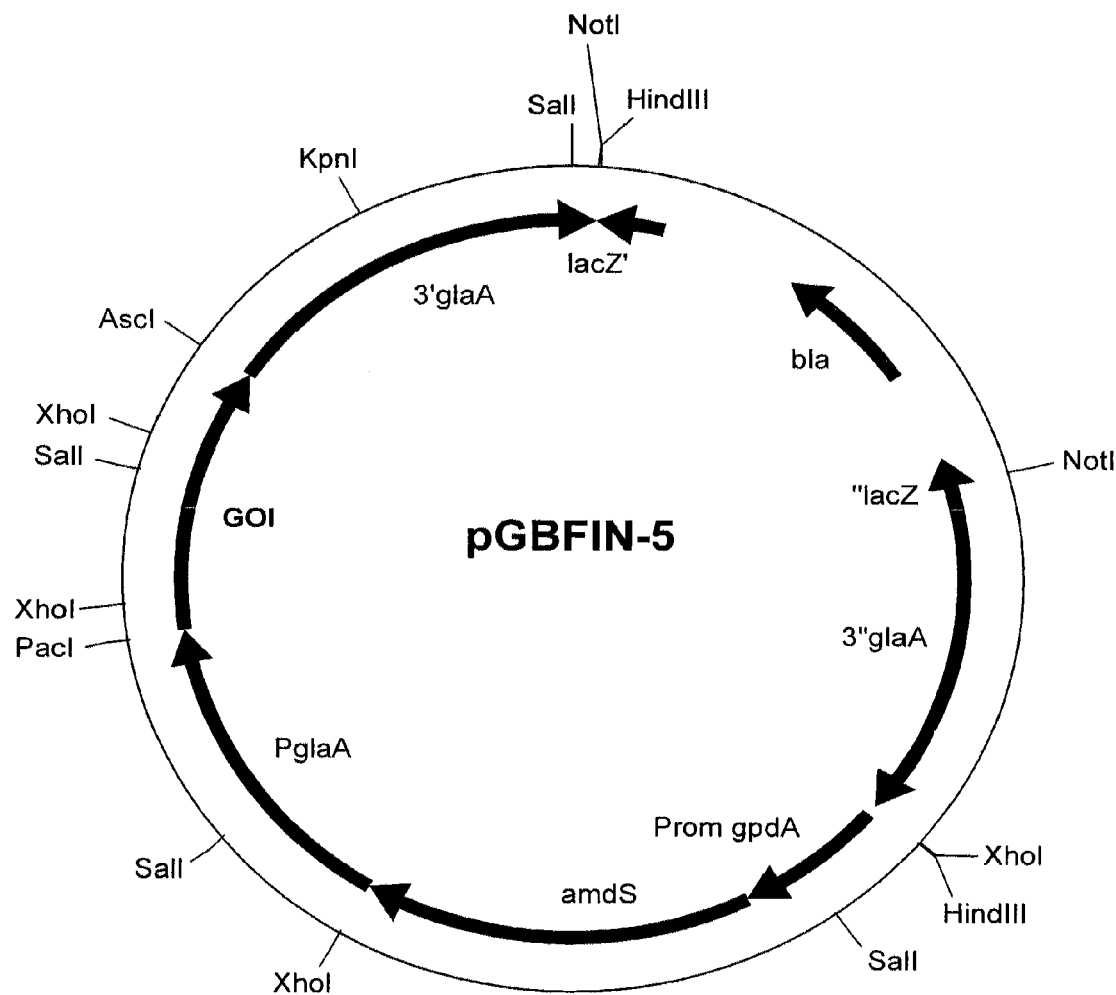
FIG. 11 depicts the *A. niger* expression vector pGBFIN-5.

*A. niger* v-SNARE SncA, shown as SEQ ID NO: 11, SEQ ID NO: 12 and SEQ ID NO: 13, genomic, cDNA and protein sequence, respectively, without transmembrane domain, was fused to peroxisomal membrane protein 22 (Pmp22), shown as SEQ ID NO: 14, SEQ ID NO:15 and SEQ ID NO: 16, genomic, cDNA and protein sequence, respectively. Genomic DNA from CBS513.88 was used as template in a PCR reaction using SEQ ID NO: 18 and SEQ ID NO: 35 to result in coding SEQ ID NO: 36. In addition, genomic DNA from CBS513.88 was used as template in a PCR reaction using SEQ ID NO: 20 and SEQ ID NO: 37 to result in coding SEQ ID NO: 38. Subsequently, SEQ ID NO: 36 and SEQ ID NO: 38 were used as template in a PCR reaction using SEQ ID NO: 35 and SEQ ID NO: 37 to result in SEQ ID NO: 39. The resulting PCR fragment (SEQ ID NO: 39) was digested with restriction enzymes PacI and AscI according to the manufacturers instructions and ligated into a PacI, AscI linearised *A. niger* expression vector as depicted in FIG. 11 (pGBFIN-5). This resulted in a construct in which the gene encoding the fusing polypeptide with peroxisomal membrane anchor (SncA/Pmp-22) was placed under control of the glaA promoter. Expression of the gene resulted in a chimeric protein comprising a peroxisomal membrane anchor, as shown as SEQ ID NO: 40 (SncA/Pmp22protein). The SncA/Pmp-22 expression vector was used to transform *A. niger* CBS513.88 over-expressing GFP-SKL, as described in example 2. The resulting *A. niger* transformants were analysed by PCR for presence of both expression constructs SncA/Pmp22 and GFP-SKL. Several clones containing both expression constructs were analysed for the release of the peroxisomal content by cultivation and SDS-PAGE as described in examples 3.2 and 3.3. The best performing clone was further analysed in examples 6 and 7. All PCR reactions, ligations and transformations were performed using classical molecular biology techniques, as described in Molecular Cloning: A Laboratory Manual, Sambrook et al., New York: Cold Spring Harbor Press, 1989.

5.2 Curing the *A. niger* Host Cell Capable of Secreting Intracellular Compounds The best performing clone obtained in the previous paragraph and further analysed in examples 6 and 7, was selected to be cured of GFP-SKL expression. The resulting *A. niger* host cell capable of secreting intracellular compounds was used as a generic *A. niger* host capable of secreting intracellular compounds in examples 8 and 9.

The clone selected was cultivated in shake flasks in an orbital shaker at 30° C., 250 RPM in MEAM buffered medium (described extensively in patent application WO 98/46772). Culture of this clone was plated out on plates containing PDA medium (Difco, France) in order to lose the GFP-SKL expression vector in spontaneous recombination event. A total of 100.000 colonies were analysed for expression of GFP-SKL using UV-illumination at 315 nm on a Geldoc 2000 system (Bio-Rad, Italy). Colonies demonstrating the least GFP expression were subjected to another round of culture and plating. After two rounds of selection, a clone with the least GFP-SKL expression was selected. PCR demonstrated that the strain still contained the SncA/Pmp22 expression vector, while retaining at least one copy of the GFP-SKL expression cassette. The resulting *A. niger* host cell capable of secreting intracellular compounds was used as a generic *A. niger* host capable of secreting intracellular compounds in examples 8 and 9.

Example 6

Extracellular GFP-SKL Production in 10-L Scale Fermentors

Strain:
Construction of the *A. niger* CBS513.88 strain over-expressing GFP-SKL and SncA/Pmp22 was described in example 5.1. Spores of the strain were stored at −80° C. ($5\times10^7$ viable spores/vial).
Inoculation Procedure:
The content of one spore-vial was added to the pre-culture medium in a baffled 2 L-shake flask (20 g/L yeast extract, 20 g/L glucose, pH 6.8 (with KOH), 300 mL medium, steam-sterilized 20 min at 121° C.). This pre-culture was cultured for 40 h at 30° C. and 220 rpm.
Fed-Batch Fermentation:
The culture was performed in a suitable nutrient medium comprising carbon and nitrogen sources and inorganic salts, using procedures known in the art (described in WO93/37179). The growth conditions applied were the following: Process pH was controlled at 6.0 for the first 72 h of growth, then was increased to 6.7 within 24 h, in a gradual way, and kept at this value. Temperature was controlled at 30° C. Working volume was 10 L and the total fermentation time 192 h. Controlled feeding of the medium imposed a oxygen limitation. Oxygen uptake rate was controlled by agitation following an exponential profile with a rate increase of 0.025 h$^{-1}$. The glucose-containing feed was adjusted to maintain a glucose concentration in the medium in excess of 10 g/L. Withdrawals were made when necessary. Supernatant samples were analysed for GFP-SKL using spectrophotometric analysis. Relative fluorescence was measured using samples of 200 µl, at room temperature with excitation at 490 nm, emission at 510 nm, cut-off at 495 nm, gain automatic and a molar extinction coefficient for eFGP at 488 nm of 61000 M$^{-1}$ cm$^{-1}$). The samples for the fluorescence measurements were diluted in 5 mM Tris HCl buffer with 5 mM Na$_2$EDTA pH 8.0. The filtrates were diluted 2 to 640-fold depending on the expected eGFP concentration.

Figure 12:
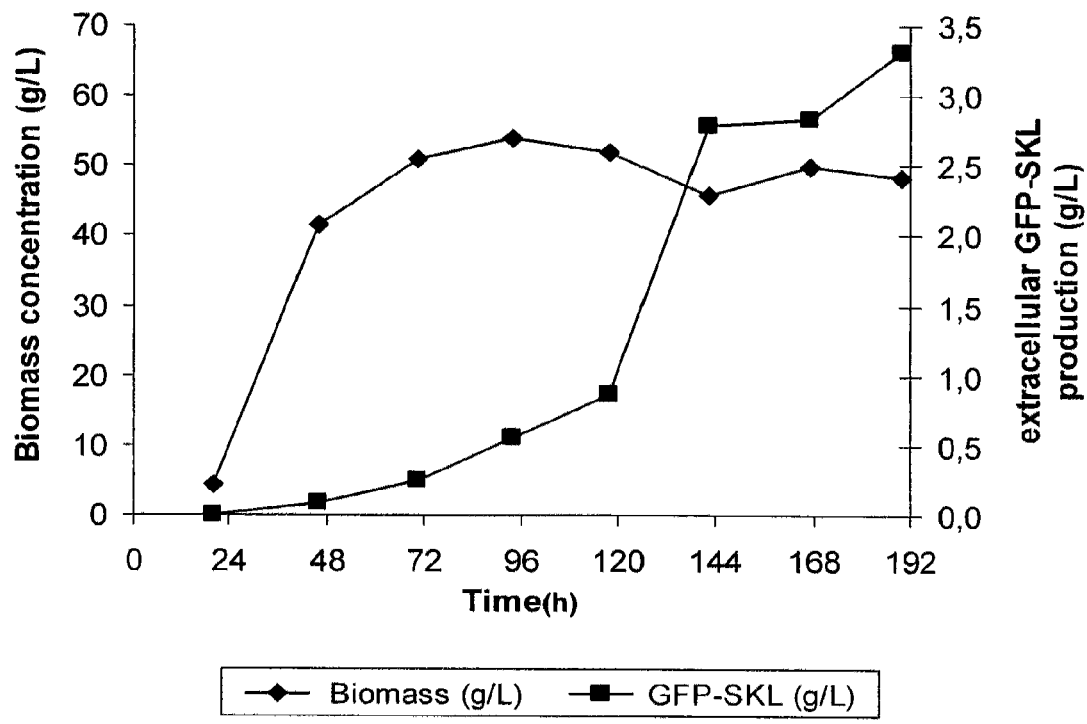
FIG. 12 shows the biomass concentration and extracellular GFP-SKL production in *A. niger* in 10 L scale fermentations.

As depicted in FIG. 12, during the first 72 h of culture (pH 6.0) biomass concentration increased rapidly and then remained almost constant until the end of the fermentation, due to the dilution effect created by the continuous feeding of the medium. In this time period, (the first 72 h), very low levels of GFP-SKL were found extracellularly (approximately 0.25 g/L). After a pH shift from 6.0 to 6.7 (effectuated between 72 and 96 h), extracellular GFP-SKL concentrations continuously increased until the end of the fermentation, reaching the value of 3.3 g/L at 192 hours. This clearly demonstrated that using the described process conditions, GFP-SKL was produced and secreted in a 10-L scale fed batch culture process with a yield of more than 3.0 g/L.

Example 7

Intracellular GFP-SKL Production Under Glucose- and Oxygen-Limited Conditions with the Same Growth Profile Strain:
Construction of the *A. niger* CBS513.88 strain over-expressing GFP-SKL and SncA/Pmp22 was described in example 5.1. Spores of the strain were stored at −80° C. ($5\times10^7$ viable spores/vial).
Inoculation Procedure:
The content of one spore-vial was added to the pre-culture medium in a baffled 2 L-shake flask (20 g/L yeast extract, 20 g/L glucose, pH 6.8 (with KOH), 300 mL medium, steam-sterilized 20 min at 121° C.). This pre-culture was cultured for 40 h at 30° C. and 220 rpm.
Fed-Batch Fermentation:
The culture was performed in a medium comprising carbon and nitrogen sources and inorganic salts, using procedures known in the art (described in WO93/37179).
The growth conditions applied were the following: Process pH was controlled at 5.5 and temperature at 30° C. Working volume was 10 L and the total fermentation time 144 h. Airflow was 1 vvm (volume air per volume medium per minute). For the glucose-limited cultures an exponential feed-profile with a rate increase of 0.025 h$^{-1}$ was applied. For the oxygen-limited fermentation oxygen uptake rate was controlled by agitation following an exponential profile with a rate increase of 0.025 h$^{-1}$. The glucose containing feed was adjusted to maintain a glucose concentration in the medium in excess of 10 g/L. Withdrawals were made when necessary. Samples were taken and cell-free extracts were prepared. Samples were analysed for GFP-SKL according to the method described in example 6.

Figure 13:
FIG. 13 shows the difference between glucose- and oxygen-limited conditions fermentation conditions on intracellular GFP-SKL production in *A. niger*.

As depicted in FIG. 13, intracellular GFP-SKL production was much higher under oxygen-limited conditions than under glucose-limited conditions. At the end of fermentation (144 h), intracellular GFP-SKL production was approximately 20-fold higher when oxygen-limited conditions were used, compared to glucose-limited conditions. This specific example clearly demonstrates that oxygen-limited conditions are favorable for peroxisomal/intracellular accumulation of GFP-SKL in a 10-L scale fed batch culture process.

Example 8

Release of the Peroxisomal Content (Acetamidase) Outside the Cell by Fusion of the Peroxisome with the Plasma Membrane

8.1 Cloning and Expression of *A. niger* Acetamidase

*A. niger* acetamidase AmdS, shown as SEQ ID NO: 41, SEQ ID NO: 42 and SEQ ID NO: 43, genomic, cDNA and protein sequence, respectively was used. Genomic DNA from CBS513.88 was used as template in a PCR reaction using SEQ ID NO: 44 and SEQ ID NO: 45 to result in coding SEQ ID NO: 46. The resulting PCR fragment (SEQ ID NO: 46) was digested with restriction enzymes PacI and AscI according to the manufacturers instructions and ligated into a PacI, AscI linearised *A. niger* expression vector as depicted in FIG. 1. This resulted in a construct in which the gene encoding the *A. niger* acetamidase was placed under control of the glaA promoter.

In addition, genomic DNA from CBS513.88 was used as template in a PCR reaction using SEQ ID NO: 44 and SEQ ID NO: 47 to result in coding SEQ ID NO: 48. The resulting PCR fragment (SEQ ID NO: 48) was digested with restriction enzymes PacI and AscI according to the manufacturers instructions and ligated into a PacI, AscI linearised *A. niger* expression vector as depicted in FIG. 1. This resulted in a construct in which the gene encoding the *A. niger* acetamidase, with engineered C-terminal SKL-tail, was placed under control of the glaA promoter. Expression of this construct resulted in the polypeptide depicted in SEQ ID NO: 49. All PCR reactions, ligations and transformations were performed using classical molecular biology techniques, as described in Molecular Cloning: A Laboratory Manual, Sambrook et al., New York: Cold Spring Harbor Press, 1989. The resulting expression constructs encoding *A. niger* acetamidase with and without C-terminal—SKL were used to transform the generic *A. niger* host capable of secreting intracellular compounds from example 5.2 and CBS513.88. The transformants were analysed by PCR for the presence of both the SncA/Pmp22 expression construct as well as the acetamidase constructs, respectively both the SncA/Pmp22 expression construct as well as the acetamidase-SKL constructs. Selected clones were further analysed in example 8.3.

8.2 Cloning and Expression of *A. nidulans* Acetamidase

For this experiment, the well-known *A. nidulans* acetamidase gene was used (Tilburn et al, 1983, Gene 26:205-221), shown as SEQ ID NO: 50, SEQ ID NO: 51 and SEQ ID NO: 52, genomic, cDNA and protein sequence, respectively. Plasmid DNA from an expression vector containing the *A. nidulans* AmdS (described in EP13211523) was used as template in a PCR reaction using SEQ ID NO: 53 and SEQ ID NO: 54 to result in coding SEQ ID NO: 55. The resulting PCR fragment (SEQ ID NO: 55) was digested with restriction enzymes PacI and AscI according to the manufacturers instructions and ligated into a PacI, AscI linearised *A. niger* expression vector as depicted in FIG. 1. This resulted in a construct in which the gene encoding the *A. nidulans* acetamidase was placed under control of the glaA promoter.

In addition, plasmid DNA from an expression vector containing the *A. nidulans* AmdS (described in EP13211523) was used as template in a PCR reaction using SEQ ID NO: 53 and SEQ ID NO: 56 to result in coding SEQ ID NO: 57. The resulting PCR fragments (SEQ ID NO: 57) was digested with restriction enzymes PacI and AscI according to the manufacturers instructions and ligated into a PacI, AscI linearised *A. niger* expression vector as depicted in FIG. 1. This resulted in a construct in which the gene encoding the *A. nidulans* acetamidase, with engineered SKL-tail, was placed under control of the glaA promoter. Expression of this construct resulted in the polypeptide depicted in SEQ ID NO: 58. All PCR reactions, ligations and transformations were performed using classical molecular biology techniques, as described in Molecular Cloning: A Laboratory Manual, Sambrook et al., New York: Cold Spring Harbor Press, 1989. The resulting expression constructs encoding *A. nidulans* acetamidase with and without C-terminal—SKL were used to transform the generic *A. niger* host capable of secreting intracellular compounds from example 5.2 and CBS513.88. Transformants were analysed by PCR for the presence of both the SncA/Pmp22 expression construct as well as the acetamidase constructs, respectively both the SncA/Pmp22 expression construct as well as the acetamidase-SKL constructs. Selected clones were further analysed in example 8.3.

8.3 Culture of the Transformants from Example 8.1 and 8.2 for Analysis of Release of Intracellular Acetamidases The *A. niger* AmdS with and without—SKL or the *A. nidulans* Amds with and without—SKL were transformed to both the generic *A. niger* host capable of secreting intracellular compounds (constructed in example 5.2) and CBS513.88 as a negative control. Using PCR, transformants were selected containing a single copy of the acetamidase expression cassette. The 8 types of clones were cultured in shake flasks in an orbital shaker at 30° C., 250 RPM in MEAM buffered medium (described extensively in patent application WO 98/46772). Supernatant samples were taken at 120 and 144-hour time points after start of culture. The supernatant samples were cleared by centrifugation and separated from residual cell debris by ultrafiltration through 0.45 µm filters (catalogus number 4614, Pall, Ann Arbor, Mo. USA). The supernatant samples were analysed for acetamidase activity in example 8.4.

8.4 Acetamidase Enzyme Assays

Figure 14:
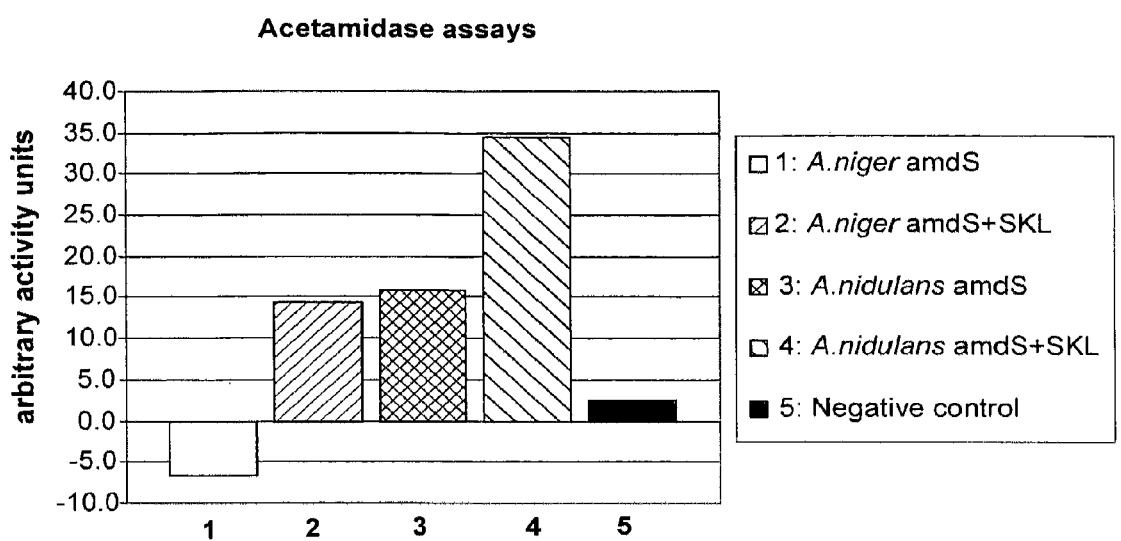
FIG. 14 shows the presence of secreted acetamidase with C-terminal SKL in culture supernatants; blocks 2 and 4 depict acetamidases with SKL in *A. niger* host cells capable of secreting intracellular compounds; blocks 1 and 3 depict acetamidases without SKL in *A. niger* host cells capable of secreting intracellular compounds.

Supernatant samples from 8.3 were analysed for acetamidase activity by measuring the free ammonia in the samples Free ammonia is indicative for acetamidase activity (as described by Skouloubris et al., Molecular Microbiology (2001) 40(3), 596-609). All selected and analysed transformed clones of CBS513.88 did not produce detectable free ammonia (data not shown). In FIG. 14, free ammonia produced by the 4 types of transformants of the strain of example 5.2 is depicted. As clearly shown in FIG. 14, the constructs that contain a C-terminal SKL extension (i.e. targeted to the peroxisome) resulted in higher extracellular acetamidase activity compared to the constructs that not containing a C-terminal SKL extension. This higher acetamidase activity was caused by release of the peroxisomal content. In FIG. 14, the difference between secreted acetamidases with and without SKL outside the cell can be clearly observed when comparing blocks 2 (A niger acetamidase with SKL) and 4 (*A. nidulans* acetamidase with SKL) with the corresponding blocks 1 (*A. niger* acetamidase without SKL) and 3 (*A. nidulans* acetamidase without SKL); in the supernatants acetamidases with SKL, much more acetamidase activity was present.

Example 9

Release of the Peroxisomal Content (Amadoriase) Outside the Cell by Fusion of the Peroxisome with the Plasma Membrane

9.1 Cloning and Expression of *A. niger* Amadoriase-SRL

*A. niger* amadoriase-SRL, shown as SEQ ID NO: 59, SEQ ID NO 60 and SEQ ID NO 61, genomic, cDNA and protein sequence, respectively was used. Genomic DNA from CBS513.88 was used as template in a PCR reaction using SEQ ID NO: 62 and SEQ ID NO: 63 to result in coding SEQ ID NO: 64. The resulting PCR fragment (SEQ ID NO: 64) was digested with restriction enzymes PacI and AscI according to the manufacturers instructions and ligated into a PacI, AscI linearised *A. niger* expression vector as depicted in FIG. 11. This resulted in a construct in which the gene encoding an amadoriase was placed under control of the glaA promoter. The resulting plasmid DNA was digested with restriction enzymes PacI and AscI according to the manufacturers instructions and ligated into a PacI, AscI linearised *A. niger* expression vector as depicted in FIG. 1. All PCR reactions, ligations and transformations were performed using classical molecular biology techniques, as described in Molecular Cloning: A Laboratory Manual, Sambrook et al., New York: Cold Spring Harbor Press, 1989. The resulting expression construct encoding *A. niger* amadoriase-SRL was used to transform the generic *A. niger* host capable of secreting intracellular compounds from example 5.2 and CBS513.88 (as a negative control). Transformants were analysed by PCR for the presence of both the SncA/Pmp22 expression construct as well as the amadoriase-SRL construct. Selected clones were further analysed in example 9.2

9.2 Cultivation of the Transformants from Example 9.1 for Analysis of Release of Intracellular Amadoriases The *A. niger* amadoriase-SRL was transformed to the generic *A. niger* host capable of secreting intracellular compounds from example 5.2 and CBS513.88 (as a negative control). Using PCR, a selection was made for clones containing a single copy of the amadoriase expression cassette. Clones representative for the 2 types of transformants (*A. niger* of example 5.2 and CB513.88, each comprising amadoriase-SRL) were selected and were cultured in shake flasks in an orbital shaker at 30° C., 250 RPM in MEAM buffered medium (described extensively in patent application WO 98/46772). Supernatant samples were taken at 96-hour time points after start of culture. The supernatant samples were cleared by centrifugation and separated from residual cell debris by ultra filtration through 0.45 µm filters (catalogue number 4614, Pall, Ann Arbor, Mo. USA). The supernatant samples were analysed for amadoriase activity in example 9.3.

9.3 Amadoriase Enzyme Assays

Figure 15:
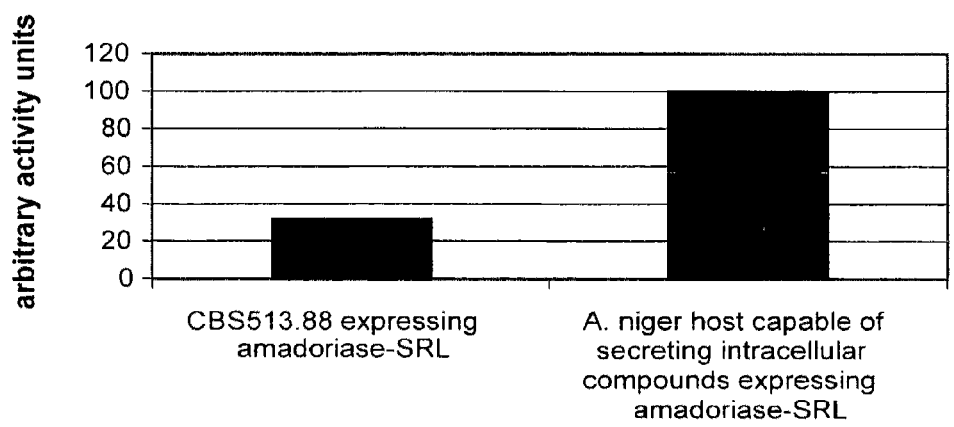
FIG. 15 shows the presence of secreted amadoriase with C-terminal SRL in culture supernatants.

Supernatant samples from 9.2 were analysed by enzyme assay. The amadoriase activity assay is described by Monnier V M et al, J Biol Chem. 1997 Feb. 7; 272(6):3437-43. The enzyme activity was monitored by the release of glucosone measured by a colorimetric reaction with ortho-phenylene diamine (OPD) using fructosyl propylamine (kindly provided by Prof. Monnier) as a substrate. This assay is based on the end point measurement of glucosone formed after 120 min of reaction time. The reaction mixture contained 20 mM sodium phosphate, pH 7.4, 10 mM OPD, 10 mM fructosyl propylamine, and supernatant sample from example 9.3 in a final volume of 1 ml. After incubation at 37° C. for 2 h, the absorbance at 320 nm was measured. Results are depicted in FIG. 15. The results clearly demonstrate that generic *A. niger* host capable of secreting intracellular compounds from example 5.2 is able to produce at least three times more amadoriase-SRL in the culture medium than the control strain CBS513.88 transformed with the amadoriase-SRL gene.

Example 10

Increased Excretion of Peroxisomal Metabolites

An experiment was conducted to demonstrate that the generic *A. niger* host capable of secreting intracellular compounds from example 5.2 demonstrates increased secretion of peroxisomal metabolites as compared to negative control strain CBS513.88.

The generic *A. niger* host capable of secreting intracellular compounds from example 5.2 and CBS513.88 were cultured according to example 6. Supernatant samples were taken at 138 hours after start of culture. The supernatant samples were cleared by centrifugation and separated from residual cell debris by ultrafiltration through 0.45 µm filters (catalogus number 4614, Pall, Ann Arbor, Mo. USA). Subsequently, the samples were analysed for peroxisomal beta-oxidation metabolites (David E Metzler, Biochemistry, 2nd edition, Academic Press 2001) by 1H NMR.

2 ml of the supernatant was acidified to pH 2 with 4N HCl and extracted with 4 ml chloroform. From the clear chloroform layer (after centrifugation), 3 ml was back extracted into 2 ml water at pH 7.5 (adjusted with 0.01 N NaOH). 1.5 ml of the water layer after centrifugation was lyophilised and redissolved into 0.5 ml $D_2O$ (Deuterium $H_2O$, Cambridge Isotope Laboratories). 1H NMR spectra were measured at 600 MHZ on a Bruker Avance 600 spectrometer. The compounds, showing an increase in concentration of a factor of 2, were identified by 2-dimensional NMR spectroscopy to be branched fatty acids: isobutyric acid (a), isovaleric acid (b) and a-methyl butyric acid (c). These are known to originate from beta-oxidation of branched iso- and ante-iso fatty acids for a+b and c respectively (David E Metzler, Biochemistry, 2nd edition, Academic Press 2001).

The quantitative comparison between these acids was made by integration of their characteristic methyl resonances in the NMR spectrum (1.114 ppm for a, 0.928 for b and 0.885 and 1.089 ppm for c). For all three metabolites, a factor of two of increase was measured for the generic *A. niger* host capable of secreting intracellular compounds from example 5.2 compared to the negative control strain CBS513.88. The results clearly demonstrated that the generic *A. niger* host capable of secreting intracellular compounds from example 5.2, can be used as host strain for the extracellular production of peroxisomal metabolites of interest.

The invention described and claimed herein is not to be limited in scope by the specific embodiments herein enclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In case of conflict, the present disclosure including definitions will control.

The invention claimed is:

1. A method for production of a polypeptide of interest in a eukaryotic cell containing a peroxisome that expresses a chimeric protein comprising a domain of a v-SNARE polypeptide that is normally exposed at the cytosolic side of a donor membrane of the secretory pathway, a transmembrane domain of a peroxisomal membrane protein and a sequence that targets the transmembrane domain to the peroxisomal membrane wherein said peroxisome fuses via the v-SNARE domain on the cytosolic side of its peroxisomal membrane with a membrane-structure of the cell involved in the secretory pathway of the cell wherein the membrane-structure of the cell involved in the secretory pathway of the cell is selected from the group consisting of the plasma membrane, the Golgi complex and the Endoplasmic Reticulum, wherein said polypeptide of interest is present in the peroxisome of the cell, said method comprising culturing the eukaryotic cell in a suitable culture medium.

2. The method according to claim 1, wherein the culture medium comprises material selected from the group consisting of an activator of ceramide activated protein phosphatase (CAPP) and a substance inducing peroxisome proliferation.

3. The method according to claim 1, wherein at least 0.01 g/l of the polypeptide of interest is produced.

4. A method for production of a polypeptide of interest in a eukaryotic cell according to claim 1, wherein the eukaryotic cell is cultured and a suitable amount of oxygen is fed to the culture to maintain the culture under conditions of oxygen limitation.

5. A method for production of a polypeptide of interest in a eukaryotic cell according to claim 1, wherein the pH of the culture medium is altered during the culture process.

6. A method for production of a polypeptide of interest in a eukaryotic cell according to claim 1, wherein the total duration of the culture process is 192 hours, which consists of:
   a first phase of 72 hours wherein the pH of the culture medium is 6.0,
   a transition phase of 24 hours wherein the pH of the culture medium is altered in a linear course from 6.0 to 6.7, and
   a second phase of 96 hours wherein the pH of the culture medium is 6.7.

7. A method for production of a polypeptide of interest in a eukaryotic cell according to claim 1, wherein the temperature of the culture medium is altered during the culture process.

8. A method for production of a polypeptide of interest in a eukaryotic cell according to claim 1, wherein the temperature of the culture medium is altered from 30° C. to 36° C. during the culture process.

9. A method for production of a polypeptide of interest in a eukaryotic cell according to claim 4, wherein the eukaryotic cell is a filamentous fungus.

10. The method according to claim 1, further comprising purifying the polypeptide.

11. The method according to claim 2, wherein the activator of CAPP is ceramide.

12. The method according to claim 2, wherein the substance inducing peroxisome proliferation is oleate.

13. A method according to claim 9, wherein the filamentous fungus is an *Aspergillus* species, and more preferably an *Aspergillus niger* strain.

14. A method according to claim 13, wherein the *Aspergillus* species is an *Aspergillus niger* strain.

* * * * *

SEQUENCE LISTING

<160> NUMBER OF SEQ ID NOS: 64

<210> SEQ ID NO 1
<211> LENGTH: 36
<212> TYPE: DNA
<213> ORGANISM: Artificial Sequence
<220> FEATURE:
<223> OTHER INFORMATION: primer

<400> SEQUENCE: 1
gtcctgttaa ttaaccacca tggcgaacac aacgtg                             36

<210> SEQ ID NO 2
<211> LENGTH: 37
<212> TYPE: DNA
<213> ORGANISM: Artificial Sequence
<220> FEATURE:
<223> OTHER INFORMATION: primer

<400> SEQUENCE: 2
acttcaggcg cgcctcaaga gacatcactc attacgg                            37

<210> SEQ ID NO 3
<211> LENGTH: 45
<212> TYPE: DNA
<213> ORGANISM: Artificial Sequence
<220> FEATURE:
<223> OTHER INFORMATION: primer

<400> SEQUENCE: 3
acttcaggcg cgccttacag cttcgaagag acatcactca ttacg                   45

<210> SEQ ID NO 4
<211> LENGTH: 1793
<212> TYPE: DNA
<213> ORGANISM: Artificial Sequence
<220> FEATURE:
<223> OTHER INFORMATION: synthetic construct

<400> SEQUENCE: 4
gtcctgttaa ttaaccacca tggcgaacac aacgtgggag catagagcca agagcaagca    60
agctcagacg gcagcagcga ttccaccaga atggacttta ccagccgata tacttctcga   120
ctcctcggcg aatgtcctcg atgtgcccag gacctgtggg ctcctgaccg aaagagaaat   180
ccatattacc gaagactatg atgccacagc attacttgaa agttggctac cggagagtt    240 cagctcactc gaggtcacga cagcattctg caagcgggct gcaattgcgc agcagttgac   300
ctgctgcttg acggaaatct tcttcgacaa agcactagcc agagcaaagc agctcgacga   360
aattctggct caaactgggg taacaaccgg gccactgcat ggcctgccca taagtatcaa   420
ggagtcgttc aatgtccctg agttccgac tacactgggg ttcgtcggat ttctcgatcg    480
ggccccggcg tccatgagtt ccgccctggt tgagatcctg aacaactgtg ggctgttct    540 atatgtcaag accaatgtcc cccagacaat gatgactccg gactcccata caatgtcctt   600
cggtcgtgtg ctcaacccgc acggacggag cctgaccgct ggaggcagca gtggcggaga   660
gggagcattg gtggcgatga ggggctcagt cctcggcgtg gggacagata tcgcggctc    720 cattcgcatc cccgccctct gctgtggtgt ttttggttc aaacccacgg cttgccgtat    780
cccatatgca ggtcaaacgt ctgccggcg tccgggtatg acgggcatcc tgccgtccgc    840
cgggcccatg tgccattcta tccgcgatgc agaactcttt ctcaaagttg tcctcaactc    900

| | |
|---|---|
| gaggcctgcc gatctggatg actatgcact cgacattcca tggtcccctg ctccgcaaaa | 960 |
| ggagaggctt actattgggc tcctgcccga ggacccgtcg ttcccgcttc atccaccgat | 1020 |
| gcgacgtacc ctgaacgccg cagtgaaggc gctgactaca gccggacacc gggtcatcga | 1080 |
| cctctcagga caggctccgt ccttctccaa tgcatgttct ctggcattgc gatatttcgg | 1140 |
| cctggacccg gatcgaactg cactgcgcca cataacgcag gcgggcgaac ctttcattcc | 1200 |
| ttcgctcaaa ttcacctatg atctcaatga gccgacacgt gagcccacct tgagagatct | 1260 |
| attcgaatcg aatgtcgccc gtagtcagct cgcaacccag gcacgaaagc tcttcgttga | 1320 |
| taatcagctt gatctgttcc tgggcgcggc ttatcaaagc acatcggttc ccatgatac | 1380 |
| ctacggtatt ccggtatata ccgtgctttg aacctgatt aatgtgggta tcccacactg | 1440 |
| cctttcttgt tttcttttc tttttgttt cccccccttc tttctgctcc aattgcatgg | 1500 |
| ggtgtctgct aatgatgcac tagtatccgg cgtgcgttat cccatttggg caggccaaca | 1560 |
| aggtagagga cgcagcgtat aaccgcgacg tctcttatgt gccagactgt aagttgcgcc | 1620 |
| cctcaattgg tctcgctcag tctactaact actgtagatc ggccagaaga aattgaaggc | 1680 |
| gcaccgtgtc acatccatct gataggcaga ccgatggcgg acgaaaaatt ggttcaggat | 1740 |
| gcgaagacta tatgcaccgt aatgagtgat gtctcttgag gcgcgcctga agt | 1793 |

<210> SEQ ID NO 5
<211> LENGTH: 1802
<212> TYPE: DNA
<213> ORGANISM: Artificial Sequence
<220> FEATURE:
<223> OTHER INFORMATION: synthetic construct

<400> SEQUENCE: 5

| | |
|---|---|
| gtcctgttaa ttaaccacca tggcgaacac aacgtgggag catagagcca agagcaagca | 60 |
| agctcagacg gcagcagcga ttccaccaga atggacttta ccagccgata tacttctcga | 120 |
| ctcctcggcg aatgtcctcg atgtgcccag gacctgtggg ctcctgaccg aaagagaaat | 180 |
| ccatattacc gaagactatg atgccacagc attacttgaa agttggcta ccggagagtt | 240 |
| cagctcactc gaggtcacga cagcattctg caagcgggct gcaattgcgc agcagttgac | 300 |
| ctgctgcttg acggaaatct tcttcgacaa agcactagcc agagcaaagc agctcgacga | 360 |
| aattctggct caaactgggg taacaaccgg gccactgcat ggcctgccca taagtatcaa | 420 |
| ggagtcgttc aatgtccctg gagttccgac tacactgggg ttcgtcggat ttctcgatcg | 480 |
| ggccccggcg tccatgagtt ccgccctggt tgagatcctg aacaactgtg gggctgttct | 540 |
| atatgtcaag accaatgtcc cccagacaat gatgactccg gactcccata caatgtcttt | 600 |
| cggtcgtgtg ctcaacccgc acggacggag cctgaccgct ggaggcagca gtggcggaga | 660 |
| gggagcattg gtggcgatga ggggctcagt cctcggcgtg gggacagata tcgccggctc | 720 |
| cattcgcatc cccgccctct gctgtggtgt ttttggtttc aaacccacgg cttgccgtat | 780 |
| cccatatgca ggtcaaacgt ctgccgggcg tccgggtatg acgggcatcc tgccgtccgc | 840 |
| cgggcccatg tgccattcta tccgcgatgc agaactcttt ctcaaagttg tcctcaactc | 900 |
| gaggcctgcc gatctggatg actatgcact cgacattcca tggtcccctg ctccgcaaaa | 960 |
| ggagaggctt actattgggc tcctgcccga ggacccgtcg ttcccgcttc atccaccgat | 1020 |
| gcgacgtacc ctgaacgccg cagtgaaggc gctgactaca gccggacacc gggtcatcga | 1080 |
| cctctcagga caggctccgt ccttctccaa tgcatgttct ctggcattgc gatatttcgg | 1140 |
| cctggacccg gatcgaactg cactgcgcca cataacgcag gcgggcgaac ctttcattcc | 1200 |

-continued

```
ttcgctcaaa ttcacctatg atctcaatga gccgacacgt gagcccacct tgagagatct    1260
attcgaatcg aatgtcgccc gtagtcagct cgcaacccag gcacgaaagc tcttcgttga    1320
taatcagctt gatctgttcc tgggcgcggc ttatcaaagc acatcggttc cccatgatac    1380
ctacggtatt ccggtatata ccgtgctttg gaacctgatt aatgtgggta tcccacactg    1440
cctttcttgt tttctttttc tttttgttt ccccccttc tttctgctcc aattgcatgg     1500
ggtgtctgct aatgatgcac tagtatccgg cgtgcgttat cccatttggg caggccaaca    1560
aggtagagga cgcagcgtat aaccgcgacg tctcttatgt gccagactgt aagttgcgcc    1620
cctcaattgg tctcgctcag tctactaact actgtagatc ggccagaaga aattgaaggc    1680
gcaccgtgtc acatccatct gataggcaga ccgatggcgg acgaaaaatt ggttcaggat    1740
gcgaagacta tatgcaccgt aatgagtgat gtctcttcga agctataagg cgcgcctgaa    1800
gt                                                                   1802

<210> SEQ ID NO 6
<211> LENGTH: 40
<212> TYPE: DNA
<213> ORGANISM: Artificial Sequence
<220> FEATURE:
<223> OTHER INFORMATION: primer

<400> SEQUENCE: 6
gtcctgttaa ttaaccacca tgcttccccc ctttgattac                              40

<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
acttcaggcg cgccctagtc aagctcaatc aatgggtat                               39

<210> SEQ ID NO 8
<211> LENGTH: 49
<212> TYPE: DNA
<213> ORGANISM: Artificial Sequence
<220> FEATURE:
<223> OTHER INFORMATION: primer

<400> SEQUENCE: 8
acttcaggcg cgccttacag cttcgagtca agctcaatca atgggtatt                    49

<210> SEQ ID NO 9
<211> LENGTH: 1987
<212> TYPE: DNA
<213> ORGANISM: Artificial Sequence
<220> FEATURE:
<223> OTHER INFORMATION: synthetic construct

<400> SEQUENCE: 9
gtcctgttaa ttaaccacca tgcttccccc ctttgattac tttacgtatc gtcgcatccg      60
gtaggttacc ccgtgtgcct tcacgcagca acttaagcag tcctacacag cccacatgca     120
acttagccga cggctcactg accattcaca gggacctcaa gaggagggaa cgggcggctc     180
gatttgcatc gctatctccc gattatcatg cgcccttctc ggctatcgac agggttatca     240
ttaacaagcc tatccaggac ttggtatatg aggtccagaa tgattccttg gcacctttag     300
atgtcctacg cacatacggc aaggttgcag tcaaggctca cgaaaagacc aattgcgtga     360
```

```
ctgagcttct attgcctgag gcagaatcat gggctcagtc cgaagtaaac ctaaaaggtc    420
ccctggcggg tgtgcctatc tctttgaaag actcggtgca agtcaaagga ttcgatatta    480
ctctggggta taccaagttc gcgtgtaaac cgtataagga ggatggtcca atggcaaagc    540
tgttgaagga tgctggtagg tgacctgtgc cgcgaaacat cacagaaagt atccctgcgc    600
taatgatgaa ctccatcagg tgcggtccca tatgcgaaaa cggcgctgcc cgtgacgctt    660
ctgtcgttcg aatcagcaaa cgctctttgg ggtcactgcc ttaacccaca tgtcccggaa    720
tactctcctg gcggctcgac gggtggtgaa ggtgctctgc tggctcttgg tggtcgcatc    780
ggtatcgggt cggatgtcgc tggctcggtt cgcgttcccg ctgcctggag cggcatctac    840
tccctccgct gtagtactgg ccgctggcct aaggtcggag tcaacaccag catggctggc    900
caggaaggtg ttgccagtgt cttcagtcct atggcccgta cttttgaacga tctcacctat    960 ttcaccaaag ctattgtcgg aatgaagcct tggaactacg accataccgt ccaccctatc   1020
tcctggagag aagatgagga aattgaagcc caaaacaaaa ggttgaggat cggcctcatg   1080
agcaacgatg gtaagttcca agagcgggga catcaaggac actacttggg cctttctgac   1140
cacttgcagg tgtcgttccc ccaacgccgg ccattgaacg tgctatttcc accacagtag   1200
ccgccctcac cgccgctggg catactgtat ctgagatcac acccccgct gcggctgaca   1260 cttttactgg tctctccctc gcctcgcagc tgctcaactc tgatgggtgc gtcacgttta   1320
actcgcatct gcacagcttt gagccatccg accctggtgc agatcagctg acgcggatat   1380
gcaatctgcc ccgtcctcta cgttatctct actaccttg ggttcggtac atccgacggg   1440
atgagaagtg ggcgacgctg atccgcgggt ttgcccccaa gtctgcggcg gagctttgga   1500
agctcactgc ccagcgggaa gctttccggg cgacctggca cagctggtgg gatgccgaga   1560
cgcagcagta cgatttcatc ctctgccccg tcaatgcgac gccggctctg ccccacaaag   1620
ccatgcacga tgcggtatcc tcatgcggat acacgttcct ctggaacctg ctggactaca   1680
cagccggtgt cgtgcctgtc tcgcacgtgg acgcgaagaa ggatgctctg tctggtccgt   1740
acaagaaggt gctgaaacag ctgggagcca gcaacgcggt ggcctacggt gcctggaagc   1800
actacgacgc ggcgaagatg gcgggattgc ctactgcagt gcaggtggtg ggacgcagat   1860
ggcaggaaga gaaggtgctt ggatacatgg cggcagttga ggaggccttg agcagtatc   1920 aggacccggt aactggagaa gggggggaaat acccattgat tgagcttgac tagggcgcgc   1980
ctgaagt                                                             1987

<210> SEQ ID NO 10
<211> LENGTH: 1996
<212> TYPE: DNA
<213> ORGANISM: Artificial Sequence
<220> FEATURE:
<223> OTHER INFORMATION: synthetic construct

<400> SEQUENCE: 10
gtcctgttaa ttaaccacca tgcttccccc ctttgattac tttacgtatc gtcgcatccg     60
gtaggttacc ccgtgtgcct tcacgcagca acttaagcag tcctacacag cccacatgca    120
acttagccga cggctcactg accattcaca gggacctcaa gaggagggaa cgggcggctc    180
gatttgcatc gctatctccc gattatcatg cgcccttctc ggctatcgac agggttatca    240
ttaacaagcc tatccaggac ttggtatatg aggtccagaa tgattccttg gcacctttag    300
atgtcctacg cacatacggc aaggttgcag tcaaggctca cgaaaagacc aattgcgtga    360
ctgagcttct attgcctgag gcagaatcat gggctcagtc cgaagtaaac ctaaaaggtc    420
```

```
cccctggcggg tgtgcctatc tctttgaaag actcggtgca agtcaaagga ttcgatatta    480
ctctggggta taccaagttc gcgtgtaaac cgtataagga ggatggtcca atggcaaagc    540
tgttgaagga tgctggtagg tgacctgtgc cgcgaaacat cacagaaagt atccctgcgc    600
taatgatgaa ctccatcagg tgcggtccca tatgcgaaaa cggcgctgcc cgtgacgctt    660
ctgtcgttcg aatcagcaaa cgctcttttgg ggtcactgcc ttaacccaca tgtcccggaa    720
tactctcctg gcggctcgac gggtggtgaa ggtgctctgc tggctcttgg tggtcgcatc    780
ggtatcgggt cggatgtcgc tggctcggtt cgcgttcccg ctgcctggag cggcatctac    840
tccctccgct gtagtactgg ccgctggcct aaggtcggag tcaacaccag catggctggc    900
caggaaggtg ttgccagtgt cttcagtcct atggcccgta ctttgaacga tctcacctat    960
ttcaccaaag ctattgtcgg aatgaagcct tggaactacg accataccgt ccaccctatc   1020
tcctggagag aagatgagga aattgaagcc caaacaaaa ggttgaggat cggcctcatg    1080
agcaacgatg gtaagttcca agagcgggga catcaaggac actacttggg cctttctgac   1140
cacttgcagg tgtcgttccc ccaacgccgg ccattgaacg tgctatttcc accacagtag   1200
ccgccctcac cgccgctggg catactgtat ctgagatcac accccccgct gcggctgaca   1260
cttttactgg tctctccctc gcctcgcagc tgctcaactc tgatgggtgc gtcacgttta   1320
actcgcatct gcacagcttt gagccatccg accctggtgc agatcagctg acgcggatat   1380
gcaatctgcc ccgtcctcta cgttatctct actacctttg ggttcggtac atccgacggg   1440
atgagaagtg ggcgacgctg atccgcgggt ttgcccccaa gtctgcggcg agctttgga    1500 agctcactgc ccagcgggaa gctttccggg cgacctggca cagctggtgg gatgccgaga   1560
cgcagcagta cgatttcatc ctctgccccg tcaatgcgac gccggctctg ccccacaaag   1620
ccatgcacga tgcggtatcc tcatgcggat acacgttcct ctggaacctg ctggactaca   1680
cagccggtgt cgtgcctgtc tcgcacgtgg acgcgaagaa ggatgctctg tctggtccgt   1740
acaagaaggt gctgaaacag ctgggagcca gcaacgcggt ggcctacggt gcctggaagc   1800
actacgacgc ggcgaagatg gcgggattgc ctactgcagt gcaggtggtg ggacgcagat   1860
ggcaggaaga gaaggtgctt ggatacatgg cggcagttga ggaggccttg gagcagtatc   1920
aggacccggt aactggagaa gggggggaaat acccattgat tgagcttgac tcgaagctat   1980
aaggcgcgcc tgaagt                                                  1996
```

<210> SEQ ID NO 11
<211> LENGTH: 628
<212> TYPE: DNA
<213> ORGANISM: Aspergillus niger

<400> SEQUENCE: 11

```
atgtccgagc agccctatga tccctacatc ccctctggcg ccaatggggc tggcgccggc     60
gccagcgctg cgcaaaatgg cgaccccagg acacgggaaa tcgacaaagt aagttgccga    120
aacgcctcgc ggtcaacttt tatcgttcca caaggatatg tcgcccaggt tgaataggat    180
gtgatggctt tccagttttc atttggactt ccatctgagt tcaactggac ttggaggcca    240
ccgggtcttt ttgaatctta ttaagcttgt gtctattatg gcatttgtcg caaagtattt    300
actaacgctg tgtttcttct ctgtctagaa atccaagaa accgttgaca caatgcgctc    360
caacatcttt aaagtttcag aacgtggtga acgtctagat tccctccagg acaagacgga    420
caatttggca acatcagcgc agggattccg cagaggtgcc aaccgcgtga ggaagcaaat    480
gtggtggaag gatatgaaga tgcgcgtgtg cctaatcgtt tgtatcatta ttctgctcat    540
```

```
tgtgattatc gtccctgcag gtaagatcag cgctatcctc cagcactcca ccaagctgga    600
ctcggaaaaa catcccggaa tgcgctaa                                       628

<210> SEQ ID NO 12
<211> LENGTH: 408
<212> TYPE: DNA
<213> ORGANISM: Aspergillus niger

<400> SEQUENCE: 12
atgtccgagc agccctatga tccctacatc ccctctggcg ccaatggggc tggcgccggc     60
gccagcgctg cgcaaaatgg cgaccccagg acacgggaaa tcgacaaaaa aatccaagaa    120
accgttgaca caatgcgctc caacatcttt aaagtttcag aacgtggtga acgtctagat    180
tccctccagg acaagacgga caatttggca acatcagcgc agggattccg cagaggtgcc    240
aaccgcgtga ggaagcaaat gtggtggaag gatatgaaga tgcgcgtgtg cctaatcgtt    300
tgtatcatta ttctgctcat tgtgattatc gtccctgcag gtaagatcag cgctatcctc    360
cagcactcca ccaagctgga ctcggaaaaa catcccggaa tgcgctaa                 408

<210> SEQ ID NO 13
<211> LENGTH: 135
<212> TYPE: PRT
<213> ORGANISM: Aspergillus niger

<400> SEQUENCE: 13

Met Ser Glu Gln Pro Tyr Asp Pro Tyr Ile Pro Ser Gly Ala Asn Gly
1               5                  10                  15

Ala Gly Ala Gly Ala Ser Ala Ala Gln Asn Gly Asp Pro Arg Thr Arg
            20                  25                  30

Glu Ile Asp Lys Lys Ile Gln Glu Thr Val Asp Thr Met Arg Ser Asn
        35                  40                  45

Ile Phe Lys Val Ser Glu Arg Gly Glu Arg Leu Asp Ser Leu Gln Asp
    50                  55                  60

Lys Thr Asp Asn Leu Ala Thr Ser Ala Gln Gly Phe Arg Arg Gly Ala
65                  70                  75                  80

Asn Arg Val Arg Lys Gln Met Trp Trp Lys Asp Met Lys Met Arg Val
                85                  90                  95

Cys Leu Ile Val Cys Ile Ile Leu Leu Ile Val Ile Ile Val Pro
            100                 105                 110

Ala Gly Lys Ile Ser Ala Ile Leu Gln His Ser Thr Lys Leu Asp Ser
        115                 120                 125

Glu Lys His Pro Gly Met Arg
    130                 135

<210> SEQ ID NO 14
<211> LENGTH: 974
<212> TYPE: DNA
<213> ORGANISM: Aspergillus niger

<400> SEQUENCE: 14
atgtctgcca agttccagga tgaggccgtc acctcgatac gggaggacac aaaggaattg     60
gtgcacaagg ttggaaaccg gttgactggc gatggctatc tcgctgtagg ttttgcgcct    120
gtgtaatcac accccgaatg cgtgttttgc agtccactga ttgagacaat gcgcgtccgt    180
tatagctcta cctccgccaa ctgcagtcca acccctgcg cactaagatg ttgacctccg    240
gtgtcctgtc cagtctgcaa gaatcctggc ctcgtggat cgcccatgat gtcagcaagc    300
acggtcacta cttcagcgcc cgcgtcccca aaatggccct ctacggaatg ttcatcagcg    360
```

```
cccccgctggg ccactttctc atcggaattc tgcagcgggt cttcgctggc cggactagca    420
tcaaggccaa gatcctgcaa attctcgcca gcaacttgtt ggtatgttcg atctgacact    480
ccccttctga cgtgcggctg gaatgctgac gcgacgcagg tctcccccat ccaaaacgcc    540
gtgtacctgt gctgcatggc cgttatcgcg ggcgcgcgca ccttccacca ggtccgcgct    600
accgtgcggg ccggtttcat gcccgtcatg aaggtcagct gggtcacctc gcccattgcg    660
ctggcctttg cccagaagtt cctccccgag cacacctggg tgcctttctt caacattgtc    720
gggttcgtca ttggaaccta cgtcaacacg cacaccaaga gaagcgtctt gaggctctc    780 cgcaaggtaa atcaactacg tgacgatccc gccgacgcga ccagtcgcta acctagcacg    840
acagcgctac gaccaacgcc gtggacccgg tagcgagtac gacaagggcg actaccggta    900
aacgatgtaa atatactgta cctagcttat gactaccgac tggttagtgt ggacttcccg    960
atatggtcgg ttag                                                     974

<210> SEQ ID NO 15
<211> LENGTH: 675
<212> TYPE: DNA
<213> ORGANISM: Aspergillus niger

<400> SEQUENCE: 15
atgtctgcca agttccagga tgaggccgtc acctcgatac gggaggacac aaaggaattg     60
gtgcacaagg ttggaaaccg gttgactggc gatggctatc tcgctctcta cctccgccaa    120
ctgcagtcca accccctgcg cactaagatg ttgacctccg tgtcctgtc cagtctgcaa    180 gaaatcctgg cctcgtggat cgcccatgat gtcagcaagc acggtcacta cttcagcgcc    240
cgcgtcccca aaatggccct ctacggaatg ttcatcagcg ccccgctggg ccactttctc    300
atcggaattc tgcagcgggt cttcgctggc cggactagca tcaaggccaa gatcctgcaa    360
attctcgcca gcaacttgtt ggtctccccc atccaaaacg ccgtgtacct gtgctgcatg    420
gccgttatcg cgggcgcgcg caccttccac caggtccgcg ctaccgtgcg ggccggtttc    480
atgcccgtca tgaaggtcag ctgggtcacc tcgcccattg cgctggcctt tgcccagaag    540
ttcctccccg agcacacctg ggtgcctttc ttcaacattg tcgggttcgt cattggaacc    600
tacgtcaaca cgcacaccaa gaagaagcgt cttgaggctc tccgcaagtg tggacttccc    660
gatatggtcg gttag                                                    675

<210> SEQ ID NO 16
<211> LENGTH: 224
<212> TYPE: PRT
<213> ORGANISM: Aspergillus niger

<400> SEQUENCE: 16

Met Ser Ala Lys Phe Gln Asp Glu Ala Val Thr Ser Ile Arg Glu Asp
1               5                   10                  15

Thr Lys Glu Leu Val His Lys Val Gly Asn Arg Leu Thr Gly Asp Gly
            20                  25                  30

Tyr Leu Ala Leu Tyr Leu Arg Gln Leu Gln Ser Asn Pro Leu Arg Thr
        35                  40                  45

Lys Met Leu Thr Ser Gly Val Leu Ser Ser Leu Gln Glu Ile Leu Ala
    50                  55                  60

Ser Trp Ile Ala His Asp Val Ser Lys His Gly His Tyr Phe Ser Ala
65                  70                  75                  80

Arg Val Pro Lys Met Ala Leu Tyr Gly Met Phe Ile Ser Ala Pro Leu
                85                  90                  95
```

Gly His Phe Leu Ile Gly Ile Leu Gln Arg Val Phe Ala Gly Arg Thr
            100                 105                 110

Ser Ile Lys Ala Lys Ile Leu Gln Ile Leu Ala Ser Asn Leu Leu Val
        115                 120                 125

Ser Pro Ile Gln Asn Ala Val Tyr Leu Cys Cys Met Ala Val Ile Ala
    130                 135                 140

Gly Ala Arg Thr Phe His Gln Val Arg Ala Thr Val Arg Ala Gly Phe
145                 150                 155                 160

Met Pro Val Met Lys Val Ser Trp Val Thr Ser Pro Ile Ala Leu Ala
                165                 170                 175

Phe Ala Gln Lys Phe Leu Pro Glu His Thr Trp Val Pro Phe Phe Asn
            180                 185                 190

Ile Val Gly Phe Val Ile Gly Thr Tyr Val Asn Thr His Thr Lys Lys
        195                 200                 205

Lys Arg Leu Glu Ala Leu Arg Lys Cys Gly Leu Pro Asp Met Val Gly
    210                 215                 220

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
tgcttaatta accaccatgt ccgagcagcc ctatgatcc                              39

<210> SEQ ID NO 18
<211> LENGTH: 42
<212> TYPE: DNA
<213> ORGANISM: Artificial Sequence
<220> FEATURE:
<223> OTHER INFORMATION: primer

<400> SEQUENCE: 18
cctcatcctg gaacttggca gagcgcatct tcatatcctt cc                          42

<210> SEQ ID NO 19
<211> LENGTH: 543
<212> TYPE: DNA
<213> ORGANISM: Artificial Sequence
<220> FEATURE:
<223> OTHER INFORMATION: synthetic construct

<400> SEQUENCE: 19
tgcttaatta accaccatgt ccgagcagcc ctatgatccc tacatcccct ctggcgccaa        60
tggggctggc gccggcgcca cgctgcgca aatggcgac cccaggacac gggaaatcga       120
caaagtaagt tgccgaaacg cctcgcggtc aactttatc gttccacaag gatatgtcgc       180
ccaggttgaa taggatgtga tggctttcca gttttcattt ggacttccat ctgagttcaa      240
ctggacttgg aggccaccgg gtcttttga atcttattaa gcttgtgtct attatggcat      300
ttgtcgcaaa gtatttacta acgctgtgtt tcttctctgt ctagaaaatc caagaaaccg      360
ttgacacaat gcgctccaac atctttaaag tttcagaacg tggtgaacgt ctagattccc      420
tccaggacaa gacggacaat ttggcaacat cagcgcaggg attccgcaga ggtgccaacc      480
gcgtgaggaa gcaaatgtgg tggaaggata tgaagatgcg ctctgccaag ttccaggatg      540
agg                                                                    543

<210> SEQ ID NO 20
<211> LENGTH: 42
<212> TYPE: DNA
<213> ORGANISM: Artificial Sequence
<220> FEATURE:
<223> OTHER INFORMATION: primer

<400> SEQUENCE: 20
ggaaggatat gaagatgcgc tctgccaagt tccaggatga gg                          42

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
attggcgcgc cctaaccgac catatcggga agtcc                                  35

<210> SEQ ID NO 22
<211> LENGTH: 1002
<212> TYPE: DNA
<213> ORGANISM: Artificial Sequence
<220> FEATURE:
<223> OTHER INFORMATION: synthetic construct

<400> SEQUENCE: 22
ggaaggatat gaagatgcgc tctgccaagt tccaggatga ggccgtcacc tcgatacggg       60
aggacacaaa ggaattggtg cacaaggttg gaaaccggtt gactggcgat ggctatctcg      120
ctgtaggttt tgcgcctgtg taatcacacc ccgaatgcgt gttttgcagt ccactgattg      180
agacaatgcg cgtccgttat agctctacct ccgccaactg cagtccaacc cctgcgcac       240
taagatgttg acctccggtg tcctgtccag tctgcaagaa atcctggcct cgtggatcgc      300
ccatgatgtc agcaagcacg gtcactactt cagcgcccgc gtcccaaaa tggccctcta       360
cggaatgttc atcagcgccc cgctgggcca ctttctcatc ggaattctgc agcgggtctt      420
cgctggccgg actagcatca aggccaagat cctgcaaatt ctcgccagca acttgttggt      480
atgttcgatc tgacactccc cttctgacgt gcggctggaa tgctgacgcg acgcaggtct      540
cccccatcca aaacgccgtg tacctgtgct gcatggccgt tatcgcgggc gcgcgcacct      600
tccaccaggt ccgcgctacc gtgcgggccg gtttcatgcc cgtcatgaag gtcagctggg      660
tcacctcgcc cattgcgctg gccttttgccc agaagttcct ccccgagcac acctgggtgc    720
ctttcttcaa cattgtcggg ttcgtcattg gaacctacgt caacacgcac accaagaaga      780
agcgtcttga ggctctccgc aaggtaaatc aactacgtga cgatcccgcc gacgcgacca      840
gtcgctaacc tagcacgaca gcgctacgac caacgccgtg gacccggtag cgagtacgac      900
aagggcgact accggtaaac gatgtaaata tactgtacct agcttatgac taccgactgg      960
ttagtgtgga cttcccgata tggtcggtta gggcgcgcca at                        1002

<210> SEQ ID NO 23
<211> LENGTH: 1503
<212> TYPE: DNA
<213> ORGANISM: Artificial Sequence
<220> FEATURE:
<223> OTHER INFORMATION: synthetic construct

<400> SEQUENCE: 23
tgcttaatta accaccatgt ccgagcagcc ctatgatccc tacatcccct ctggcgccaa       60
tggggctggc gccggcgcca gcgctgcgca aaatggcgac cccaggacac gggaaatcga      120

```
caaagtaagt tgccgaaacg cctcgcggtc aactttatc gttccacaag gatatgtcgc      180
ccaggttgaa taggatgtga tggctttcca gttttcattt ggacttccat ctgagttcaa      240
ctggacttgg aggccaccgg gtcttttttga atcttattaa gcttgtgtct attatggcat     300
ttgtcgcaaa gtatttacta acgctgtgtt tcttctctgt ctagaaaatc caagaaaccg      360
ttgacacaat gcgctccaac atctttaaag tttcagaacg tggtgaacgt ctagattccc      420
tccaggacaa gacggacaat ttggcaacat cagcgcaggg attccgcaga ggtgccaacc      480
gcgtgaggaa gcaaatgtgg tggaaggata tgaagatgcg ctctgccaag ttccaggatg      540
aggccgtcac ctcgatacgg gaggacacaa aggaattggt gcacaaggtt ggaaaccggt      600
tgactggcga tggctatctc gctgtaggtt ttgcgcctgt gtaatcacac cccgaatgcg      660
tgttttgcag tccactgatt gagacaatgc gcgtccgtta tagctctacc tccgccaact      720
gcagtccaac cccctgcgca ctaagatgtt gacctccggt gtcctgtcca gtctgcaaga      780
aatcctggcc tcgtggatcg cccatgatgt cagcaagcac ggtcactact tcagcgcccg      840
cgtccccaaa atggccctct acggaatgtt catcagcgcc ccgctgggcc actttctcat      900
cggaattctg cagcgggtct tcgctggccg gactagcatc aaggccaaga tcctgcaaat      960
tctcgccagc aacttgttgg tatgttcgat ctgacactcc ccttctgacg tgcggctgga     1020
atgctgacgc gacgcaggtc tcccccatcc aaaacgccgt gtacctgtgc tgcatggccg     1080
ttatcgcggg cgcgcgcacc ttccaccagg tccgcgctac cgtgcgggcc ggtttcatgc     1140
ccgtcatgaa ggtcagctgg gtcacctcgc ccattgcgct ggcctttgcc cagaagttcc     1200
tccccgagca cacctgggtg cctttcttca acattgtcgg gttcgtcatt ggaacctacg     1260
tcaacacgca caccaagaag aagcgtcttg aggctctccg caaggtaaat caactacgtg     1320
acgatcccgc cgacgcgacc agtcgctaac ctagcacgac agcgctacga ccaacgccgt     1380
ggacccggta gcgagtacga caagggcgac taccggtaaa cgatgtaaat atactgtacc     1440
tagcttatga ctaccgactg gttagtgtgg acttcccgat atggtcggtt agggcgcgcc     1500
aat                                                                   1503
```

<210> SEQ ID NO 24
<211> LENGTH: 318
<212> TYPE: PRT
<213> ORGANISM: Artificial Sequence
<220> FEATURE:
<223> OTHER INFORMATION: synthetic construct

<400> SEQUENCE: 24

```
Met Ser Glu Gln Pro Tyr Asp Pro Tyr Ile Pro Ser Gly Ala Asn Gly
1               5                   10                  15

Ala Gly Ala Gly Ala Ser Ala Ala Gln Asn Gly Asp Pro Arg Thr Arg
            20                  25                  30

Glu Ile Asp Lys Lys Ile Gln Glu Thr Val Asp Thr Met Arg Ser Asn
        35                  40                  45

Ile Phe Lys Val Ser Glu Arg Gly Glu Arg Leu Asp Ser Leu Gln Asp
    50                  55                  60

Lys Thr Asp Asn Leu Ala Thr Ser Ala Gln Gly Phe Arg Arg Gly Ala
65                  70                  75                  80

Asn Arg Val Arg Lys Gln Met Trp Trp Lys Asp Met Lys Met Arg Ser
                85                  90                  95

Ala Lys Phe Gln Asp Glu Ala Val Thr Ser Ile Arg Glu Asp Thr Lys
            100                 105                 110
```

```
Glu Leu Val His Lys Val Gly Asn Arg Leu Thr Gly Asp Gly Tyr Leu
    115                 120                 125

Ala Leu Tyr Leu Arg Gln Leu Gln Ser Asn Pro Leu Arg Thr Lys Met
130                 135                 140

Leu Thr Ser Gly Val Leu Ser Ser Leu Gln Glu Ile Leu Ala Ser Trp
145                 150                 155                 160

Ile Ala His Asp Val Ser Lys His Gly His Tyr Phe Ser Ala Arg Val
                165                 170                 175

Pro Lys Met Ala Leu Tyr Gly Met Phe Ile Ser Ala Pro Leu Gly His
                180                 185                 190

Phe Leu Ile Gly Ile Leu Gln Arg Val Phe Ala Gly Arg Thr Ser Ile
            195                 200                 205

Lys Ala Lys Ile Leu Gln Ile Leu Ala Ser Asn Leu Leu Val Ser Pro
210                 215                 220

Ile Gln Asn Ala Val Tyr Leu Cys Cys Met Ala Val Ile Ala Gly Ala
225                 230                 235                 240

Arg Thr Phe His Gln Val Arg Ala Thr Val Arg Ala Gly Phe Met Pro
                245                 250                 255

Val Met Lys Val Ser Trp Val Thr Ser Pro Ile Ala Leu Ala Phe Ala
                260                 265                 270

Gln Lys Phe Leu Pro Glu His Thr Trp Val Pro Phe Asn Ile Val
            275                 280                 285

Gly Phe Val Ile Gly Thr Tyr Val Asn Thr His Thr Lys Lys Arg
290                 295                 300

Leu Glu Ala Leu Arg Lys Cys Gly Leu Pro Asp Met Val Gly
305                 310                 315

<210> SEQ ID NO 25
<211> LENGTH: 720
<212> TYPE: DNA
<213> ORGANISM: Artificial Sequence
<220> FEATURE:
<223> OTHER INFORMATION: synthetic construct

<400> SEQUENCE: 25
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 26
<211> LENGTH: 239
<212> TYPE: PRT
<213> ORGANISM: Artificial Sequence
<220> FEATURE:
<223> OTHER INFORMATION: synthetic construct protein
```

<400> SEQUENCE: 26

| Met | Val | Ser | Lys | Gly | Glu | Glu | Leu | Phe | Thr | Gly | Val | Val | Pro | Ile | Leu |
| 1 | | | | 5 | | | | | 10 | | | | | 15 | |
| Val | Glu | Leu | Asp | Gly | Asp | Val | Asn | Gly | His | Lys | Phe | Ser | Val | Ser | Gly |
| | | | 20 | | | | | 25 | | | | | 30 | | |
| Glu | Gly | Glu | Gly | Asp | Ala | Thr | Tyr | Gly | Lys | Leu | Thr | Leu | Lys | Phe | Ile |
| | | 35 | | | | | 40 | | | | | 45 | | | |
| Cys | Thr | Thr | Gly | Lys | Leu | Pro | Val | Pro | Trp | Pro | Thr | Leu | Val | Thr | Thr |
| 50 | | | | | 55 | | | | | 60 | | | | | |
| Leu | Thr | Tyr | Gly | Val | Gln | Cys | Phe | Ser | Arg | Tyr | Pro | Asp | His | Met | Lys |
| 65 | | | | | 70 | | | | | 75 | | | | | 80 |
| Gln | His | Asp | Phe | Phe | Lys | Ser | Ala | Met | Pro | Glu | Gly | Tyr | Val | Gln | Glu |
| | | | | 85 | | | | | 90 | | | | | 95 | |
| Arg | Thr | Ile | Phe | Phe | Lys | Asp | Asp | Gly | Asn | Tyr | Lys | Thr | Arg | Ala | Glu |
| | | | 100 | | | | | 105 | | | | | 110 | | |
| Val | Lys | Phe | Glu | Gly | Asp | Thr | Leu | Val | Asn | Arg | Ile | Glu | Leu | Lys | Gly |
| | | | 115 | | | | | 120 | | | | | 125 | | |
| Ile | Asp | Phe | Lys | Glu | Asp | Gly | Asn | Ile | Leu | Gly | His | Lys | Leu | Glu | Tyr |
| | | 130 | | | | | 135 | | | | | 140 | | | |
| Asn | Tyr | Asn | Ser | His | Asn | Val | Tyr | Ile | Met | Ala | Asp | Lys | Gln | Lys | Asn |
| 145 | | | | | 150 | | | | | 155 | | | | | 160 |
| Gly | Ile | Lys | Val | Asn | Phe | Lys | Ile | Arg | His | Asn | Ile | Glu | Asp | Gly | Ser |
| | | | | 165 | | | | | 170 | | | | | 175 | |
| Val | Gln | Leu | Ala | Asp | His | Tyr | Gln | Gln | Asn | Thr | Pro | Ile | Gly | Asp | Gly |
| | | | 180 | | | | | 185 | | | | | 190 | | |
| Pro | Val | Leu | Leu | Pro | Asp | Asn | His | Tyr | Leu | Ser | Thr | Gln | Ser | Ala | Leu |
| | | | 195 | | | | | 200 | | | | | 205 | | |
| Ser | Lys | Asp | Pro | Asn | Glu | Lys | Arg | Asp | His | Met | Val | Leu | Leu | Glu | Phe |
| | 210 | | | | | 215 | | | | | 220 | | | | |
| Val | Thr | Ala | Ala | Gly | Ile | Thr | Leu | Gly | Met | Asp | Glu | Leu | Tyr | Lys | |
| 225 | | | | | 230 | | | | | 235 | | | | | |

<210> SEQ ID NO 27
<211> LENGTH: 34
<212> TYPE: DNA
<213> ORGANISM: Artificial Sequence
<220> FEATURE:
<223> OTHER INFORMATION: primer

<400> SEQUENCE: 27
gtcctgttaa ttaaccacca tggtgagcaa gggc					34

<210> SEQ ID NO 28
<211> LENGTH: 40
<212> TYPE: DNA
<213> ORGANISM: Artificial Sequence
<220> FEATURE:
<223> OTHER INFORMATION: primer

<400> SEQUENCE: 28
ctcatcctgg aacttggcag acttgtacag ctcgtccatg					40

<210> SEQ ID NO 29
<211> LENGTH: 758
<212> TYPE: DNA
<213> ORGANISM: Artificial Sequence
<220> FEATURE:
<223> OTHER INFORMATION: synthetic construct

<400> SEQUENCE: 29

```
gtcctgttaa ttaaccacca tggtgagcaa gggcgaggag ctgttcaccg gggtggtgcc      60
catcctggtc gagctggacg gcgacgtaaa cggccacaag ttcagcgtgt ccggcgaggg     120
cgagggcgat gccacctacg gcaagctgac cctgaagttc atctgcacca ccggcaagct     180
gcccgtgccc tggcccaccc tcgtgaccac cctgacctac ggcgtgcagt gcttcagccg     240
ctaccccgac cacatgaagc agcacgactt cttcaagtcc gccatgcccg aaggctacgt     300
ccaggagcgc accatcttct tcaaggacga cggcaactac aagacccgcg ccgaggtgaa     360
gttcgagggc gacaccctgg tgaaccgcat cgagctgaag ggcatcgact tcaaggagga     420
cggcaacatc ctggggcaca agctggagta caactacaac agccacaacg tctatatcat     480
ggccgacaag cagaagaacg gcatcaaggt gaacttcaag atccgccaca acatcgagga     540
cggcagcgtg cagctcgccg accactacca gcagaacacc cccatcggcg acggccccgt     600
gctgctgccc gacaaccact acctgagcac ccagtccgcc ctgagcaaag accccaacga     660
gaagcgcgat cacatggtcc tgctggagtt cgtgaccgcc gccgggatca ctctcggcat     720
ggacgagctg tacaagtctg ccaagttcca ggatgagg                             758
```

<210> SEQ ID NO 30
<211> LENGTH: 41
<212> TYPE: DNA
<213> ORGANISM: Artificial Sequence
<220> FEATURE:
<223> OTHER INFORMATION: primer

<400> SEQUENCE: 30

```
catggacgag ctgtacaagt ctgccaagtt ccaggatgag g                          41
```

<210> SEQ ID NO 31
<211> LENGTH: 38
<212> TYPE: DNA
<213> ORGANISM: Artificial Sequence
<220> FEATURE:
<223> OTHER INFORMATION: primer

<400> SEQUENCE: 31

```
acttcaggcg cgccctaacc gaccatatcg ggaagtcc                              38
```

<210> SEQ ID NO 32
<211> LENGTH: 1004
<212> TYPE: DNA
<213> ORGANISM: Artificial Sequence
<220> FEATURE:
<223> OTHER INFORMATION: synthetic construct

<400> SEQUENCE: 32

```
catggacgag ctgtacaagt ctgccaagtt ccaggatgag gccgtcacct cgatacggga     60
ggacacaaag gaattggtgc acaaggttgg aaaccggttg actggcgatg ctatctcgc     120
tgtaggtttt gcgcctgtgt aatcacaccc cgaatgcgtg ttttgcagtc cactgattga     180
gacaatgcgc gtccgttata gctctacctc gccaactgc agtccaaccc cctgcgcact     240
aagatgttga cctccggtgt cctgtccagt ctgcaagaaa tcctggcctc gtggatcgcc     300
catgatgtca gcaagcacgg tcactacttc agcgcccgcg tccccaaaat ggccctctac     360
ggaatgttca tcagcgcccc gctgggccac tttctcatcg gaattctgca gcgggtcttc     420
gctggccgga ctagcatcaa ggccaagatc ctgcaaattc tcgccagcaa cttgttggta     480
tgttcgatct gacactcccc ttctgacgtg cggctggaat gctgacgcga cgcaggtctc     540
```

-continued

| | |
|---|---|
| cccatccaa aacgccgtgt acctgtgctg catggccgtt atcgcgggcg cgcgcacctt | 600 |
| ccaccaggtc cgcgctaccg tgcgggccgg tttcatgccc gtcatgaagg tcagctgggt | 660 |
| cacctcgccc attgcgctgg cctttgccca gaagttcctc cccgagcaca cctgggtgcc | 720 |
| tttcttcaac attgtcgggt tcgtcattgg aacctacgtc aacacgcaca ccaagaagaa | 780 |
| gcgtcttgag gctctccgca aggtaaatca actacgtgac gatcccgccg acgcgaccag | 840 |
| tcgctaacct agcacgacag cgctacgacc aacgccgtgg acccggtagc gagtacgaca | 900 |
| agggcgacta ccggtaaacg atgtaaatat actgtaccta gcttatgact accgactggt | 960 |
| tagtgtggac ttcccgatat ggtcggttag ggcgcgcctg aagt | 1004 |

<210> SEQ ID NO 33
<211> LENGTH: 1721
<212> TYPE: DNA
<213> ORGANISM: Artificial Sequence
<220> FEATURE:
<223> OTHER INFORMATION: synthetic product

<400> SEQUENCE: 33

| | |
|---|---|
| gtcctgttaa ttaaccacca tggtgagcaa gggcgaggag ctgttcaccg gggtggtgcc | 60 |
| catcctggtc gagctggacg gcgacgtaaa cggccacaag ttcagcgtgt ccggcgaggg | 120 |
| cgagggcgat gccacctacg gcaagctgac cctgaagttc atctgcacca ccggcaagct | 180 |
| gcccgtgccc tggcccaccc tcgtgaccac cctgacctac ggcgtgcagt gcttcagccg | 240 |
| ctaccccgac cacatgaagc agcacgactt cttcaagtcc gccatgcccg aaggctacgt | 300 |
| ccaggagcgc accatcttct tcaaggacga cggcaactac aagacccgcg ccgaggtgaa | 360 |
| gttcgagggc gacaccctgg tgaaccgcat cgagctgaag ggcatcgact tcaaggagga | 420 |
| cggcaacatc ctggggcaca gcctggagta caactacaac agccacaacg tctatatcat | 480 |
| ggccgacaag cagaagaacg gcatcaaggt gaacttcaag atccgccaca acatcgagga | 540 |
| cggcagcgtg cagctcgccg accactacca gcagaacacc cccatcggcg acggccccgt | 600 |
| gctgctgccc gacaaccact acctgagcac ccagtccgcc ctgagcaaag accccaacga | 660 |
| gaagcgcgat cacatggtcc tgctggagtt cgtgaccgcc gccgggatca ctctcggcat | 720 |
| ggacgagctg tacaagtctg ccaagttcca ggatgaggcc gtcacctcga tacgggagga | 780 |
| cacaaaggaa ttggtgcaca aggttggaaa ccggttgact ggcgatggct atctcgctgt | 840 |
| aggttttgcg cctgtgtaat cacaccccga atgcgtgttt gcagtccac tgattgagac | 900 |
| aatgcgcgtc cgttatagct ctacctccgc caactgcagt ccaacccct gcgcactaag | 960 |
| atgttgacct ccggtgtcct gtccagtctg caagaaatcc tggcctcgtg gatcgcccat | 1020 |
| gatgtcagca agcacggtca ctacttcagc gcccgcgtcc ccaaaatggc cctctacgga | 1080 |
| atgttcatca gcgccccgct gggccacttt ctcatcggaa ttctgcagcg ggtcttcgct | 1140 |
| ggccggacta gcatcaaggc caagatcctg caaattctcg ccagcaactt gttggtatgt | 1200 |
| tcgatctgac actcccttc tgacgtgcgg ctggaatgct gacgcgacgc aggtctcccc | 1260 |
| catccaaaac gccgtgtacc tgtgctgcat ggccgttatc gcgggcgcgc gcaccttcca | 1320 |
| ccaggtccgc gctaccgtgc gggccggttt catgcccgtc atgaaggtca gctgggtcac | 1380 |
| ctcgcccatt gcgctggcct ttgcccagaa gttcctcccc gagcacacct gggtgccttt | 1440 |
| cttcaacatt gtcgggttcg tcattggaac ctacgtcaac acgcacacca agaagaagcg | 1500 |
| tctcgaggct ctccgcaagg taaatcaact acgtgacgat cccgccgacg cgaccagtcg | 1560 |
| ctaacctagc acgacagcgc tacgaccaac gccgtggacc cggtagcgag tacgacaagg | 1620 |

```
gcgactaccg gtaaacgatt taaatatact gtacctagct tatgactacc gactggttag   1680
tgtggacttc ccgatatggt cggttagggc gcgcctgaag t                      1721
```

<210> SEQ ID NO 34
<211> LENGTH: 462
<212> TYPE: PRT
<213> ORGANISM: Artificial Sequence
<220> FEATURE:
<223> OTHER INFORMATION: synthetic construct

<400> SEQUENCE: 34

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Ala Lys Phe Gln Asp Glu Ala Val Thr Ser Ile Arg Glu Asp Thr Lys
                245                 250                 255

Glu Leu Val His Lys Val Gly Asn Arg Leu Thr Gly Asp Gly Tyr Leu
            260                 265                 270

Ala Leu Tyr Leu Arg Gln Leu Gln Ser Asn Pro Leu Arg Thr Lys Met
        275                 280                 285

Leu Thr Ser Gly Val Leu Ser Ser Leu Gln Glu Ile Leu Ala Ser Trp
    290                 295                 300

Ile Ala His Asp Val Ser Lys His Gly His Tyr Phe Ser Ala Arg Val
305                 310                 315                 320

Pro Lys Met Ala Leu Tyr Gly Met Phe Ile Ser Ala Pro Leu Gly His
                325                 330                 335

Phe Leu Ile Gly Ile Leu Gln Arg Val Phe Ala Gly Arg Thr Ser Ile
            340                 345                 350
```

-continued

Lys Ala Lys Ile Leu Gln Ile Leu Ala Ser Asn Leu Leu Val Ser Pro
                355                 360                 365

Ile Gln Asn Ala Val Tyr Leu Cys Cys Met Ala Val Ile Ala Gly Ala
        370                 375                 380

Arg Thr Phe His Gln Val Arg Ala Thr Val Arg Ala Gly Phe Met Pro
385                 390                 395                 400

Val Met Lys Val Ser Trp Val Thr Ser Pro Ile Ala Leu Ala Phe Ala
                405                 410                 415

Gln Lys Phe Leu Pro Glu His Thr Trp Val Pro Phe Phe Asn Ile Val
            420                 425                 430

Gly Phe Val Ile Gly Thr Tyr Val Asn Thr His Thr Lys Lys Lys Arg
        435                 440                 445

Leu Glu Ala Leu Arg Lys Cys Gly Leu Pro Asp Met Val Gly
450                 455                 460

<210> SEQ ID NO 35
<211> LENGTH: 45
<212> TYPE: DNA
<213> ORGANISM: Artificial Sequence
<220> FEATURE:
<223> OTHER INFORMATION: primer

<400> SEQUENCE: 35
gtcctgttaa ttaaccttca ccatgtccga gcagccctat gatcc                    45

<210> SEQ ID NO 36
<211> LENGTH: 549
<212> TYPE: DNA
<213> ORGANISM: Artificial Sequence
<220> FEATURE:
<223> OTHER INFORMATION: synthetic construct

<400> SEQUENCE: 36
gtcctgttaa ttaaccttca ccatgtccga gcagccctat gatccctaca tccctctgg     60 cgccaatggg gctggcgccg gcgccagcgc tgcgcaaaat ggcgacccca ggacacggga   120
aatcgacaaa gtaagttgcc gaaacgcctc gcggtcaact tttatcgttc acaaggata    180 tgtcgcccag gttgaatagg atgtgatggc tttccagttt tcatttggac ttccatctga   240
gttcaactgg acttggaggc caccgggtct ttttgaatct tattaagctt gtgtctatta   300
tggcatttgt cgcaaagtat ttactaacgc tgtgtttctt ctctgtctag aaaatccaag   360
aaaccgttga cacaatgcgc tccaacatct ttaaagtttc agaacgtggt gaacgtctag   420
attccctcca ggacaagacg gacaatttgg caacatcagc gcaggattc cgcagaggtg    480 ccaaccgcgt gaggaagcaa atgtggtgga aggatatgaa gatgcgctct gccaagttcc   540
aggatgagg                                                           549

<210> SEQ ID NO 37
<211> LENGTH: 39
<212> TYPE: DNA
<213> ORGANISM: Artificial Sequence
<220> FEATURE:
<223> OTHER INFORMATION: primer

<400> SEQUENCE: 37
acttcaggcg cgcctttaac cgaccatatc gggaagtcc                           39

<210> SEQ ID NO 38
<211> LENGTH: 1006
<212> TYPE: DNA
<213> ORGANISM: Artificial Sequence

```
<220> FEATURE:
<223> OTHER INFORMATION: synthetic construct

<400> SEQUENCE: 38
ggaaggatat gaagatgcgc tctgccaagt tccaggatga ggccgtcacc tcgatacggg      60
aggacacaaa ggaattggtg cacaaggttg gaaaccggtt gactggcgat ggctatctcg     120
ctgtaggttt tgcgcctgtg taatcacacc ccgaatgcgt gttttgcagt ccactgattg     180
agacaatgcg cgtccgttat agctctacct ccgccaactg cagtccaacc cctgcgcac      240
taagatgttg acctccggtg tcctgtccag tctgcaagaa atcctggcct cgtggatcgc     300
ccatgatgtc agcaagcacg gtcactactt cagcgcccgc gtccccaaaa tggccctcta     360
cggaatgttc atcagcgccc cgctgggcca ctttctcatc ggaattctgc agcgggtctt     420
cgctggccgg actagcatca aggccaagat cctgcaaatt ctcgccagca acttgttggt     480
atgttcgatc tgacactccc cttctgacgt gcggctggaa tgctgacgcg acgcaggtct     540
cccccatcca aaacgccgtg tacctgtgct gcatggccgt tatcgcgggc gcgcgcacct     600
tccaccaggt ccgcgctacc gtgcgggccg gtttcatgcc cgtcatgaag gtcagctggg     660
tcacctcgcc cattgcgctg gccttttgcc agaagttcct ccccgagcac acctgggtgc     720
cttttcttcaa cattgtcggg ttcgtcattg aacctacgt caacacgcac accaagaaga     780
agcgtcttga ggctctccgc aaggtaaatc aactacgtga cgatcccgcc gacgcgacca     840
gtcgctaacc tagcacgaca gcgctacgac caacgccgtg gacccggtag cgagtacgac     900
aagggcgact accggtaaac gatgtaaata tactgtacct agcttatgac taccgactgg     960
ttagtgtgga cttcccgata tggtcggtta aaggcgcgcc tgaagt                   1006

<210> SEQ ID NO 39
<211> LENGTH: 1513
<212> TYPE: DNA
<213> ORGANISM: Artificial Sequence
<220> FEATURE:
<223> OTHER INFORMATION: synthetic construct

<400> SEQUENCE: 39
gtcctgttaa ttaaccttca ccatgtccga gcagccctat gatccctaca tcccctctgg      60
cgccaatggg gctggcgccg gcgccagcgc tgcgcaaaat ggcgacccca ggacacggga     120
aatcgacaaa gtaagttgcc gaaacgcctc gcggtcaact tttatcgttc cacaaggata     180
tgtcgcccag gttgaatagg atgtgatggc tttccagttt tcatttggac ttccatctga     240
gttcaactgg acttggaggc caccgggtct ttttgaatct tattaagctt gtgtctatta     300
tggcatttgt cgcaaagtat ttactaacgc gtgtgtttctt ctctgtctag aaaatccaag     360
aaaccgttga cacaatgcgc tccaacatct ttaaagtttc agaacgtggt gaacgtctag     420
attccctcca ggacaagacg gacaatttgg caacatcagc gcagggattc cgcagaggtg     480
ccaaccgcgt gaggaagcaa atgtggtgga aggatatgaa gatgcgctct gccaagttcc     540
aggatgaggc cgtcacctcg atacgggagg acacaaagga attggtgcac aaggttggaa     600
accggttgac tggcgatggc tatctcgctg taggttttgc gcctgtgtaa tcacacccg      660
aatgcgtgtt ttgcagtcca ctgattgaga caatgcgcgt ccgttatagc tctacctccg     720
ccaactgcag tccaaccccc tgcgcactaa gatgttgacc tccggtgtcc tgtccagtct     780
gcaagaaatc ctggcctcgt ggatcgccca tgatgtcagc aagcacggtc actacttcag     840
cgcccgcgtc cccaaaatgg ccctctacgg aatgttcatc agcgcccgc tgggccactt     900
tctcatcgga attctgcagc gggtcttcgc tggccggact agcatcaagg ccaagatcct     960
```

```
gcaaattctc gccagcaact tgttggtatg ttcgatctga cactcccctt ctgacgtgcg    1020
gctggaatgc tgacgcgacg caggtctccc ccatccaaaa cgccgtgtac ctgtgctgca    1080
tggccgttat cgcgggcgcg cgcaccttcc accaggtccg cgctaccgtg cgggccggtt    1140
tcatgcccgt catgaaggtc agctgggtca cctcgcccat gcgctggcc tttgcccaga     1200 agttcctccc cgagcacacc tgggtgcctt tcttcaacat tgtcgggttc gtcattggaa    1260
cctacgtcaa cacgcacacc aagaagaagc gtcttgaggc tctccgcaag gtaaatcaac    1320
tacgtgacga tcccgccgac gcgaccagtc gctaacctag cacgcagcg ctacgaccaa     1380 cgccgtggac ccggtagcga gtacgacaag ggcgactacc ggtaaacgat gtaaatatac    1440
tgtacctagc ttatgactac cgactggtta gtgtggactt cccgatatgg tcggttaaag    1500
gcgcgcctga agt                                                       1513
```

<210> SEQ ID NO 40
<211> LENGTH: 318
<212> TYPE: PRT
<213> ORGANISM: Artificial Sequence
<220> FEATURE:
<223> OTHER INFORMATION: synthetic construct

<400> SEQUENCE: 40

```
Met Ser Glu Gln Pro Tyr Asp Pro Tyr Ile Pro Ser Gly Ala Asn Gly
1               5                   10                  15

Ala Gly Ala Gly Ala Ser Ala Ala Gln Asn Gly Asp Pro Arg Thr Arg
            20                  25                  30

Glu Ile Asp Lys Lys Ile Gln Glu Thr Val Asp Thr Met Arg Ser Asn
        35                  40                  45

Ile Phe Lys Val Ser Glu Arg Gly Glu Arg Leu Asp Ser Leu Gln Asp
    50                  55                  60

Lys Thr Asp Asn Leu Ala Thr Ser Ala Gln Gly Phe Arg Arg Gly Ala
65                  70                  75                  80

Asn Arg Val Arg Lys Gln Met Trp Trp Lys Asp Met Lys Met Arg Ser
                85                  90                  95

Ala Lys Phe Gln Asp Glu Ala Val Thr Ser Ile Arg Glu Asp Thr Lys
            100                 105                 110

Glu Leu Val His Lys Val Gly Asn Arg Leu Thr Gly Asp Gly Tyr Leu
        115                 120                 125

Ala Leu Tyr Leu Arg Gln Leu Gln Ser Asn Pro Leu Arg Thr Lys Met
    130                 135                 140

Leu Thr Ser Gly Val Leu Ser Ser Leu Gln Glu Ile Leu Ala Ser Trp
145                 150                 155                 160

Ile Ala His Asp Val Ser Lys His Gly His Tyr Phe Ser Ala Arg Val
                165                 170                 175

Pro Lys Met Ala Leu Tyr Gly Met Phe Ile Ser Ala Pro Leu Gly His
            180                 185                 190

Phe Leu Ile Gly Ile Leu Gln Arg Val Phe Ala Gly Arg Thr Ser Ile
        195                 200                 205

Lys Ala Lys Ile Leu Gln Ile Leu Ala Ser Asn Leu Leu Val Ser Pro
    210                 215                 220

Ile Gln Asn Ala Val Tyr Leu Cys Cys Met Ala Val Ile Ala Gly Ala
225                 230                 235                 240

Arg Thr Phe His Gln Val Arg Ala Thr Val Arg Ala Gly Phe Met Pro
                245                 250                 255

Val Met Lys Val Ser Trp Val Thr Ser Pro Ile Ala Leu Ala Phe Ala
```

|  |  | 260 |  |  |  | 265 |  |  |  | 270 |  |
|--|--|--|--|--|--|--|--|--|--|--|--|

Gln Lys Phe Leu Pro Glu His Thr Trp Val Pro Phe Phe Asn Ile Val
        275                 280                 285

Gly Phe Val Ile Gly Thr Tyr Val Asn Thr His Thr Lys Lys Arg
        290                 295                 300

Leu Glu Ala Leu Arg Lys Cys Gly Leu Pro Asp Met Val Gly
305                 310                 315

<210> SEQ ID NO 41
<211> LENGTH: 1980
<212> TYPE: DNA
<213> ORGANISM: Aspergillus niger

<400> SEQUENCE: 41

```
atggccctca catcctggga acaaaccgca gcggccaaac gccaatccgt cctcaacgcc      60
atccccgaga atggcgcat caagggtcct atccccgcac cgtcggagca gcgcgacgta     120
acaggcccct catccagca gttcctatcc ccacgcgagg ttgaaatcac cgaaacagac     180
gccgtaggga tcacagagcg aactacaacg ggccagtgga cagctgtgga ggtgaccgag     240
gcgttctgcc atcgcgcagc attggcgcat caactcgtac attccccatc acaaggagt     300
gctagtctgc gctttactaa tcgagaaaaa ggtaaactgc ttgcatgaaa tcttcttcga     360
tgccgcgctt gaaaccgccc gcattctaga cgaccactac accaagaccg gcaagccact     420
cggtcccctt cacggcctcc ctgtcagtct gaaggatcaa ttccacgtca agggcgtaga     480
aacaaccatg ggttacgtcg gctggataaa caccttccaa gcaagacca atgacccgcg     540
ctatcttaca cacgaaagcg aactcgttaa agaactccgc gccgcgggag ccgtcctcta     600
ctgcaagact agcgtcccca tgacgttgat gtcaggtgaa accatgaaca atatcataac     660
ttacacacat aacccgaaga acaggcttct cagttctgga ggtagttccg ggggcgaagg     720
agcactgatc gcgttgcggg gatcaccagc cgggtttggt acggatatcg ggggtagtat     780
ccgtgttcct gcgtcgttca atggactgta tgggatacgg ccgtctgtgg ggagaatgcc     840
gtacgagggg gcggccaatt cgggcgatgg acagaatact gtgttgtcgg ttgtggggcc     900
gttgtctcct tcggcgagag ggttgatatt gctgttcaag acggtgttgg gggcaatgcc     960
gtggttggga gatcctggtg tgttggagat tccctggagg gaggaaatcg tagaggagac    1020
gagaaaatta gtgcagggaa agccagaggg gctagctttt ggaatattct acgatgatgg    1080
tcaggtaaag ccgcagccac cggtcgagag agcgatgcgg attgctgcag agacgatcaa    1140
gcgtctagga cataaggtga gtgccctcct tcttcttgcg acactgctaa cattcatccc    1200
agctcatcaa ttgggaaccc ccctctcacc taacagccgc ctccctcgca gtaagtcccc    1260
catccaaccc actacaccac aaccccctaa caataaacca accccagaa ccgcgcctac    1320
aacatggacg gcggcgccga cgtactccaa aacttcgccc tgtccaacga agccatccac    1380
acctccgtag taatcgacgc atcaggatcc ccccaaaaga ccgcactaga gatcgccgcg    1440
ctaaacgtcg agaagcgcga ataccagaaa caataccttg actactgaa cagcacggcg    1500
caattgacag ggactggacg accgtcgac gcggtcattt gtccagtggc gccgcatgcg    1560
gcgtgcattc cggggaagta tgcgacgatc gggtatacgg cgtttattaa tgtgttggat    1620
tatacgagtg cggttgtgcc ggttacgagt gctgatagga gggtggatgt tgtagggaag    1680
gaaggaaggg agtattttgg gggagttggat aggaagaccg agggggagtg taagttcttc    1740
cctttctttt cttctttctt ttcattgagc tatccaattt ggttggaggt cttgtgtgtt    1800
tgtttgttcg gagagtggtg atggggttat gtgctgactg gatgtttcta tctagacgat    1860
```

```
gcggatgtgt tgatggggc gccggctggg attcagctct ttggaagacg gcttcaggag   1920
gagaagattc tggtactggc tgagtatctt ggtgaggaat caagaaggc tagtgcttga   1980
```

<210> SEQ ID NO 42
<211> LENGTH: 1695
<212> TYPE: DNA
<213> ORGANISM: Aspergillus niger

<400> SEQUENCE: 42

```
atggccctca catcctggga acaaaccgca gcggccaaac gccaatccgt cctcaacgcc     60
atccccgaga atggcgcat caagggtcct atccccgcac cgtcggagca gcgcgacgta    120
acaggcccct acatccagca gttcctatcc ccacgcgagg ttgaaatcac cgaaacagac    180
gccgtaggga tcacagagcg aactacaacg ggccagtgga cagctgtgga ggtgaccgag    240
gcgttctgcc atcgcgcagc attggcgcat caactcgtaa actgcttgca tgaaatcttc    300
ttcgatgccg cgcttgaaac cgcccgcatt ctagacgacc actacaccaa gaccggcaag    360
ccactcggtc cccttcacgg cctccctgtc agtctgaagg atcaattcca cgtcaagggc    420
gtagaaacaa ccatgggtta cgtcggctgg ataaacacct tccaaggcaa gaccaatgac    480
ccgcgctatc ttacacacga aagcgaactc gttaaagaac tccgcgccgc gggagccgtc    540
ctctactgca agactagcgt ccccatgacg ttgatgtcag gtgaaaccat gaacaatatc    600
ataacttaca cacataaccc gaagaacagg cttctcagtt ctggaggtag ttccgggggc    660
gaaggagcac tgatcgcgtt gcgggatca ccagccgggt ttggtacgga tatcgggggt    720
agtatccgtg ttcctgcgtc gttcaatgga ctgtatggga tacggccgtc tgtggggaga    780
atgccgtacg aggggcggc caattcgggc gatggacaga atactgtgtt gtcggttgtg    840
gggccgttgt ctccttcggc gagagggttg atattgctgt tcaagacggt gttggggca    900 atgccgtggt tgggagatcc tggtgtgttg gagattccct ggagggagga atcgtagag    960 gagacgagaa aattagtgca gggaaagcca gaggggctag cttttggaat attctacgat   1020
gatggtcagg taaagccgca gccaccggtc gagagagcga tgcggattgc tgcagagacg   1080
atcaagcgtc taggacataa gctcatcaat tgggaacccc cctctcacct aacagccgcc   1140
tccctcgcaa accgcgccta caacatggac ggcggcgccg acgtactcca aaacttcgcc   1200
ctgtccaacg aagccatcca cacctccgta gtaatcgacg catcaggatc cccccaaaag   1260
accgcactag agatcgccgc gctaaacgtc gagaagcgcg aataccagaa acaatacctt   1320
gactactgga acagcacggc gcaattgaca gggactggac gacccgtcga cgcggtcatt   1380
tgtccagtgg cgccgcatgc ggcgtgcatt ccggggaagt atgcgacgat cgggtatacg   1440
gcgtttatta atgtgttgga ttatacgagt gcggttgtgc cggttacgag tgctgatagg   1500
agggtggatg ttgtagggaa ggaaggaagg gagtattttg gggagttgga taggaagacc   1560 gaggggagt acgatgcgga tgtgtttgat ggggcgccgg ctgggattca gctctttgga   1620
agacggcttc aggaggagaa gattctggta ctggctgagt atcttggtga ggaattcaag   1680
aaggctagtg cttga                                                    1695
```

<210> SEQ ID NO 43
<211> LENGTH: 564
<212> TYPE: PRT
<213> ORGANISM: Aspergillus niger

<400> SEQUENCE: 43

Met Ala Leu Thr Ser Trp Glu Gln Thr Ala Ala Ala Lys Arg Gln Ser

-continued

```
1               5                   10                  15
Val Leu Asn Ala Ile Pro Glu Lys Trp Arg Ile Lys Gly Pro Ile Pro
                    20                  25                  30

Ala Pro Ser Glu Gln Arg Asp Val Thr Gly Pro Tyr Ile Gln Gln Phe
                35                  40                  45

Leu Ser Pro Arg Glu Val Glu Ile Thr Glu Thr Asp Ala Val Gly Ile
 50                  55                  60

Thr Glu Arg Thr Thr Thr Gly Gln Trp Thr Ala Val Glu Val Thr Glu
 65                  70                  75                  80

Ala Phe Cys His Arg Ala Ala Leu Ala His Gln Leu Val Asn Cys Leu
                    85                  90                  95

His Glu Ile Phe Phe Asp Ala Ala Leu Glu Thr Ala Arg Ile Leu Asp
                100                 105                 110

Asp His Tyr Thr Lys Thr Gly Lys Pro Leu Gly Pro Leu His Gly Leu
                115                 120                 125

Pro Val Ser Leu Lys Asp Gln Phe His Val Lys Gly Val Glu Thr Thr
                130                 135                 140

Met Gly Tyr Val Gly Trp Ile Asn Thr Phe Gln Gly Lys Thr Asn Asp
145                 150                 155                 160

Pro Arg Tyr Leu Thr His Glu Ser Glu Leu Val Lys Glu Leu Arg Ala
                165                 170                 175

Ala Gly Ala Val Leu Tyr Cys Lys Thr Ser Val Pro Met Thr Leu Met
                180                 185                 190

Ser Gly Glu Thr Met Asn Asn Ile Ile Thr Tyr Thr His Asn Pro Lys
                195                 200                 205

Asn Arg Leu Leu Ser Ser Gly Ser Ser Gly Gly Glu Gly Ala Leu
                210                 215                 220

Ile Ala Leu Arg Gly Ser Pro Ala Gly Phe Gly Thr Asp Ile Gly Gly
225                 230                 235                 240

Ser Ile Arg Val Pro Ala Ser Phe Asn Gly Leu Tyr Gly Ile Arg Pro
                245                 250                 255

Ser Val Gly Arg Met Pro Tyr Glu Gly Ala Ala Asn Ser Gly Asp Gly
                260                 265                 270

Gln Asn Thr Val Leu Ser Val Val Gly Pro Leu Ser Pro Ser Ala Arg
                275                 280                 285

Gly Leu Ile Leu Leu Phe Lys Thr Val Leu Gly Ala Met Pro Trp Leu
                290                 295                 300

Gly Asp Pro Gly Val Leu Glu Ile Pro Trp Arg Glu Glu Ile Val Glu
305                 310                 315                 320

Glu Thr Arg Lys Leu Val Gln Gly Lys Pro Glu Gly Leu Ala Phe Gly
                325                 330                 335

Ile Phe Tyr Asp Asp Gly Gln Val Lys Pro Gln Pro Pro Val Glu Arg
                340                 345                 350

Ala Met Arg Ile Ala Ala Glu Thr Ile Lys Arg Leu Gly His Lys Leu
                355                 360                 365

Ile Asn Trp Glu Pro Pro Ser His Leu Thr Ala Ala Ser Leu Ala Asn
                370                 375                 380

Arg Ala Tyr Asn Met Asp Gly Gly Ala Asp Val Leu Gln Asn Phe Ala
385                 390                 395                 400

Leu Ser Asn Glu Ala Ile His Thr Ser Val Val Ile Asp Ala Ser Gly
                405                 410                 415

Ser Pro Gln Lys Thr Ala Leu Glu Ile Ala Ala Leu Asn Val Glu Lys
                420                 425                 430
```

```
Arg Glu Tyr Gln Lys Gln Tyr Leu Asp Tyr Trp Asn Ser Thr Ala Gln
            435                 440                 445

Leu Thr Gly Thr Gly Arg Pro Val Asp Ala Val Ile Cys Pro Val Ala
450                 455                 460

Pro His Ala Ala Cys Ile Pro Gly Lys Tyr Ala Thr Ile Gly Tyr Thr
465                 470                 475                 480

Ala Phe Ile Asn Val Leu Asp Tyr Thr Ser Ala Val Val Pro Val Thr
                485                 490                 495

Ser Ala Asp Arg Arg Val Asp Val Gly Lys Glu Gly Arg Glu Tyr
                500                 505                 510

Phe Gly Glu Leu Asp Arg Lys Thr Glu Gly Glu Tyr Asp Ala Asp Val
            515                 520                 525

Phe Asp Gly Ala Pro Ala Gly Ile Gln Leu Phe Gly Arg Arg Leu Gln
530                 535                 540

Glu Glu Lys Ile Leu Val Leu Ala Glu Tyr Leu Gly Glu Glu Phe Lys
545                 550                 555                 560

Lys Ala Ser Ala

<210> SEQ ID NO 44
<211> LENGTH: 42
<212> TYPE: DNA
<213> ORGANISM: Artificial Sequence
<220> FEATURE:
<223> OTHER INFORMATION: primer

<400> SEQUENCE: 44
gtcctgttaa ttaaccttca ccatggccct cacatcctgg ga                    42

<210> SEQ ID NO 45
<211> LENGTH: 41
<212> TYPE: DNA
<213> ORGANISM: Artificial Sequence
<220> FEATURE:
<223> OTHER INFORMATION: primer

<400> SEQUENCE: 45
acttcaggcg cgcctttaag cactagcctt cttgaattcc t                     41

<210> SEQ ID NO 46
<211> LENGTH: 2017
<212> TYPE: DNA
<213> ORGANISM: Artificial Sequence
<220> FEATURE:
<223> OTHER INFORMATION: synthetic construct

<400> SEQUENCE: 46
gtcctgttaa ttaaccttca ccatggccct cacatcctgg gaacaaaccg cagcggccaa    60
acgccaatcc gtcctcaacg ccatccccga gaaatggcgc atcaagggtc ctatccccgc   120
accgtcggag cagcgcgacg taacaggccc ctacatccag cagttcctat ccccacgcga   180
ggttgaaatc accgaaacag cgccgtagg gatcacagag cgaactacaa cgggccagtg   240
gacagctgtg gaggtgaccg aggcgttctg ccatcgcgca gcattggcgc atcaactcgt   300
acattcccca tccacaagga gtgctagtct gcgctttact aatcgagaaa aggtaaact    360 gcttgcatga atcttcttc gatgccgcgc ttgaaaccgc cgcattcta gacgaccact    420 acaccaagac cggcaagcca ctcggtcccc ttcacggcct ccctgtcagt ctgaaggatc   480
aattccacgt caagggcgta gaaacaacca tgggttacgt cggctggata aacaccttcc   540
aaggcaagac caatgacccg cgctatctta cacacgaaag cgaactcgtt aagaactcc    600
```

```
gcgccgcggg agccgtcctc tactgcaaga ctagcgtccc catgacgttg atgtcaggtg      660
aaaccatgaa caatatcata acttacacac ataacccgaa gaacaggctt ctcagttctg      720
gaggtagttc cggggggcgaa ggagcactga tcgcgttgcg gggatcacca gccgggtttg      780
gtacggatat cgggggtagt atccgtgttc ctgcgtcgtt caatgactg tatgggatac       840 ggccgtctgt ggggagaatg ccgtacgagg gggcggccaa ttcggcgat ggacagaata       900 ctgtgttgtc ggttgtgggg ccgttgtctc cttcggcgag agggttgata ttgctgttca      960
agacggtgtt gggggcaatg ccgtggttgg agatcctgg tgtgttggag attccctgga      1020
gggaggaaat cgtagaggag acgagaaaat tagtgcaggg aaagccagag gggctagctt     1080
ttggaatatt ctacgatgat ggtcaggtaa agccgcagcc accggtcgag agagcgatgc     1140
ggattgctgc agagacgatc aagcgttag gacataaggt gagtgccctc cttcttcttg      1200
cgacactgct aacattcatc ccagctcatc aattgggaac cccctctca cctaacagcc      1260 gcctccctcg cagtaagtcc cccatccaac ccactacacc acaaccccct aacaataaac     1320
caacccccag aaccgcgcct acaacatgga cggcggcgcc gacgtactcc aaaacttcgc     1380
cctgtccaac gaagccatcc acacctccgt agtaatcgac gcatcaggat ccccccaaaa     1440
gaccgcacta gagatcgccg cgctaaacgt cgagaagcgc gaataccaga aacaatacct     1500
tgactactgg aacagcacgg cgcaattgac agggactgga cgacccgtcg acgcggtcat     1560
ttgtccagtg gcgccgcatg cggcgtgcat tccggggaag tatgcgacga tcgggtatac     1620
ggcgtttatt aatgtgttgg attatacgag tgcggttgtg ccggttacga gtgctgatag     1680
gagggtggat gttgtaggga aggaaggaag ggagtatttt ggggagttgg ataggaagac     1740 cgaggggggag tgtaagttct tcccttttctt ttcttcttttc ttttcattga gctatccaat   1800
ttggttggag gtcttgtgtg tttgtttgtt cggagagtgg tgatgggggtt atgtgctgac     1860 tggatgtttc tatctagacg atgcggatgt gtttgatggg gcgccggctg ggattcagct     1920
ctttggaaga cggcttcagg aggagaagat tctggtactg gctgagtatc ttggtgagga     1980
attcaagaag gctagtgctt aaaggcgcgc ctgaagt                              2017

<210> SEQ ID NO 47
<211> LENGTH: 50
<212> TYPE: DNA
<213> ORGANISM: Artificial Sequence
<220> FEATURE:
<223> OTHER INFORMATION: primer

<400> SEQUENCE: 47
acttcaggcg cgcctttaga gcttggaagc actagccttc ttgaattcct                  50

<210> SEQ ID NO 48
<211> LENGTH: 2026
<212> TYPE: DNA
<213> ORGANISM: Artificial Sequence
<220> FEATURE:
<223> OTHER INFORMATION: synthetic construct

<400> SEQUENCE: 48
gtcctgttaa ttaaccttca ccatggccct cacatcctgg gaacaaaccg cagcggccaa       60
acgccaatcc gtcctcaacg ccatccccga gaaatggcgc atcaagggtc ctatccccgc     120
accgtcggag cagcgcgacg taacaggccc ctacatccag cagttcctat ccccacgcga     180
ggttgaaatc accgaaacag acgccgtagg gatcacagag cgaactacaa cgggccagtg     240
gacagctgtg gaggtgaccg aggcgttctg ccatcgcgca gcattggcgc atcaactcgt     300
```

-continued

```
acattcccca tccacaagga gtgctagtct gcgctttact aatcgagaaa aaggtaaact    360
gcttgcatga aatcttcttc gatgccgcgc ttgaaaccgc ccgcattcta gacgaccact    420
acaccaagac cggcaagcca ctcggtcccc ttcacggcct ccctgtcagt ctgaaggatc    480
aattccacgt caagggcgta gaaacaacca tgggttacgt cggctggata aacaccttcc    540
aaggcaagac caatgacccg cgctatctta cacacgaaag cgaactcgtt aaagaactcc    600
gcgccgcggg agccgtcctc tactgcaaga ctagcgtccc catgacgttg atgtcaggtg    660
aaaccatgaa caatatcata acttacacac ataacccgaa gaacaggctt ctcagttctg    720
gaggtagttc cggggggcgaa ggagcactga tcgcgttgcg gggatcacca gccgggtttg    780
gtacggatat cgggggtagt atccgtgttc ctgcgtcgtt caatggactg tatgggatac    840
ggccgtctgt ggggagaatg ccgtacgagg gggcggccaa ttcgggcgat ggacagaata    900
ctgtgttgtc ggttgtgggg ccgttgtctc cttcggcgag agggttgata ttgctgttca    960
agacggtgtt gggggcaatg ccgtggttgg gagatcctgg tgtgttggag attccctgga    1020
gggaggaaat cgtagaggag acgagaaaat tagtgcaggg aaagccagag gggctagctt    1080
ttggaatatt ctacgatgat ggtcaggtaa agccgcagcc accggtcgag agagcgatgc    1140
ggattgctgc agagacgatc aagcgtctag acataaggt gagtgccctc cttcttcttg    1200
cgacactgct aacattcatc ccagctcatc aattgggaac cccctctca cctaacagcc    1260
gcctccctcg cagtaagtcc cccatccaac ccactacacc acaacccct aacaataaac    1320
caaccccag aaccgcgcct acaacatgga cggcggcgcc gacgtactcc aaaacttcgc    1380
cctgtccaac gaagccatcc acacctccgt agtaatcgac gcatcaggat cccccaaaa    1440
gaccgcacta gagatcgccg cgctaaacgt cgagaagcgc gaataccaga aacaatacct    1500
tgactactgg aacagcacgg cgcaattgac agggactgga cgacccgtcg acgcggtcat    1560
ttgtccagtg gcgccgcatg cggcgtgcat tccggggaag tatgcgacga tcgggtatac    1620
ggcgtttatt aatgtgttgg attatacgag tgcggttgtg ccggttacga gtgctgatag    1680
gagggtggat gttgtaggga aggaaggaag ggagtatttt ggggagttgg ataggaagac    1740
cgaggggag tgtaagttct tcccttttctt ttcttcttttc ttttcattga gctatccaat    1800
ttggttggag gtcttgtgtg tttgtttgtt cggagagtgg tgatgggggtt atgtgctgac    1860
tggatgtttc tatctagacg atgcggatgt gtttgatggg gcgccggctg ggattcagct    1920
ctttggaaga cggcttcagg aggagaagat tctggtactg gctgagtatc ttggtgagga    1980
attcaagaag gctagtgctt ccaagctcta aggcgcgcc tgaagt                    2026
```

<210> SEQ ID NO 49
<211> LENGTH: 567
<212> TYPE: PRT
<213> ORGANISM: Artificial Sequence
<220> FEATURE:
<223> OTHER INFORMATION: synthetic construct

<400> SEQUENCE: 49

```
Met Ala Leu Thr Ser Trp Glu Gln Thr Ala Ala Lys Arg Gln Ser
1               5                   10                  15

Val Leu Asn Ala Ile Pro Glu Lys Trp Arg Ile Lys Gly Pro Ile Pro
            20                  25                  30

Ala Pro Ser Glu Gln Arg Asp Val Thr Gly Pro Tyr Ile Gln Gln Phe
        35                  40                  45

Leu Ser Pro Arg Glu Val Glu Ile Thr Glu Thr Asp Ala Val Gly Ile
    50                  55                  60
```

```
Thr Glu Arg Thr Thr Thr Gly Gln Trp Thr Ala Val Glu Val Thr Glu
 65                  70                  75                  80

Ala Phe Cys His Arg Ala Ala Leu Ala His Gln Leu Val Asn Cys Leu
                 85                  90                  95

His Glu Ile Phe Phe Asp Ala Ala Leu Glu Thr Ala Arg Ile Leu Asp
            100                 105                 110

Asp His Tyr Thr Lys Thr Gly Lys Pro Leu Gly Pro Leu His Gly Leu
        115                 120                 125

Pro Val Ser Leu Lys Asp Gln Phe His Val Lys Gly Val Glu Thr Thr
130                 135                 140

Met Gly Tyr Val Gly Trp Ile Asn Thr Phe Gln Gly Lys Thr Asn Asp
145                 150                 155                 160

Pro Arg Tyr Leu Thr His Glu Ser Glu Leu Val Lys Glu Leu Arg Ala
                165                 170                 175

Ala Gly Ala Val Leu Tyr Cys Lys Thr Ser Val Pro Met Thr Leu Met
            180                 185                 190

Ser Gly Glu Thr Met Asn Asn Ile Ile Thr Tyr Thr His Asn Pro Lys
        195                 200                 205

Asn Arg Leu Leu Ser Ser Gly Ser Ser Gly Glu Gly Ala Leu
210                 215                 220

Ile Ala Leu Arg Gly Ser Pro Ala Gly Phe Gly Thr Asp Ile Gly Gly
225                 230                 235                 240

Ser Ile Arg Val Pro Ala Ser Phe Asn Gly Leu Tyr Gly Ile Arg Pro
                245                 250                 255

Ser Val Gly Arg Met Pro Tyr Glu Gly Ala Ala Asn Ser Gly Asp Gly
            260                 265                 270

Gln Asn Thr Val Leu Ser Val Val Gly Pro Leu Ser Pro Ser Ala Arg
        275                 280                 285

Gly Leu Ile Leu Leu Phe Lys Thr Val Leu Gly Ala Met Pro Trp Leu
290                 295                 300

Gly Asp Pro Gly Val Leu Glu Ile Pro Trp Arg Glu Glu Ile Val Glu
305                 310                 315                 320

Glu Thr Arg Lys Leu Val Gln Gly Lys Pro Glu Gly Leu Ala Phe Gly
                325                 330                 335

Ile Phe Tyr Asp Asp Gly Gln Val Lys Pro Gln Pro Val Glu Arg
            340                 345                 350

Ala Met Arg Ile Ala Ala Glu Thr Ile Lys Arg Leu Gly His Lys Leu
        355                 360                 365

Ile Asn Trp Glu Pro Pro Ser His Leu Thr Ala Ala Ser Leu Ala Asn
370                 375                 380

Arg Ala Tyr Asn Met Asp Gly Gly Ala Asp Val Leu Gln Asn Phe Ala
385                 390                 395                 400

Leu Ser Asn Glu Ala Ile His Thr Ser Val Val Ile Asp Ala Ser Gly
                405                 410                 415

Ser Pro Gln Lys Thr Ala Leu Glu Ile Ala Ala Leu Asn Val Glu Lys
            420                 425                 430

Arg Glu Tyr Gln Lys Gln Tyr Leu Asp Tyr Trp Asn Ser Thr Ala Gln
        435                 440                 445

Leu Thr Gly Thr Gly Arg Pro Val Asp Ala Val Ile Cys Pro Val Ala
450                 455                 460

Pro His Ala Ala Cys Ile Pro Gly Lys Tyr Ala Thr Ile Gly Tyr Thr
465                 470                 475                 480

Ala Phe Ile Asn Val Leu Asp Tyr Thr Ser Ala Val Val Pro Val Thr
                485                 490                 495
```

Ser Ala Asp Arg Arg Val Asp Val Gly Lys Glu Gly Arg Glu Tyr
            500                 505                 510

Phe Gly Glu Leu Asp Arg Lys Thr Glu Gly Glu Tyr Asp Ala Asp Val
            515                 520                 525

Phe Asp Gly Ala Pro Ala Gly Ile Gln Leu Phe Gly Arg Arg Leu Gln
            530                 535                 540

Glu Glu Lys Ile Leu Val Leu Ala Glu Tyr Leu Gly Glu Glu Phe Lys
545                 550                 555                 560

Lys Ala Ser Ala Ser Lys Leu
                565

<210> SEQ ID NO 50
<211> LENGTH: 1953
<212> TYPE: DNA
<213> ORGANISM: Aspergillus nidulans

<400> SEQUENCE: 50

```
atgcctcaat cctgggaaga actggccgct gataagcgcg cccgcctcgc aaaaaccatc     60
cctgatgaat ggaaagtcca gacgctgcct gcggaagaca gcgttattga tttcccaaag    120
aaatcgggga tcctttcaga ggccgaactg aagatcacag aggcctccgc tgcagatctt    180
gtgtccaagc tggcggccgg agagttgacc tcggtggaag ttacgctagc attctgtaaa    240
cgggcagcaa tcgcccagca gttagtaggg tcccctctac ctctcaggga gatgtaacaa    300
cgccacctta tgggactatc aagctgacgc tggcttctgt gcagacaaac tgcgcccacg    360
agttcttccc tgacgccgct ctcgcgcagg caagggaact cgatgaatac tacgcaaagc    420
acaagagacc cgttggtcca ctccatggcc tccccatctc tctcaaagac cagcttcgag    480
tcaaggtaca ccgttgcccc taagtcgtta gatgtcccct tttgtcagct aacatatgcc    540
accagggcta cgaaacatca atgggctaca tctcatggct aaacaagtac gacgaagggg    600
actcggttct gacaaccatg ctccgcaaag ccggtgccgt cttctacgtc aagacctctg    660
tcccgcagac cctgatggtc tgcgagacag tcaacaacat catcgggcgc accgtcaacc    720
cacgcaacaa gaactggtcg tgcggcggca gttctggtgg tgagggtgcg atcgttggga    780
ttcgtggtgg cgtcatcggt gtaggaacgg atatcggtgg ctcgattcga gtgccggccg    840
cgttcaactt cctgtacggt ctaaggccga gtcatgggcg gctgccgtat gcaaagatgg    900
cgaacagcat ggagggtcag gagacggtgc acagcgttgt cgggccgatt acgcactctg    960
ttgagggtga gtccttcgcc tcttccttct tttcctgctc tataccaggc ctccactgtc   1020
ctcctttctt gcttttttata ctatatacga gaccggcagt cactgatgaa gtatgttaga   1080
cctccgcctc ttaccaaaat ccgtcctcgg tcaggagcca tggaaatacg actccaaggt   1140
catccccatg ccctggcgcc agtccgagtc ggacattatt gcctccaaga tcaagaacgg   1200
cgggctcaat atcggctact acaacttcga cggcaatgtc cttccacacc ctcctatcct   1260
gcgcggcgtg gaaaccaccg tcgccgcact cgccaaagcc ggtcacaccg tgaccccgtg   1320
gacgccatac aagcacgatt tcggccacga tctcatctcc catatctacg cggctgacgg   1380
cagcgccgac gtaatgcgcg atatcagtgc atccggcgag ccggcgattc caaatatcaa   1440
agacctactg aacccgaaca tcaaagctgt taacatgaac gagctctggg acacgcatct   1500
ccagaagtgg aattaccaga tggagtacct tgagaaatgg cgggaggctg aagaaaaggc   1560
cgggaaggaa ctggacgcca tcatcgcgcc gattacgcct accgctgcgg tacggcatga   1620
ccagttccgg tactatgggt atgcctctgt gatcaacctg ctggatttca cgagcgtggt   1680
```

```
tgttccggtt accttttgcgg ataagaacat cgataagaag aatgagagtt tcaaggcggt    1740
tagtgagctt gatgccctcg tgcaggaaga gtatgatccg gaggcgtacc atggggcacc    1800
ggttgcagtg caggttatcg gacggagact cagtgaagag aggacgttgg cgattgcaga    1860
ggaagtgggg aagttgctgg gaaatgtggt gactccatag ctaataagtg tcagatagca    1920
atttgcacaa gaaatcaata ccagcaactg taa                                 1953

<210> SEQ ID NO 51
<211> LENGTH: 1524
<212> TYPE: DNA
<213> ORGANISM: Aspergillus nidulans

<400> SEQUENCE: 51
atgcctcaat cctgggaaga actggccgct gataagcgcg cccgcctcgc aaaaaccatc      60
cctgatgaat ggaaagtcca gacgctgcct gcggaagaca gcgttattga tttcccaaag     120
aaatcgggga tcctttcaga ggccgaactg aagatcacag aggcctccgc tgcagatctt     180
gtgtccaagc tggcggccgg agagttgacc tcggtggaag ttacgctagc attctgtaaa     240
cgggcagcaa tcgcccagca gttaacaaac tgcgcccacg agttcttccc tgacgccgct     300
ctcgcgcagg caagggaact cgatgaatac tacgcaaagc acaagagacc cgttggtcca     360
ctccatggcc tccccatctc tctcaaagac cagcttcgag tcaagggcta cgaaacatca     420
atgggctaca tctcatggct aaacaagtac gacgaagggg actcggttct gacaaccatg     480
ctccgcaaag ccggtgccgt cttctacgtc aagacctctg tcccgcagac cctgatggtc     540
tgcgagacag tcaacaacat catcgggcgc accgtcaacc cacgcaacaa gaactggtcg     600
tgcggcggca gttctggtgg tgagggtgcg atcgttggga ttcgtggtgg cgtcatcggt     660
gtaggaacgg atatcggtgg ctcgattcga gtgccggccg cgttcaactt cctgtacggt     720
ctaaggccga gtcatgggcg gctgccgtat gcaaagatgg cgaacagcat ggagggtcag     780
gagacggtgc acagcgttgt cgggccgatt acgcactctg ttgaggacct ccgcctcttc     840
accaaatccg tcctcggtca ggagccatgg aaatacgact ccaaggtcat ccccatgccc     900
tggcgccagt ccgagtcgga cattattgcc tccaagatca gaacggcgg gctcaatatc      960 ggctactaca acttcgacgg caatgtcctt ccacaccctc ctatcctgcg cggcgtggaa    1020
accaccgtcg ccgcactcgc caaagccggt cacaccgtga ccccgtggac gccatacaag    1080
cacgatttcg ccacgatct catctcccat atctacgcgg ctgacggcag cgccgacgta    1140
atgcgcgata tcagtgcatc cggcgagccg gcgattccaa atatcaaaga cctactgaac    1200
ccgaacatca aagctgttaa catgaacgag ctctgggaca cgcatctcca gaagtggaat    1260
taccagatgg agtaccttga gaatggcgg gaggctgaag aaaaggccgg gaaggaactg    1320
gacgccatca tcgcgccgat tacgcctacc gctgcggtac ggcatgacca gttccggtac    1380
tatgggtatg cctctgtgat caacctgctg gatttcacga gcgtggttgt tccggttacc    1440
tttgcggata gaacatcga taagaagaat gagagtttca aggcgatagc aatttgcaca    1500
agaaatcaat accagcaact gtaa                                           1524

<210> SEQ ID NO 52
<211> LENGTH: 507
<212> TYPE: PRT
<213> ORGANISM: Aspergillus nidulans

<400> SEQUENCE: 52

Met Pro Gln Ser Trp Glu Glu Leu Ala Ala Asp Lys Arg Ala Arg Leu
1               5                   10                  15
```

```
Ala Lys Thr Ile Pro Asp Glu Trp Lys Val Gln Thr Leu Pro Ala Glu
             20                  25                  30
Asp Ser Val Ile Asp Phe Pro Lys Lys Ser Gly Ile Leu Ser Glu Ala
         35                  40                  45
Glu Leu Lys Ile Thr Glu Ala Ser Ala Ala Asp Leu Val Ser Lys Leu
 50                  55                  60
Ala Ala Gly Glu Leu Thr Ser Val Glu Val Thr Leu Ala Phe Cys Lys
 65                  70                  75                  80
Arg Ala Ala Ile Ala Gln Gln Leu Thr Asn Cys Ala His Glu Phe Phe
                 85                  90                  95
Pro Asp Ala Ala Leu Ala Gln Ala Arg Glu Leu Asp Glu Tyr Tyr Ala
                100                 105                 110
Lys His Lys Arg Pro Val Gly Pro Leu His Gly Leu Pro Ile Ser Leu
            115                 120                 125
Lys Asp Gln Leu Arg Val Lys Gly Tyr Glu Thr Ser Met Gly Tyr Ile
130                 135                 140
Ser Trp Leu Asn Lys Tyr Asp Glu Gly Asp Ser Val Leu Thr Thr Met
145                 150                 155                 160
Leu Arg Lys Ala Gly Ala Val Phe Tyr Val Lys Thr Ser Val Pro Gln
                165                 170                 175
Thr Leu Met Val Cys Glu Thr Val Asn Asn Ile Ile Gly Arg Thr Val
            180                 185                 190
Asn Pro Arg Asn Lys Asn Trp Ser Cys Gly Gly Ser Ser Gly Gly Glu
            195                 200                 205
Gly Ala Ile Val Gly Ile Arg Gly Gly Val Ile Gly Val Gly Thr Asp
210                 215                 220
Ile Gly Gly Ser Ile Arg Val Pro Ala Ala Phe Asn Phe Leu Tyr Gly
225                 230                 235                 240
Leu Arg Pro Ser His Gly Arg Leu Pro Tyr Ala Lys Met Ala Asn Ser
                245                 250                 255
Met Glu Gly Gln Glu Thr Val His Ser Val Val Gly Pro Ile Thr His
            260                 265                 270
Ser Val Glu Asp Leu Arg Leu Phe Thr Lys Ser Val Leu Gly Gln Glu
        275                 280                 285
Pro Trp Lys Tyr Asp Ser Lys Val Ile Pro Met Pro Trp Arg Gln Ser
    290                 295                 300
Glu Ser Asp Ile Ile Ala Ser Lys Ile Lys Asn Gly Leu Asn Ile
305                 310                 315                 320
Gly Tyr Tyr Asn Phe Asp Gly Asn Val Leu Pro His Pro Ile Leu
                325                 330                 335
Arg Gly Val Glu Thr Thr Val Ala Ala Leu Ala Lys Ala Gly His Thr
            340                 345                 350
Val Thr Pro Trp Thr Pro Tyr Lys His Asp Phe Gly His Asp Leu Ile
        355                 360                 365
Ser His Ile Tyr Ala Ala Asp Gly Ser Ala Asp Val Met Arg Asp Ile
    370                 375                 380
Ser Ala Ser Gly Glu Pro Ala Ile Pro Asn Ile Lys Asp Leu Leu Asn
385                 390                 395                 400
Pro Asn Ile Lys Ala Val Asn Met Asn Glu Leu Trp Asp Thr His Leu
                405                 410                 415
Gln Lys Trp Asn Tyr Gln Met Glu Tyr Leu Glu Lys Trp Arg Glu Ala
            420                 425                 430
Glu Glu Lys Ala Gly Lys Glu Leu Asp Ala Ile Ile Ala Pro Ile Thr
```

```
                435                 440                 445
Pro Thr Ala Ala Val Arg His Asp Gln Phe Arg Tyr Tyr Gly Tyr Ala
        450                 455                 460

Ser Val Ile Asn Leu Leu Asp Phe Thr Ser Val Val Pro Val Thr
465                 470                 475                 480

Phe Ala Asp Lys Asn Ile Asp Lys Lys Asn Glu Ser Phe Lys Ala Ile
                485                 490                 495

Ala Ile Cys Thr Arg Asn Gln Tyr Gln Gln Leu
        500                 505

<210> SEQ ID NO 53
<211> LENGTH: 44
<212> TYPE: DNA
<213> ORGANISM: Artificial Sequence
<220> FEATURE:
<223> OTHER INFORMATION: primer

<400> SEQUENCE: 53
gtcctgttaa ttaaccttca ccatgcctca atcctgggaa gaac                       44

<210> SEQ ID NO 54
<211> LENGTH: 39
<212> TYPE: DNA
<213> ORGANISM: primer

<400> SEQUENCE: 54
acttcaggcg cgcctttatg gagtcaccac atttcccag                              39

<210> SEQ ID NO 55
<211> LENGTH: 1939
<212> TYPE: DNA
<213> ORGANISM: Artificial Sequence
<220> FEATURE:
<223> OTHER INFORMATION: synthetic product

<400> SEQUENCE: 55
gtcctgttaa ttaaccttca ccatgcctca atcctgggaa gaactggccg ctgataagcg     60
cgcccgcctc gcaaaaacca tccctgatga atggaaagtc cagacgctgc ctgcggaaga    120
cagcgttatt gatttcccaa agaaatcggg gatcctttca gaggccgaac tgaagatcac    180
agaggcctcc gctgcagaga tcttgtgtcc aagctggcgg ccggagagtt gacctcggtg    240
gaagttacgc tagcattctg taaacgggca gcaatcgccc agcagttagt agggtcccct    300
ctacctctca gggagatgta acaacgccac cttatggac tatcaagctg acgctggctt     360
ctgtgcagac aaactgcgcc cacgagttct ccctgacgc cgctctcgcg caggcaaggg    420
aactcgatga atactacgca aagcacaaga gacccgttgg tccactccat ggcctcccca    480
tctctctcaa agaccagctt cgagtcaagg tacaccgttg cccctaagtc gttagatgtc    540
ccttttttgtc agctaacata tgccaccagg gctacgaaac atcaatgggc tacatctcat    600
ggctaaacaa gtacgacgaa ggggactcgg ttctgacaac catgctccgc aaagccggtg    660
ccgtcttcta cgtcaagacc tctgtcccgc agaccctgat ggtctgcgag acagtcaaca    720
acatcatcgg gcgcaccgtc aacccacgca acaagaactg gtcgtgcggc ggcagttctg    780
gtggtgaggg tgcgatcgtt gggattcgtg gtggcgtcat cggtgtagga acggatatcg    840
gtggctcgat tcgagtgccg gccgcgttca acttcctgta cggtctaagg ccgagtcatg    900
ggcggctgcc gtatgcaaag atggcgaaca gcatggaggg tcaggagacg gtgcacagcg    960
ttgtcgggcc gattacgcac tctgttgagg gtgagtcctt cgcctcttcc ttctttttcct  1020
```

```
gctctatacc aggcctccac tgtcctcctt tcttgctttt tatactatat acgagaccgg   1080
cagtcactga tgaagtatgt tagacctccg cctcttcacc aaatccgtcc tcggtcagga   1140
gccatggaaa tacgactcca aggtcatccc catgccctgg cgccagtccg agtcggacat   1200
tattgcctcc aagatcaaga acggcgggct caatatcggc tactacaact tcgacggcaa   1260
tgtccttcca caccctccta tcctgcgcgg cgtggaaacc accgtcgccg cactcgccaa   1320
agccggtcac accgtgaccc cgtggacgcc atacaagcac gatttcggcc acgatctcat   1380
ctcccatatc tacgcggctg acggcagcgc cgacgtaatg cgcgatatca gtgcatccgg   1440
cgagccggcg attccaaata tcaaagacct actgaacccg aacatcaaag ctgttaacat   1500
gaacgagctc tgggacacgc atctccagaa gtggaattac cagatggagt accttgagaa   1560
atggcgggag gctgaagaaa aggccgggaa ggaactggac gccatcatcg cgccgattac   1620
gcctaccgct gcggtacggc atgaccagtt ccggtactat gggtatgcct ctgtgatcaa   1680
cctgctggat ttcacgagcg tggttgttcc ggttaccttt gcggataaga acatcgataa   1740
gaagaatgag agtttcaagg cggttagtga gcttgatgcc ctcgtgcagg aagagtatga   1800
tccggaggcg taccatgggg caccggttgc agtgcaggtt atcggacgga gactcagtga   1860
agagaggacg ttggcgattg cagaggaagt ggggaagttg ctgggaaatg tggtgactcc   1920
ataaaggcgc gcctgaagt                                                1939

<210> SEQ ID NO 56
<211> LENGTH: 48
<212> TYPE: DNA
<213> ORGANISM: Artificial Sequence
<220> FEATURE:
<223> OTHER INFORMATION: primer

<400> SEQUENCE: 56
acttcaggcg cgcctttaga gcttggatgg agtcaccaca tttcccag                48

<210> SEQ ID NO 57
<211> LENGTH: 1948
<212> TYPE: DNA
<213> ORGANISM: Artificial Sequence
<220> FEATURE:
<223> OTHER INFORMATION: synthetic product

<400> SEQUENCE: 57
gtcctgttaa ttaaccttca ccatgcctca tcctgggaa gaactggccg ctgataagcg    60
cgcccgcctc gcaaaaacca tccctgatga atggaaagtc cagacgctgc ctgcggaaga   120
cagcgttatt gatttcccaa agaaatcggg gatcctttca gaggccgaac tgaagatcac   180
agaggcctcc gctgcagaga tcttgtgtcc aagctggcgg ccggagagtt gacctcggtg   240
gaagttacgc tagcattctg taaacgggca gcaatcgccc agcagttagt agggtcccct   300
ctacctctca gggagatgta acaacgccac cttatgggac tatcaagctg acgctggctt   360
ctgtgcagac aaactgcgcc cacgagttct tccctgacgc cgctctcgcg caggcaaggg   420
aactcgatga atactacgca aagcacaaga gaccgttgg tccactccat ggcctcccca   480
tctctctcaa agaccagctt cgagtcaagg tacaccgttg cccctaagtc gttagatgtc   540 ccttttgtc agctaacata tgccaccagg gctacgaaac atcaatgggc tacatctcat   600
ggctaaacaa gtacgacgaa ggggactcgg ttctgacaac catgctccgc aaagccggtg   660
ccgtcttcta cgtcaagacc tctgtcccgc agacctgat ggtctgcgag acagtcaaca   720
acatcatcgg gcgcaccgtc aacccacgca acaagaactg gtcgtgcggc ggcagttctg   780
```

```
gtggtgaggg tgcgatcgtt gggattcgtg gtggcgtcat cggtgtagga acggatatcg    840
gtggctcgat tcgagtgccg gccgcgttca acttcctgta cggtctaagg ccgagtcatg    900
ggcggctgcc gtatgcaaag atggcgaaca gcatggaggg tcaggagacg gtgcacagcg    960
ttgtcgggcc gattacgcac tctgttgagg gtgagtcctt cgcctcttcc ttcttttcct   1020
gctctatacc aggcctccac tgtcctcctt tcttgctttt tatactatat acgagaccgg   1080
cagtcactga tgaagtatgt tagacctccg cctcttcacc aaatccgtcc tcggtcagga   1140
gccatggaaa tacgactcca aggtcatccc catgccctgg cgccagtccg agtcggacat   1200
tattgcctcc aagatcaaga acggcgggct caatatcggc tactacaact cgacggcaa    1260
tgtccttcca caccctccta tcctgcgcgg cgtggaaacc accgtcgccg cactcgccaa   1320
agccggtcac accgtgaccc cgtggacgcc atacaagcac gatttcggcc acgatctcat   1380
ctcccatatc tacgcggctg acggcagcgc cgacgtaatg cgcgatatca gtgcatccgg   1440
cgagccggcg attccaaata tcaaagacct actgaacccg aacatcaaag ctgttaacat   1500
gaacgagctc tgggacacgc atctccagaa gtggaattac cagatggagt accttgagaa   1560
atggcgggag gctgaagaaa aggccgggaa ggaactggac gccatcatcg cgccgattac   1620
gcctaccgct gcggtacggc atgaccagtt ccggtactat gggtatgcct ctgtgatcaa   1680
cctgctggat ttcacgagcg tggttgttcc ggttaccttt gcggataaga acatcgataa   1740
gaagaatgag agtttcaagg cggttagtga gcttgatgcc ctcgtgcagg aagagtatga   1800
tccggaggcg taccatgggg caccggttgc agtgcaggtt atcggacgga gactcagtga   1860
agagaggacg ttggcgattg cagaggaagt ggggaagttg ctgggaaatg tggtgactcc   1920
atccaagctc taaaggcgcg cctgaagt                                      1948
```

<210> SEQ ID NO 58
<211> LENGTH: 551
<212> TYPE: PRT
<213> ORGANISM: Artificial Sequence
<220> FEATURE:
<223> OTHER INFORMATION: synthetic product

<400> SEQUENCE: 58

```
Met Pro Gln Ser Trp Glu Glu Leu Ala Ala Asp Lys Arg Ala Arg Leu
1               5                   10                  15

Ala Lys Thr Ile Pro Asp Glu Trp Lys Val Gln Thr Leu Pro Ala Glu
            20                  25                  30

Asp Ser Val Ile Asp Phe Pro Lys Lys Ser Gly Ile Leu Ser Glu Ala
        35                  40                  45

Glu Leu Lys Ile Thr Glu Ala Ser Ala Ala Asp Leu Val Ser Lys Leu
    50                  55                  60

Ala Ala Gly Glu Leu Thr Ser Val Glu Val Thr Leu Ala Phe Cys Lys
65                  70                  75                  80

Arg Ala Ala Ile Ala Gln Gln Leu Thr Asn Cys Ala His Glu Phe Phe
                85                  90                  95

Pro Asp Ala Ala Leu Ala Gln Ala Arg Glu Leu Asp Glu Tyr Tyr Ala
            100                 105                 110

Lys His Lys Arg Pro Val Gly Pro Leu His Gly Leu Pro Ile Ser Leu
        115                 120                 125

Lys Asp Gln Leu Arg Val Lys Gly Tyr Glu Thr Ser Met Gly Tyr Ile
    130                 135                 140

Ser Trp Leu Asn Lys Tyr Asp Glu Gly Asp Ser Val Leu Thr Thr Met
145                 150                 155                 160
```

```
Leu Arg Lys Ala Gly Ala Val Phe Tyr Val Lys Thr Ser Val Pro Gln
            165                 170                 175

Thr Leu Met Val Cys Glu Thr Val Asn Asn Ile Ile Gly Arg Thr Val
        180                 185                 190

Asn Pro Arg Asn Lys Asn Trp Ser Cys Gly Ser Ser Gly Gly Glu
        195                 200                 205

Gly Ala Ile Val Gly Ile Arg Gly Val Ile Gly Val Gly Thr Asp
        210                 215                 220

Ile Gly Gly Ser Ile Arg Val Pro Ala Ala Phe Asn Phe Leu Tyr Gly
225                 230                 235                 240

Leu Arg Pro Ser His Gly Arg Leu Pro Tyr Ala Lys Met Ala Asn Ser
            245                 250                 255

Met Glu Gly Gln Glu Thr Val His Ser Val Val Gly Pro Ile Thr His
            260                 265                 270

Ser Val Glu Asp Leu Arg Leu Phe Thr Lys Ser Val Leu Gly Gln Glu
            275                 280                 285

Pro Trp Lys Tyr Asp Ser Lys Val Ile Pro Met Pro Trp Arg Gln Ser
        290                 295                 300

Glu Ser Asp Ile Ile Ala Ser Lys Ile Lys Asn Gly Gly Leu Asn Ile
305                 310                 315                 320

Gly Tyr Tyr Asn Phe Asp Gly Asn Val Leu Pro His Pro Ile Leu
            325                 330                 335

Arg Gly Val Glu Thr Thr Val Ala Ala Leu Ala Lys Ala Gly His Thr
            340                 345                 350

Val Thr Pro Trp Thr Pro Tyr Lys His Asp Phe Gly His Asp Leu Ile
            355                 360                 365

Ser His Ile Tyr Ala Ala Asp Gly Ser Ala Asp Val Met Arg Asp Ile
            370                 375                 380

Ser Ala Ser Gly Glu Pro Ala Ile Pro Asn Ile Lys Asp Leu Leu Asn
385                 390                 395                 400

Pro Asn Ile Lys Ala Val Asn Met Asn Glu Leu Trp Asp Thr His Leu
            405                 410                 415

Gln Lys Trp Asn Tyr Gln Met Glu Tyr Leu Glu Lys Trp Arg Glu Ala
            420                 425                 430

Glu Glu Lys Ala Gly Lys Glu Leu Asp Ala Ile Ile Ala Pro Ile Thr
            435                 440                 445

Pro Thr Ala Ala Val Arg His Asp Gln Phe Arg Tyr Tyr Gly Tyr Ala
        450                 455                 460

Ser Val Ile Asn Leu Leu Asp Phe Thr Ser Val Val Pro Val Thr
465                 470                 475                 480

Phe Ala Asp Lys Asn Ile Asp Lys Lys Asn Glu Ser Phe Lys Ala Val
            485                 490                 495

Ser Glu Leu Asp Ala Leu Val Gln Glu Tyr Asp Pro Glu Ala Tyr
        500                 505                 510

His Gly Ala Pro Val Ala Val Gln Val Ile Gly Arg Arg Leu Ser Glu
        515                 520                 525

Glu Arg Thr Leu Ala Ile Ala Glu Glu Val Gly Lys Leu Leu Gly Asn
        530                 535                 540

Val Val Thr Pro Ser Lys Leu
545                 550

<210> SEQ ID NO 59
<211> LENGTH: 1387
<212> TYPE: DNA
<213> ORGANISM: Aspergillus niger
```

<400> SEQUENCE: 59

```
atggcaccct ccacggtaac ccatgattct accatcctcg tggtgggagc gggtgtatgg      60
ggttgttcta ctgctttgca tttggctcgt cgcggatata agcatgtcac ggttctagac     120
ccctacacgg tcccatccgc aatcgcagcc ggcaatgata tcaacaagat catggaacac     180
aaggagccca aggtatgtc tgcaccgttc agccaatgac catcttccaa cgctaacaac     240
tccaacagca ggcgaagaaa gtccacgcag cattgcgttc gcgacgtgca ctcgtgccgc     300
tctgaaagcg tggcggacgg atcctgtttt caagcagtac tttcatgaga ccggtgtcat     360
agtatccggt cataccccgg cactcattga gcacatccgc aaagacgaaa tcgagtcatc     420
tgatgcagac tttgtcgaat tgaagacagc agaagacttc cgaaagacaa tgcctccagg     480
tgttctcact ggtgagtttc ctggctggaa gggctggttg aacaagtcgg gtgccggctg     540
gattcatgcc aagaaagcca tgatctctgc gtacactgaa gccaagcgtc ttggggtcaa     600
cttcatcact ggatctcccc aggggaacgt tgtatcacta gtatacgaga atggagatgt     660
ggttggagct aaaacgtccg atggggtcat tcatcgagca gaccaaacca ttttggcagc     720
cggtgcggga agtgaccgtc tcctggattt caagaaacag ctgcgtccta ctgcctggac     780
gctctctcat attcagatga cccctgagga ggccaagcag tacaaggatt tacccgtgct     840
tttcaatatt gcgaagggt tcttcatgga gcctgatgag gataagcacg aactgaagat     900
ctgtgacgag catcctggat actgtaactt tattccagac cctgcaagat ccggcgagat     960
cagaagcatc ccatttgcga agcatcaaat tcccctggag gccgaagctc gcgttaagga    1020
cttcctgcgg gatacaatgc cacacttggc cgaccgtccg ctggtatttg cccgtatctg    1080
ctgggatgct gacacggtag atcgcgcctt tttgatcgat aaacatcctg accacccttc    1140
actgctggtc gccgtgggag cttctgggaa cggggctatg cagatgccca ctattggagg    1200
gttcattgtg gatgcactgg agggtcacct acaagatgag ctaaaacatg tcgttcggtg    1260
gaggccagaa acagcggtcg acagagactg gaagtcgaca cagaaccgtt tcggaggacc    1320
agatgcggtt atggacttcc agacggttgg cgaaactgaa tggaccaaga tcaagagccg    1380
gctatag                                                              1387
```

<210> SEQ ID NO 60
<211> LENGTH: 1332
<212> TYPE: DNA
<213> ORGANISM: Aspergillus niger

<400> SEQUENCE: 60

```
atggcaccct ccacggtaac ccatgattct accatcctcg tggtgggagc gggtgtatgg      60
ggttgttcta ctgctttgca tttggctcgt cgcggatata agcatgtcac ggttctagac     120
ccctacacgg tcccatccgc aatcgcagcc ggcaatgata tcaacaagat catggaacac     180
aaggagccca aagcaggcga agaaagtcca cgcagcattg cgttcgcgac gtgcactcgt     240
gccgctctga aagcgtggcg gacggatcct gttttcaagc agtactttca tgagaccggt     300
gtcatagtat ccggtcatac cccggcactc attgagcaca tccgcaaaga cgaaatcgag     360
tcatctgatg cagactttgt cgaattgaag acagcagaag acttccgaaa gacaatgcct     420
ccaggtgttc tcactggtga gtttcctggc tggaagggct ggttgaacaa gtcgggtgcc     480
ggctggattc atgccaagaa agccatgatc tctgcgtaca ctgaagccaa gcgtcttggg     540
gtcaacttca tcactggatc tccccagggg aacgttgtat cactagtata cgagaatgga     600
gatgtggttg gagctaaaac gtccgatggg gtcattcatc gagcagacca aaccattttg     660
```

```
gcagccggtg cgggaagtga ccgtctcctg gatttcaaga aacagctgcg tcctactgcc   720
tggacgctct ctcatattca gatgacccct gaggaggcca agcagtacaa ggatttaccc   780
gtgcttttca atattgcgaa ggggttcttc atggagcctg atgaggataa gcacgaactg   840
aagatctgtg acgagcatcc tggatactgt aactttattc cagaccctgc aagatccggc   900
gagatcagaa gcatcccatt tgcgaagcat caaattcccc tggaggccga agctcgcgtt   960
aaggacttcc tgcgggatac aatgccacac ttggccgacc gtccgctggt atttgcccgt  1020
atctgctggg atgctgacac ggtagatcgc gccttttga tcgataaaca tcctgaccac  1080
ccttcactgc tggtcgccgt gggagcttct gggaacgggg ctatgcagat gcccactatt  1140
ggagggttca ttgtggatgc actggagggt cacctacaag atgagctaaa acatgtcgtt  1200
cggtggaggc cagaaacagc ggtcgacaga gactggaagt cgacacagaa ccgtttcgga  1260
ggaccagatg cggttatgga cttccagacg gttggcgaaa ctgaatggac caagatcaag  1320
agccggctat ag                                                      1332
```

<210> SEQ ID NO 61
<211> LENGTH: 443
<212> TYPE: PRT
<213> ORGANISM: Aspergillus niger

<400> SEQUENCE: 61

```
Met Ala Pro Ser Thr Val Thr His Asp Ser Thr Ile Leu Val Val Gly
1               5                   10                  15

Ala Gly Val Trp Gly Cys Ser Thr Ala Leu His Leu Ala Arg Arg Gly
            20                  25                  30

Tyr Lys His Val Thr Val Leu Asp Pro Tyr Thr Val Pro Ser Ala Ile
        35                  40                  45

Ala Ala Gly Asn Asp Ile Asn Lys Ile Met Glu His Lys Glu Pro Lys
    50                  55                  60

Ala Gly Glu Glu Ser Pro Arg Ser Ile Ala Phe Ala Thr Cys Thr Arg
65                  70                  75                  80

Ala Ala Leu Lys Ala Trp Arg Thr Asp Pro Val Phe Lys Gln Tyr Phe
                85                  90                  95

His Glu Thr Gly Val Ile Val Ser Gly His Thr Pro Ala Leu Ile Glu
            100                 105                 110

His Ile Arg Lys Asp Glu Ile Glu Ser Ser Asp Ala Asp Phe Val Glu
        115                 120                 125

Leu Lys Thr Ala Glu Asp Phe Arg Lys Thr Met Pro Pro Gly Val Leu
    130                 135                 140

Thr Gly Glu Phe Pro Gly Trp Lys Gly Trp Leu Asn Lys Ser Gly Ala
145                 150                 155                 160

Gly Trp Ile His Ala Lys Lys Ala Met Ile Ser Ala Tyr Thr Glu Ala
                165                 170                 175

Lys Arg Leu Gly Val Asn Phe Ile Thr Gly Ser Pro Gln Gly Asn Val
            180                 185                 190

Val Ser Leu Val Tyr Glu Asn Gly Asp Val Val Gly Ala Lys Thr Ser
        195                 200                 205

Asp Gly Val Ile His Arg Ala Asp Gln Thr Ile Leu Ala Ala Gly Ala
    210                 215                 220

Gly Ser Asp Arg Leu Leu Asp Phe Lys Lys Gln Leu Arg Pro Thr Ala
225                 230                 235                 240

Trp Thr Leu Ser His Ile Gln Met Thr Pro Glu Glu Ala Lys Gln Tyr
                245                 250                 255
```

```
Lys Asp Leu Pro Val Leu Phe Asn Ile Ala Lys Gly Phe Phe Met Glu
            260                 265                 270

Pro Asp Glu Asp Lys His Glu Leu Lys Ile Cys Asp Glu His Pro Gly
        275                 280                 285

Tyr Cys Asn Phe Ile Pro Asp Pro Ala Arg Ser Gly Glu Ile Arg Ser
    290                 295                 300

Ile Pro Phe Ala Lys His Gln Ile Pro Leu Glu Ala Glu Ala Arg Val
305                 310                 315                 320

Lys Asp Phe Leu Arg Asp Thr Met Pro His Leu Ala Asp Arg Pro Leu
                325                 330                 335

Val Phe Ala Arg Ile Cys Trp Asp Ala Asp Thr Val Asp Arg Ala Phe
                340                 345                 350

Leu Ile Asp Lys His Pro Asp His Pro Ser Leu Leu Val Ala Val Gly
                355                 360                 365

Ala Ser Gly Asn Gly Ala Met Gln Met Pro Thr Ile Gly Gly Phe Ile
370                 375                 380

Val Asp Ala Leu Glu Gly His Leu Gln Asp Glu Leu Lys His Val Val
385                 390                 395                 400

Arg Trp Arg Pro Glu Thr Ala Val Asp Arg Asp Trp Lys Ser Thr Gln
                405                 410                 415

Asn Arg Phe Gly Gly Pro Asp Ala Val Met Asp Phe Gln Thr Val Gly
                420                 425                 430

Glu Thr Glu Trp Thr Lys Ile Lys Ser Arg Leu
            435                 440

<210> SEQ ID NO 62
<211> LENGTH: 46
<212> TYPE: DNA
<213> ORGANISM: Artificial Sequence
<220> FEATURE:
<223> OTHER INFORMATION: primer

<400> SEQUENCE: 62
cccttaatta actcataggc atcatggcac cctccacggt aaccca                46

<210> SEQ ID NO 63
<211> LENGTH: 34
<212> TYPE: DNA
<213> ORGANISM: Artificial Sequence
<220> FEATURE:
<223> OTHER INFORMATION: primer

<400> SEQUENCE: 63
cgaggcgcgc cagtagttat ggaaggtata atca                             34

<210> SEQ ID NO 64
<211> LENGTH: 1505
<212> TYPE: DNA
<213> ORGANISM: Artificial Sequence
<220> FEATURE:
<223> OTHER INFORMATION: synthetic product

<400> SEQUENCE: 64
cccttaatta actcataggc atcatggcac cctccacggt aacccatgat tctaccatcc    60
tcgtggtggg agcgggtgta tggggttgtt ctactgcttt gcatttggct cgtcgcggat   120
ataagcatgt cacggttcta gacccctaca cggtcccatc cgcaatcgca gccggcaatg   180
atatcaacaa gatcatggaa cacaaggagc ccaaaggtat gtctgcaccg ttcagccaat   240
gaccatcttc caacgctaac aactccaaca gcaggcgaag aaagtccacg cagcattgcg   300
```

```
ttcgcgacgt gcactcgtgc cgctctgaaa gcgtggcgga cggatcctgt tttcaagcag      360
tactttcatg agaccggtgt catagtatcc ggtcataccc cggcactcat tgagcacatc      420
cgcaaagacg aaatcgagtc atctgatgca gactttgtcg aattgaagac agcagaagac      480
ttccgaaaga caatgcctcc aggtgttctc actggtgagt ttcctggctg gaagggctgg      540
ttgaacaagt cgggtgccgg ctggattcat gccaagaaag ccatgatctc tgcgtacact      600
gaagccaagc gtcttggggt caacttcatc actggatctc cccaggggaa cgttgtatca      660
ctagtatacg agaatggaga tgtggttgga gctaaaacgt ccgatggggt cattcatcga      720
gcagaccaaa ccattttggc agccggtgcg ggaagtgacc gtctcctgga tttcaagaaa      780
cagctgcgtc ctactgcctg gacgctctct catattcaga tgaccoctga ggaggccaag      840 cagtacaagg atttacccgt gcttttcaat attgcgaagg ggttcttcat ggagcctgat      900
gaggataagc acgaactgaa gatctgtgac gagcatcctg gatactgtaa ctttattcca      960
gaccctgcaa gatccggcga gatcagaagc atcccatttg cgaagcatca aattcccctg     1020
gaggccgaag ctcgcgttaa ggacttcctg cgggatacaa tgccacactt ggccgaccgt     1080
ccgctggtat ttgcccgtat ctgctgggat gctgacacgg tagatcgcgc cttttgatc      1140 gataaacatc ctgaccaccc ttcactgctg gtcgccgtgg gagcttctgg gaacggggct     1200
atgcagatgc ccactattgg agggttcatt gtggatgcac tggagggtca cctacaagat     1260
gagctaaaac atgtcgttcg gtggaggcca gaaacagcgg tcgacagaga ctggaagtcg     1320
acacagaacc gtttcggagg accagatgcg gttatggact tccagacggt tggcgaaact     1380
gaatggacca agatcaagag ccggctatag atgagcggtc atgtatgaga gcgaaatgca     1440
aatagtgata ttgccatgaa atatcagctt atgattatac cttccataac tactggcgcg     1500
cctcg                                                                 1505
```